(12) United States Patent
Poser et al.

(10) Patent No.: US 12,734,050 B2
(45) Date of Patent: Sep. 15, 2026

(54) HEIGHT ADJUSTABLE PROSTHESIS PYRAMID CONNECTOR

(71) Applicant: OTTO BOCK HEALTHCARE LP, Austin, TX (US)

(72) Inventors: Florian Wilhelm Sebastian Poser, Salt Lake City, UT (US); Vaughn Roy Anderson, Highland, UT (US); Jeff Waldmuller, Salt Lake City, UT (US); Douglas Rush, Salt Lake City, UT (US); Clifton Christensen, Salt Lake City, UT (US)

(73) Assignee: OTTO BOCK HEALTHCARE LP, Austin, TX (US)

( * ) Notice: Subject to any disclaimer, the term of this patent is extended or adjusted under 35 U.S.C. 154(b) by 717 days.

(21) Appl. No.: 18/024,267

(22) PCT Filed: Sep. 1, 2021

(86) PCT No.: PCT/US2021/048703

§ 371 (c)(1),
(2) Date: Mar. 1, 2023

(87) PCT Pub. No.: WO2022/051392

PCT Pub. Date: Mar. 10, 2022

(65) Prior Publication Data

US 2023/0293321 A1 Sep. 21, 2023

Related U.S. Application Data

(60) Provisional application No. 63/073,360, filed on Sep. 1, 2020.

(51) Int. Cl.

| | |
|---|---|
| ***A61F 2/66*** | (2006.01) |
| ***A61F 2/76*** | (2006.01) |
| *A61F 2/50* | (2006.01) |

(52) U.S. Cl.
CPC .................. *A61F 2/76* (2013.01); *A61F 2/66* (2013.01); *A61F 2002/5016* (2013.01); (Continued)

(58) Field of Classification Search
CPC ...... A61F 2/76; A61F 2/66; A61F 2002/5016; A61F 2002/6614; A61F 2002/5079
See application file for complete search history.

(56) References Cited

U.S. PATENT DOCUMENTS

| | | | | |
|---|---|---|---|---|
| 5,653,768 A * | 8/1997 | Kania | A61F 2/76 623/49 |
| 7,520,904 B2 * | 4/2009 | Christensen | A61F 2/70 623/47 |
| 2020/0000611 A1 | 1/2020 | Ossur | |

FOREIGN PATENT DOCUMENTS

| | | |
|---|---|---|
| JP | 6640101 | 2/2020 |

OTHER PUBLICATIONS

Written Opinion of the International Searching Authority issued in PCT/US2021/048703, mailed Jan. 31, 2022, 7 pgs.

(Continued)

*Primary Examiner* — Bruce E Snow

(74) *Attorney, Agent, or Firm* — HOLLAND & HART LLP

(57) ABSTRACT

A prosthetic device and related methods having height adjustment features. A prosthetic foot includes an elongate support member comprising fiber reinforced material and having a support surface configured to rest upon a ground surface prior to use, an adapter mounted to the support member and configured to secure the prosthetic foot to another prosthetic device, and a height adjustable feature configured to adjust a height of the adapter relative to the support surface.

22 Claims, 38 Drawing Sheets

(52) U.S. Cl.
CPC ................. *A61F 2002/5055* (2013.01); *A61F 2002/5083* (2013.01); *A61F 2002/6614* (2013.01); *A61F 2002/6657* (2013.01)

(56) References Cited

OTHER PUBLICATIONS

International Search Report issued in PCT/US2021/048703, mailed Jan. 31, 2022, 4 pgs.
Ossur Academy Aug. "Cheetah—Alignment Setup", youtube. Online. Aug. 26, 2014, 2 pgs.
CBS News: "Blade Runner's' artificial legs controversial at Olympics". youtube. Online Aug. 1, 2012, 1 pg.

* cited by examiner 10
14
44
40
50
52
$H_1$
16
46
12
42
54
48
$H_2$
$H_3$
22

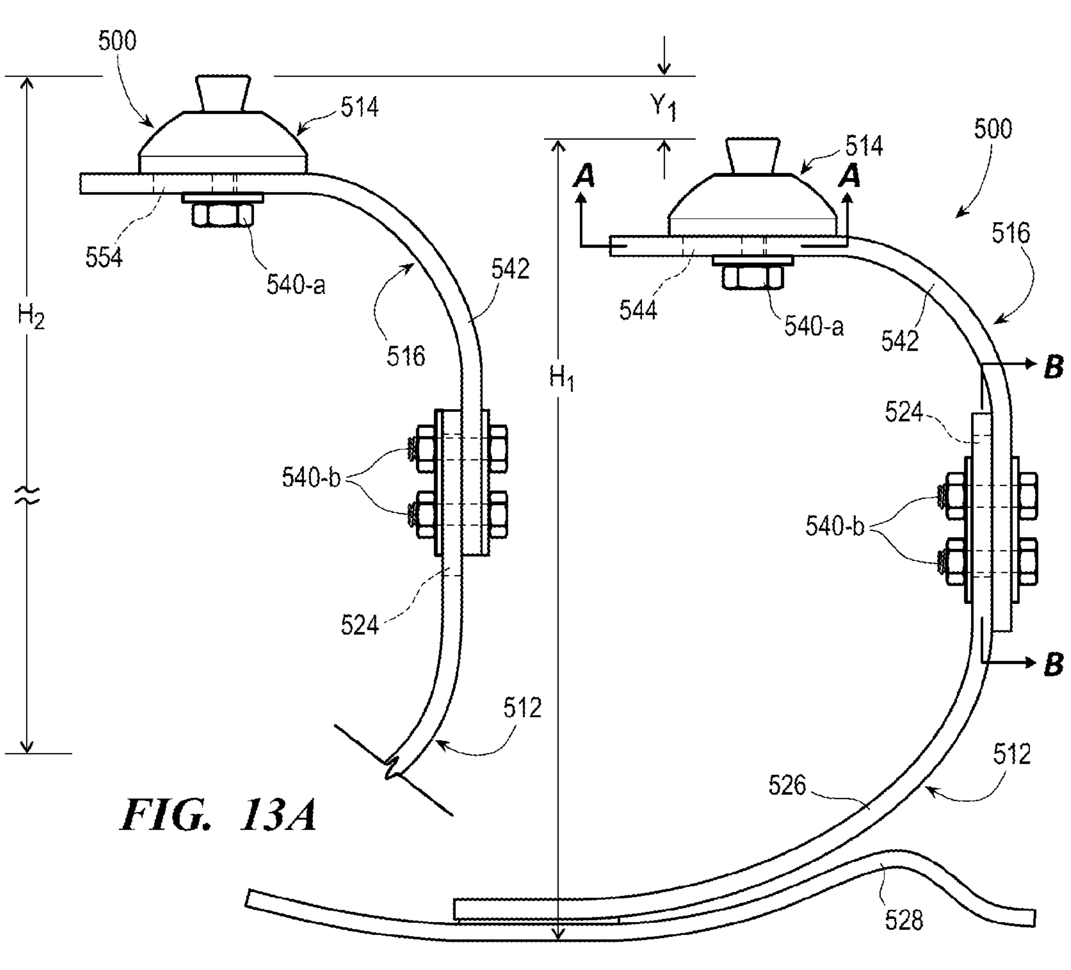
FIG. 13A
FIG. 13
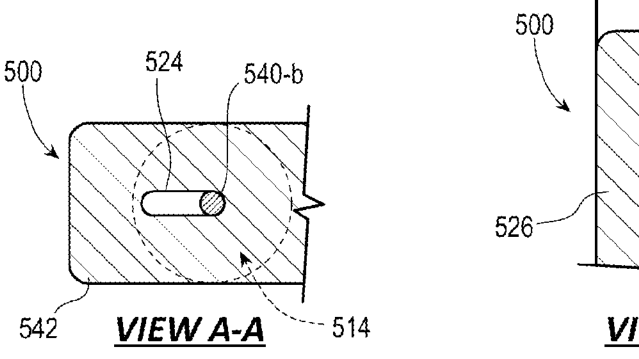
FIG. 14A
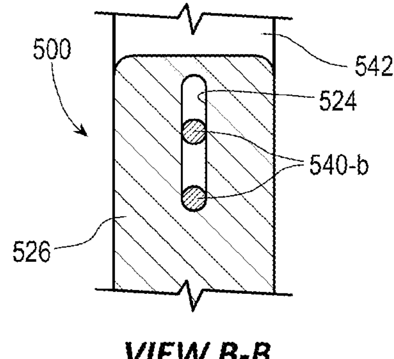
FIG. 14B

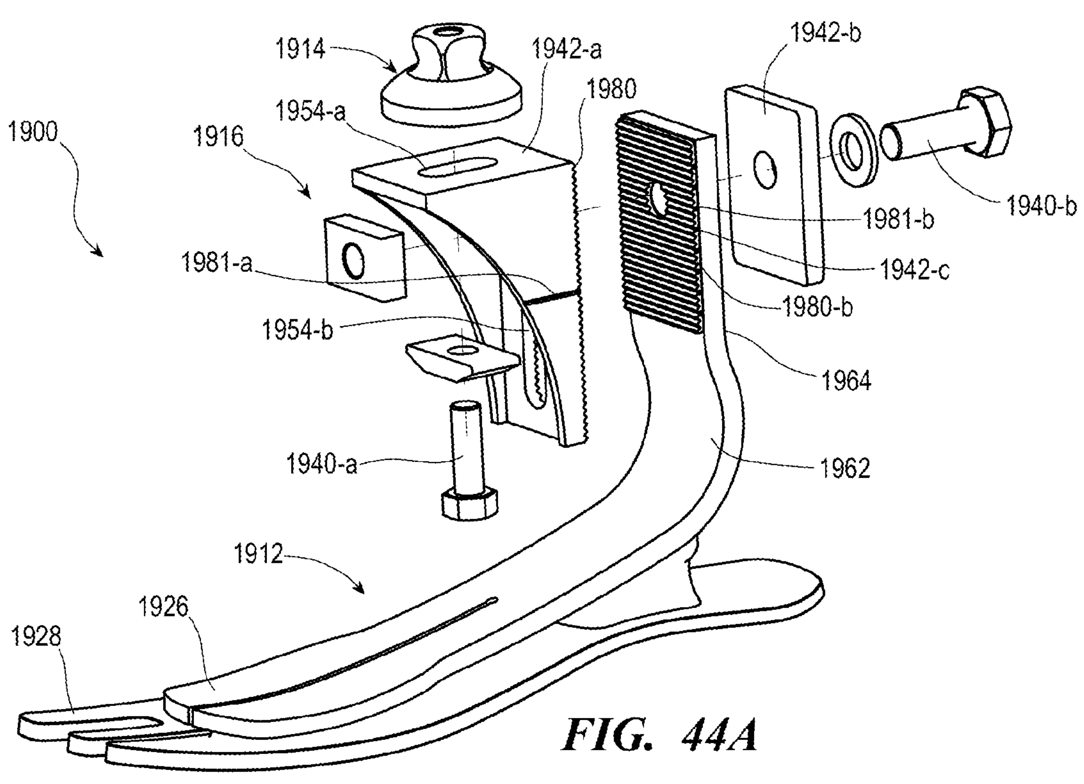
FIG. 44A
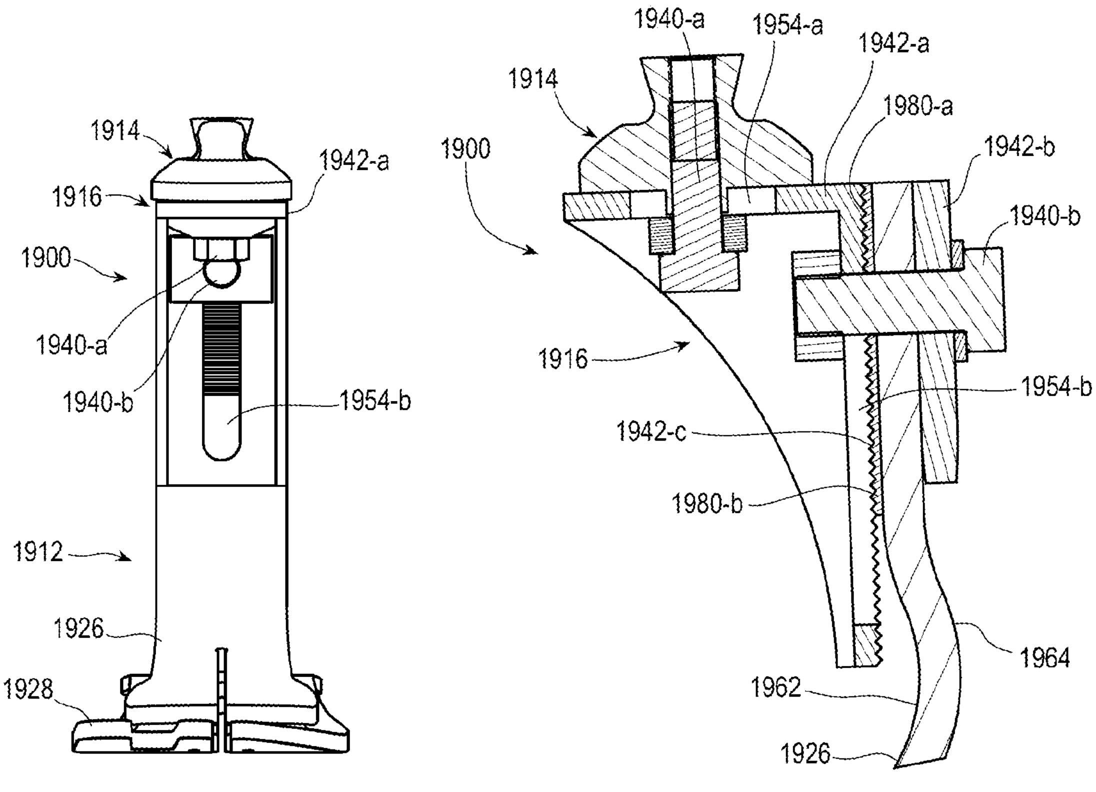
FIG. 44B
FIG. 44C

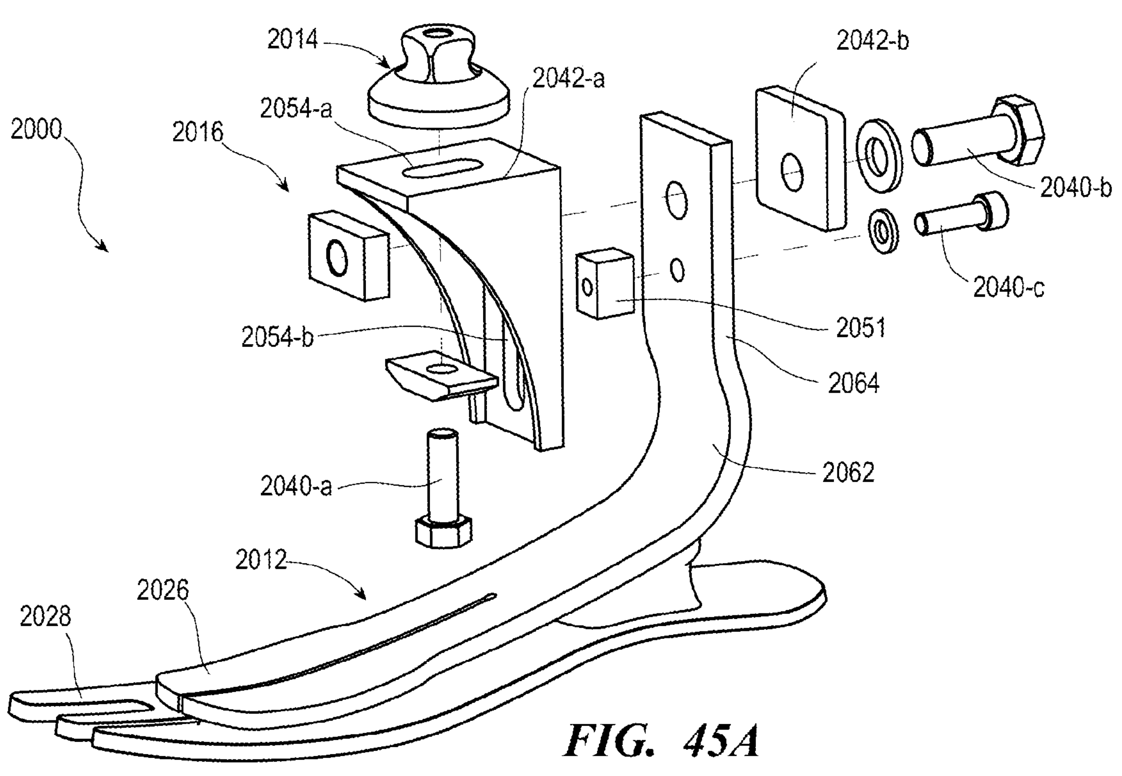
FIG. 45A
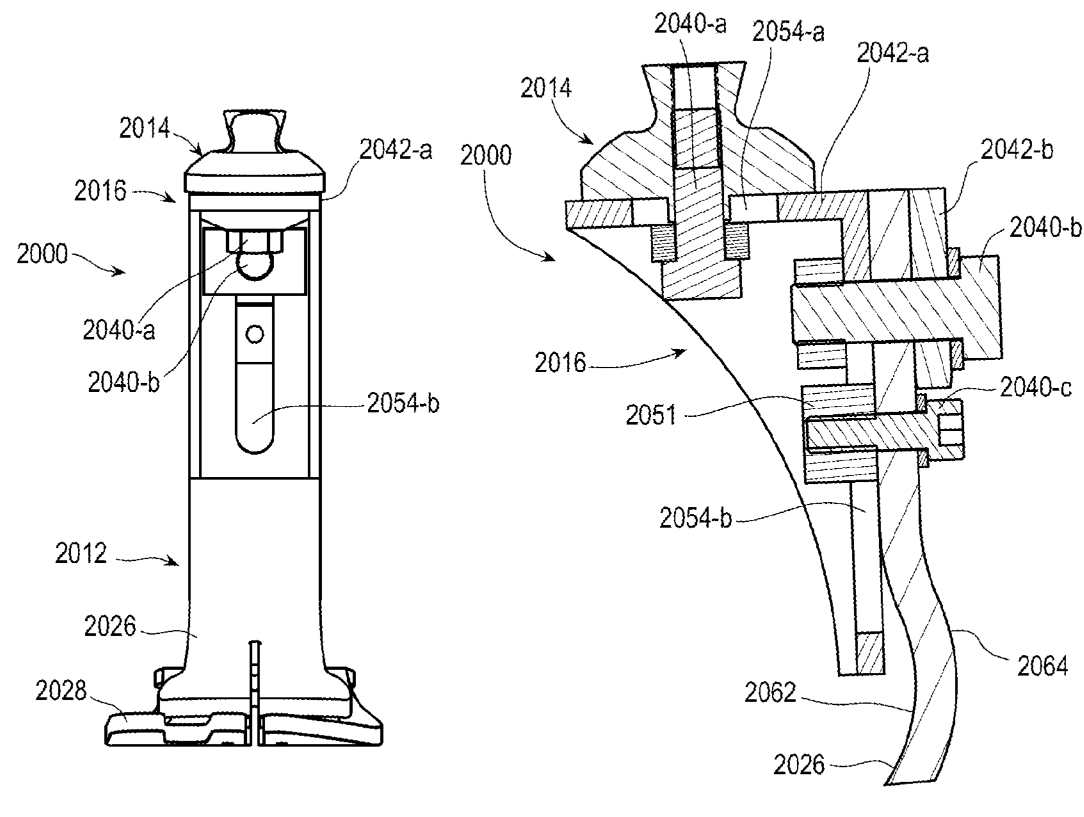
FIG. 45B
FIG. 45C

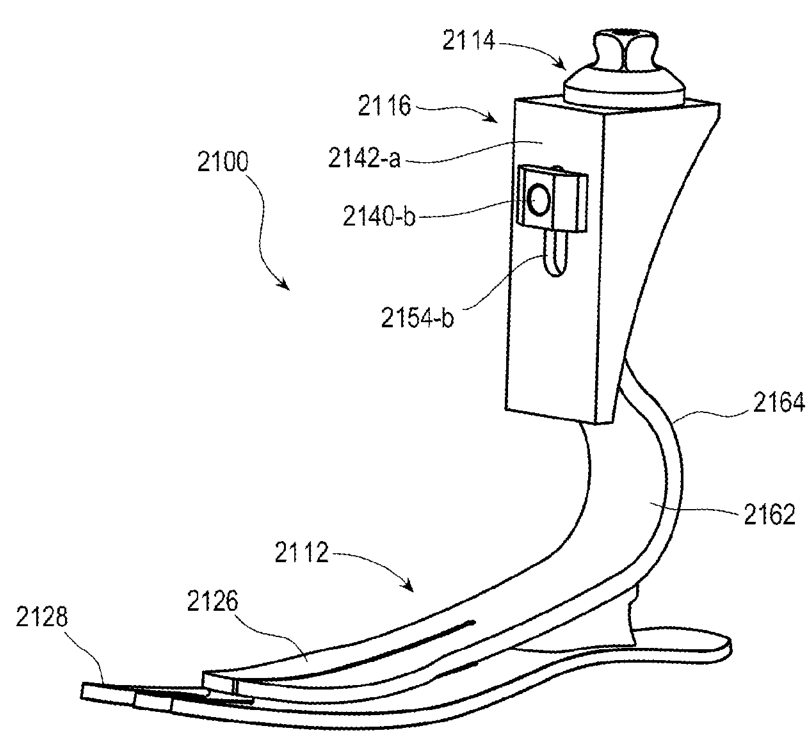
FIG. 46A
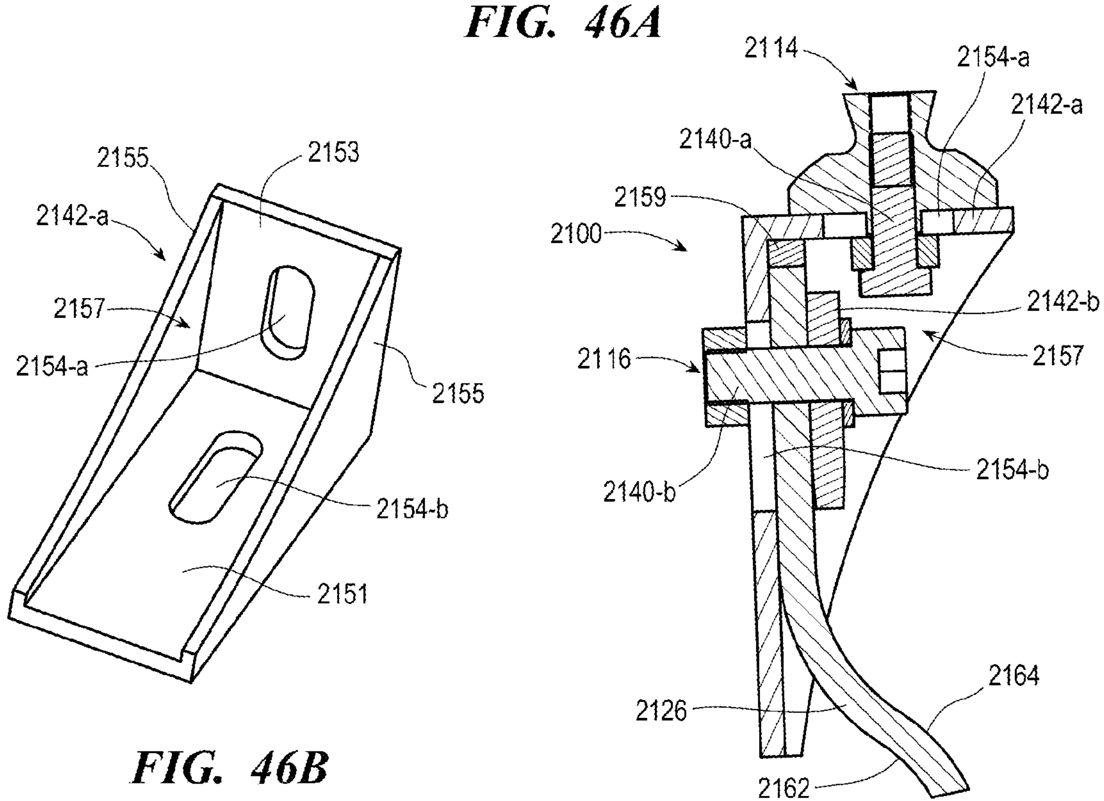
FIG. 46B
FIG. 46C

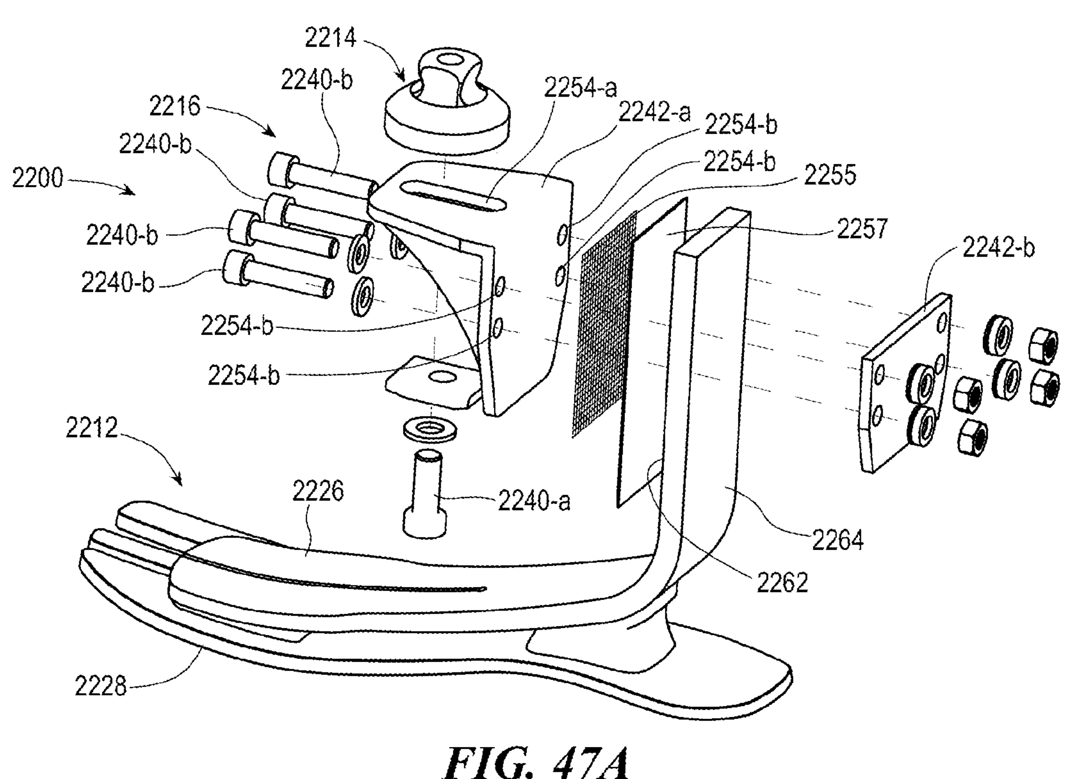
*FIG. 47A*
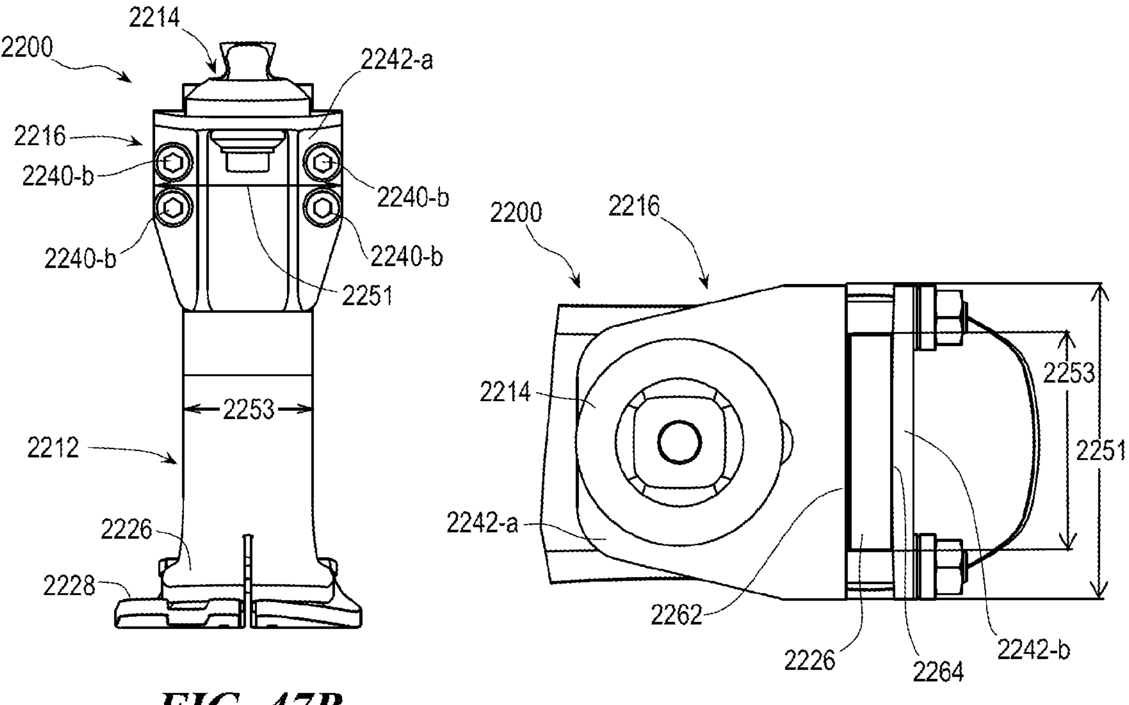
*FIG. 47B*
*FIG. 47C*

HEIGHT ADJUSTABLE PROSTHESIS PYRAMID CONNECTOR

CROSS REFERENCE TO RELATED APPLICATION

This is a national phase entry of International Patent Application No. PCT/US2021/048703, filed 1 Sep. 2021, which claims priority to and the benefit of U.S. Provisional Patent Application No. 63/073,360, filed 1 Sep. 2020, and entitled HEIGHT ADJUSTABLE PROSTHESIS PYRAMID CONNECTOR, the disclosures of which are incorporated herein by reference in their entireties.

TECHNICAL FIELD

The present disclosure relates generally to prosthetic devices, and more particularly relates to height adjustable adapters and connectors for prosthetic devices, and related methods of manufacturing and use of such height adjustable adapters and connectors.

BACKGROUND

Prosthetic feet generally include spring-like members which are flexible and resilient. To mimic, as closely as possible, the function of a human foot the members must deflect under the user's weight. Unfortunately, most existing prosthetic feet are not nearly as adaptable to varying uses and conditions as the human foot. Prosthetic feet provide trade-offs between flexibility and durability. In general, stiff prosthetic foot components are stronger than more flexible components and strong components are stiffer than more flexible components. During strenuous, high load activities, a stiff and strong prosthetic foot components provide more optimum support and strength an amputee requires while more flexible components provide more bending function and comfort during less demanding activities.

Moreover, matching the stiffness of the foot to the desires of an amputee is challenging. Depending on the activity an amputee is performing (i.e., walking vs. running) an improved prosthetic foot will provide some user adjustability to provide optimum performance during different activities and/or some adjustment so a prosthetic foot can be fine-tuned to a particular user's preference.

Such flexibility and the ability to deflect often require the spring members forming the foot to be structurally weak, or more flexible. On the other hand, it is desirable to make the members as strong or stiff as possible from a structural and durability standpoint. Thus, there may be a trade-off between obtaining a sufficient cushion or feel, with spring members that are weak or flexible and over-deflect, and obtaining a solid and durable structural foot, with stiffer members.

The stiffness of prosthetic feet typically varies according to the intended use. Feet intended for everyday use are typically too flexible and fragile for athletic use. Multiple-use feet have been designed which are capable of many different uses, but without being particularly well-suited for any specialized use. In addition, users may have different weights. Thus, prosthetic feet may require a high degree of custom design or be particularly tailored to the individual user. However, it is desirable from a cost and manufacturing standpoint to create a foot that is usable by individuals of varying weight, strength, walking style, and preferred activities.

The connection point between the prosthetic adapter and the upper foot plate is often a challenge for prosthetic foot designers. This is typically the location that experiences the most extreme stress in a prosthetic foot, therefore is important to optimize the connection to maximize both foot durability and flexibility. Over time, prosthetic foot designers have improved the connection between prosthetic adapters and the remaining components of a foot. Prosthetic adapters are typically made of metal and the upper foot plate is typically made of a fiber reinforced composite laminate.

A first generation of a prosthetic adapter interface was flat and square or rectangular with four bolt holes at the corners of the interface: two at the anterior end and two at the posterior end of the adapter. This resulted in high stresses in the anterior bolts, high contact stresses in the upper foot plate at the anterior edge of the pyramid, and poor roll-over characteristics for the foot.

Typically, the practitioner would select the most suitable prosthetic foot for the "most used" circumstances of the user. If the user wanted to engage in higher level, less common activities, the practitioner would prescribe an additional prosthetic foot that would be suitable this other level of activity. It was not uncommon for an amputee to have several different types of prosthetic feet that can be swapped out, depending on the current activity of the user. Also, pediatric users of prosthetic feet typically grow out of their prosthetic feet on a regular basis. This problem has typically been solved by simply replacing the foot on a regular basis, or fitting the patient with a foot that is not optimal, but one that the user can grow into.

Height adjustment has typically occurred by cutting a composite pylon or spring member and drilling mounting holes in the pylon to attach an adapter component to the pylon at a desired position. Drilling holes is a difficult task because the drill bit must be very sharp, hole placement must be highly accurate, and the drilling pressure must be carefully controlled to avoid delaminating layers of the composite that are located on an outer surface of the pylon. Expensive carbide drill bits are required for optimal results. Surface layers on prosthetic foot spring components are subjected to the high stress resulting from the drilling and any surface defect can result in a substantial loss of strength and durability for the prosthetic device. In addition, it has been important to cut the pylon to the correct height with high accuracy. Any error in cutting the height of the pylon frequently result in discarding an expensive prosthetic foot.

For these and other reasons, there is a need to provide improved prosthetic feet and respective components that are functional and/or adaptable for a variety of activities and user needs.

SUMMARY

The present disclosure relates to a device or mechanism that connects a prosthetic device, such as a prosthetic foot, to a pylon and/or pyramid adapter, and an adjustable pyramid adapter. When the device is connected to the spring element of the prosthetic device, the position height of the pyramid adapter can be adjusted without physically modifying the height of the spring element, thereby satisfying numerous patients and their specific circumstances using a single prosthetic device. The present disclosure may allow the practitioner to adjust the height position of the pyramid adapter without having to modify or cut the spring element(s) of the prosthetic device. The geometry of the connecting device and related adjustable pyramid adapter may also provide the user with a smooth roll-over. Other embodiments allow for errors when a spring element is cut to length for a specific amputee. The required precision of the cut is significantly reduced, which reduces the risk of a spring or spring assembly becoming unusable.

One aspect of the present disclosure relates to a height adjustable adapter assembly that includes at least one of the following features, components, or functionality:

- Two components slidable vertically between each other
- Position lockable
- Indexable to assist with discrete adjustment settings
- Vertical slot(s) in adapter
- Toothed interface between the two sliding components
- Adapter with center rib for alignment with pylon
- Adapter with side flanges for alignment with pylon
- Roll-up surface for pylon
- L-adapter with vertical leg extending proximal to a horizontal portion
- L-Adapter extending anterior
- L-adapter with vertical leg extending proximal to horizontal portion and horizontal slot for anterior/posterior pyramid adjustment
- Adapter with pylon (e.g., spring member)
- Adapter with multiple contoured roll-up surfaces to mitigate contact pressure, mitigate the resulting stresses in the spring members, and increase flexibility in spring components. Multiple contoured surfaces may reduce stresses and increase flexibility both the loading response and terminal stance phases of gait.

Another aspect of the present disclosure relates to a height adjustable adapter for use with a prosthetic device such as a prosthetic foot, the adapter and/or prosthetic device including at least one of the following features or functionality:

- Slotted pylon(s) (e.g., spring member with vertical portion)
- Pylon mounted anterior to adapter
- 2-piece pylon with height adjustment between—one or both with vertical slots
- 2-piece, generally C-shaped pylon with height adjustment between—one or both with vertical slot and possibly including a spacer
- Pylon with toothed engagement surface
- Pylon with bonded-on separate toothed engagement surface (e.g., metal or injection molded, such as an injection molded composite)
- Foot with tapered vertical pylon
- Foot with spacer between pylons which has side flanges for pylon alignment
- Foot with space between pylons which has a center rib for pylon alignment
- Foot with height adjustable adapter features
- Pylon with two center slots (e.g., a split for the toes and a slot for mounting the adapter) and movable pyramid, wherein no drill holes are required
- A prosthetic foot with a hook-shaped spring member (i.e., an upside down question mark shaped)

One aspect of the present disclosure relates to a prosthetic foot that includes an elongate support member comprising fiber reinforced material and having a support surface configured to rest upon a ground surface prior to use, an adapter mounted to the support member and configured to secure the prosthetic foot to another prosthetic device, and a height adjustable feature configured to adjust a height of the adapter relative to the support surface.

The adapter may include a base portion and a pyramid connector. The pyramid connector may be configured to secure the prosthetic foot to another prosthetic device, and the base portion may be configured to secure the adapter to the support member via the height adjustable feature. The height adjustable feature may include a first portion mounted to the support member, and a second portion mounted to the adapter, and the first and second portions may be slidable relative to each other to provide height adjustment of the adapter relative to the support surface. The first portion may include a groove, and the second portion may include a protrusion positioned and slidable within the groove. The height adjustable feature may include at least one set screw to releasable hold the adapter in an adjusted height relative to the support surface. The height adjustable feature may include a slot formed in the support member, and a bolt extending through and slidable within the slot to provide the height adjustment of the adapter. The height adjustable feature may include an adapter support to which the adapter is mounted, the adapter support having a slot formed therein, and a bolt extending through the support member and slidable within the slot to provide the height adjustment of the adapter. The height adjustable feature may include an adapter support to which the adapter is mounted, and a bolt extending through the support member and into engagement with the adapter support to releasably secure the adapter support to the support member.

The adapter support may include a contoured portion, and the contoured portion may face a surface of the support member and be configured to contact the support member during use of the prosthetic foot to alter a moment arm length between the bolt and adapter support. The support member may include a vertical portion extending in a vertical direction, and the adapter may be positioned anterior of the vertical portion. The support member may include a vertical portion extending in a vertical direction, and the adapter may be positioned posterior of the vertical portion. The support member may include a vertical portion extending in a vertical direction, and the vertical portion may include at least one slot formed therein, and the at least one slot may be arranged vertically. The support member may include a vertical portion extending in a vertical direction, and the height adjustable feature may include an adapter support having at least one slot formed therein. The at least one slot may be arranged vertically, and the adapter support may be adjustably mounted to the vertical portion of the support member. The support member may include a vertical portion extending in a vertical direction, and the height adjustable feature may include an adapter support having at least one slot formed therein. The at least one slot may be arranged vertically, the adapter support may be mounted to the vertical portion of the support member, and the adapter may be adjustably mounted to adapter support.

Another aspect of the present disclosure relates to a prosthetic foot that includes a spring assembly having a first portion extending horizontally and arranged to contact a ground surface, and a second portion having an adapter mounting portion, and an adapter assembly that includes a connector configured to releasably secure the prosthetic foot to a prosthetic device, a base portion interposed between the connector and the spring assembly, and at least one fastener to releasably secure the adapter assembly to the spring assembly. The prosthetic foot is operable to adjust an effective height of the connector relative to the ground surface.

The second portion of the spring assembly may be arranged vertically. The second portion of the spring assembly may be arranged horizontally. One of the second portion of the spring assembly and the base portion may include at least one slot through which the at least one fastener extends and is slidable within to provide the height adjustment.

A further aspect of the present disclosure relates to a method of adjusting an effective height of a prosthetic device. The method includes providing a prosthetic device comprising an elongate composite spring member, an adapter, and a height adjustable feature interposed between the spring member and the adapter. The method also includes operating the height adjustable feature to move the adapter relative to the spring member to adjust an effective height of the adapter. The spring member may include a vertically arranged portion, and the height adjustable feature may be movable vertically relative to the vertically arranged portion. At least one of the vertically arranged portion and the height adjustable feature may include at least one slot, and the prosthetic device may further include at least one fastener extending through the at least one slot to releasably hold a position of the adapter relative to the spring member.

Another aspect of the present disclosure relates to a method of adjusting an effective height of a prosthetic foot. The method includes providing a prosthetic foot comprising an elongate composite spring assembly having a first portion configured to contact a ground surface and a vertically arranged portion, an adapter, and a height adjustable feature interposed between the vertically arranged portion and the adapter. The method also includes adjusting a position of the adapter relative to the spring member with the height adjustable feature to change a height of the adapter relative to the ground surface.

The height adjustable feature may include an indexed member that provides predefined height adjustments. At least one of the spring assembly, the adapter, and the height adjustable feature may include at least one slot, and the prosthetic device may further include at least one fastener extending through the at least one slot to releasably hold a position of the adapter relative to the spring assembly. The height adjustable feature is a vertical height adjustment relative to the foot orientation as oriented on a prosthetic leg. Prosthetic feet are designed for use with a typical shoe and have a designed-in heel height to accommodate a shoe. In addition, most prosthetic feet utilize a footshell, which is a cosmetic cover which has the appearance of a human foot and provides an interface or filler between the structural components of a prosthetic foot and a shoe. The footshell may be thicker in the heel area than in the forefoot area and the foot is designed to accommodate this additional thickness. The embodiments shown may depict a prosthetic foot in the optimum and intended orientation when connected to a prosthetic socket or leg when and amputee is standing on flat ground. The pylon of the foot and/or the adjustable height feature may be tilted 0-5 degrees forward from vertical or 85-90 degrees from a horizontal ground surface. Vertical adjustment may include a small posterior or anterior movement of the foot relative to a prosthetic socket due to the preferred 0-5 degree angle of a pylon.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the spirit and scope of the appended claims. Features which are believed to be characteristic of the concepts disclosed herein, both as to their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the embodiments may be realized by reference to the following drawings. In the appended figures, similar components or features may have the same reference label.

FIGS. 13 and 13A are side views of another prosthetic foot in accordance with the present disclosure in different height-adjusted positions.

FIG. 14A is a cross-sectional view of the prosthetic foot shown in FIG. 13A taken along cross-section indicators A-A.

FIG. 14B is a cross-sectional view of the prosthetic foot shown in FIG. 13 taken along cross-section indicators B-B.

FIG. 44A is an exploded perspective view of another example prosthetic device having height adjustment features in accordance with the present disclosure.

FIG. 44B is a front view of the prosthetic device shown in FIG. 44A.

FIG. 44C is a cross-sectional side view of the prosthetic device shown in FIG. 44A.

FIG. 45A is an exploded perspective view of another example prosthetic device having height adjustment features in accordance with the present disclosure.

FIG. 45B is a front view of the prosthetic device shown in FIG. 45A.

FIG. 45C is a cross-sectional side view of the prosthetic device shown in FIG. 45A.

FIG. 46A is a perspective view of another example prosthetic device having height adjustment features in accordance with the present disclosure.

FIG. 46B is a perspective view of a first bracket of the prosthetic device shown in FIG. 46A.

FIG. 46C is a partial cross-sectional side view of the prosthetic device shown in FIG. 46A.

FIG. 47A is an exploded perspective view of another example prosthetic device having height adjustment features in accordance with the present disclosure.

FIG. 47B is a front view of the prosthetic device shown in FIG. 47A.

FIG. 47C is a top view the prosthetic device shown in FIG. 47A.

Figure 1:
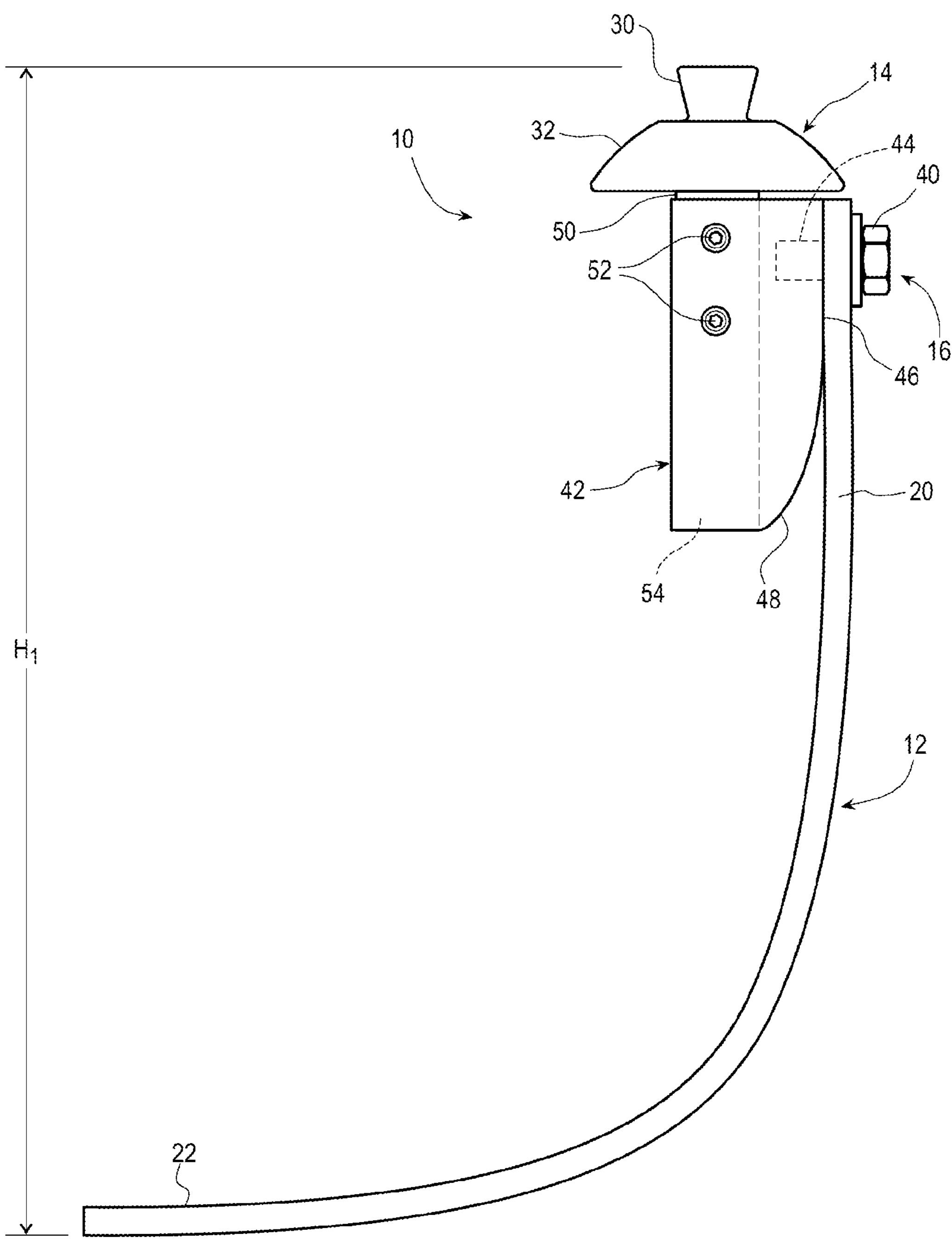
FIG. 1 is a side view of an example prosthetic foot having a height adjustable feature in accordance with the present disclosure.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

The present disclosure is generally directed to prosthetic devices, and more particularly relates to adaptors (e.g., pyramid adapters) for prosthetic devices, and related methods for using and adjusting such adaptors. The present disclosure also relates to a prosthetic foot with a height adjustable prosthetic adapter, and related methods of manufacturing and operating a height adjustable prosthetic adapter. The adapter and/or prosthetic device to which the adapter is mounted, may include a device or mechanism that connects a prosthetic device (e.g., prosthetic foot) to, for example, a composite pylon or spring member. When the device is connected to the spring element of the foot, the height of the adapter component can be adjusted. In some embodiments this is achieved without physically modifying the height of the spring element.

Proper alignment of a prosthetic device such as a prosthetic foot includes determining the appropriate height of the prosthetic device relative to the socket. The prosthetist typically begins with initial bench alignment, and then makes further adjustments during dynamic alignment assessment. In the case of a prosthetic foot, the prosthetist couples a pyramid adapter plate to the spring element of the foot. For some existing sport feet, or J-shaped feet, the height is set by pre-drilling holes through the foot plate. If the height needs to be adjusted, new holes may need to be drilled through the laminate foot element. Additional holes can weaken the laminate, and in some cases the foot is scrapped if too much weakening occurs. If the height of the mount is lowered, the excess laminate that extends higher than the adapter may need to be cutoff. Cutting the laminate can be time-consuming, and the prosthetist may not have the equipment necessary to make these modifications. The alignment adapter described herein may advantageously allow for improved height alignment of prosthetic J-shaped feet and other prosthetic devices without the need or requirement to modify the structure of the prosthetic device (e.g., prosthetic foot and/or ankle pylon).

The alignment adapter described herein may advantageously allow for improved height adjustment without the need to modify any foot components, thereby potentially improving ease of use.

The alignment adapter described herein may advantageously allow for improved height adjustment with minimal modification of foot components, thereby potentially improving ease of use.

The alignment adapter described herein may advantageously allow for improved height adjustment with minimal or no effect on strength and durability of a foot.

The alignment adapter described herein may advantageously allow for improved height adjustment with more room for error when modifying the height of spring components.

The alignment adapter described herein may advantageously allow for improved height adjustment with foot performance enhancements. For example, the adapter may include one or more contoured surfaces which roll-up onto a spring surface. The rolling action, which occurs during the gait cycle gradually changes the stiffness characteristics of the spring element resulting in a smoother rollover for the user. This feature can be used, for example, during the loading response phase because a contoured surface is located on the posterior side of the vertically oriented spring element.

The height adjustment adapter may further include a contoured base that is attached to the spring element of the prosthetic device. The adapter is connected at one end of the adapter base, and the opposite end of the adapter is not connected to the spring element. This attachment configuration allows the adapter to "roll upon" the contoured bottom surface of the unattached section of the adapter base. The rolling action, which occurs during the gait cycle, may gradually change the stiffness characteristics of the spring element resulting in a smoother rollover for the user. Many conventional prosthetic foot designs attempt to accomplish a fluid transition by incorporating springs of different types and shapes to store and release energy during motion of the prosthetic foot. However, these energy-storing and energy-releasing designs typically do not provide the desired degree of stride fluidity and rollover characteristics during a stride cycle.

In order to satisfy numerous patients and their specific circumstances, a prosthetic foot with an adjustable height is a desirable aspect of the foot and its performance. The present disclosure provides a pyramid adapter (also referred to as a pyramid connector, adapter, or connector) with an adjustment feature that provides a height adjustment for a prosthetic device such as a prosthetic foot. The pyramid adapter may have an adjustable height feature, or a connection point between the pyramid adapter and the remaining structure of the prosthetic device may provide a relative height adjustment for the pyramid adapter.

The effective height may include, but not be limited to, a height of the pyramid adapter relative to a spring member of the prosthetic device to which the pyramid adapter contacts and is mounted. In some examples, the effective length may be measured or determined at least in part based on a connection point between the adapter and the spring to which the adapter is mounted. The connection point may be defined by, for example, a mounting bolt that provides releasable attachment of the adapter to the spring member. The effectively height typically is measured or determined when the prosthetic device is in a rest position or state, prior to application of a user's weight force or use of the prosthetic device by a user.

Lower limb prosthetic components may benefit from adjustability and are typically connected using an industry standard prosthetic pyramid connection. A prosthetic pyramid connection typically consists of a male pyramid connector/adapter and a complementary female pyramid connector/adapter connected to each other. The combination of the male and female adapters may provide for angular adjustment between two prosthetic components. The male portion may include two primary features: a pyramid protrusion and a contoured (e.g., spherical) surface. The pyramid protrusion may have four planar surfaces that are oriented in posterior, anterior, medial, and lateral directions. These surfaces may be angled with respect to a pyramid axis, wherein the pyramid axis extends along a longitudinal axis of the shin or thigh of the limb. The pyramid surfaces typically are angled in the range of about 10 degrees to about 30 degrees, and more particularly about 15 degrees. Due to the angles of the four pyramid surfaces, the protrusion necks down in a distal direction. The necked down end transitions to the contoured (e.g., spherical) surface. The contoured portion may be part of a separate base component with the pyramid protrusion fixedly and rigidly attached to the base component. Alternatively, the base component may be integrated to the spherical feature where the two features are combined into a single monolithic block of material.

The pyramid protrusion may be threaded into the base component with the threads glued or otherwise fixed to prevent unthreading. Alternate methods of fixedly attaching a pyramid protrusion to a base component including a spherical surface are possible such as, for example, creating a stud on the narrow end of the pyramid protrusion and molding the stud into a fiber reinforced moldable base material, or by deforming the stud such that the stud creates a strong interference fit between the a pyramid protrusion and the base component. A male pyramid adapter may be monolithic meaning it is formed or composed of a single, continuous material without joints or seams. However, as discussed herein, the male pyramid adapter may comprise a plurality of components, such as one or more components that adjust an effective length of the pyramid adapter.

A female pyramid adapter may include a predominantly hollow cylinder with a spherical surface formed on one end and four threaded fasteners. The inner surface of the cylinder may not be round or cylindrical as recesses are commonly formed on this surface to allow increased articulation of the male protrusion within the cylinder while adjusting the angle between the components. The spherical surfaces of both the male and female components have a near identical spherical radius to allow mating with each other. Fasteners (e.g., two or more fasteners) may be threaded into the cylinder at an angle relative to the cylinder axis (e.g., 15 degree angle), and the fasteners may engage one or more of the four planar surfaces of the male pyramid protrusion to releasably secure the position of the pyramid connection. By adjusting the depth of the fasteners in the female component, the angle between the male and female pyramid components can be changed and the angle between two prosthetic components can be adjusted. A female pyramid component may be referred to as a pyramid receiver. A female pyramid adapter may be monolithic. The threaded fasteners typically are separate components in a monolithic female pyramid adapter.

The male and female pyramid adapter may each have fastening provisions to be attached to adjacent components, such as holes for attaching the pyramid adapter to components of a prosthetic foot or prosthetic knee using, for example, fasteners (e.g., bolts or rivets), a clamp, or a bonding surface for bonding the adapter to an adjacent component such as prosthetic pylon, which may be, for example, a composite or metal tube. A male or female pyramid adapter component may be machined or formed directly onto a prosthetic device, for example, a prosthetic knee. For the purposes of this disclosure, a pyramid adapter may be either the male or female component of a pyramid connection and include either a pyramid protrusion and a spherical mating surface in the case of a male pyramid adapter or a spherical mating surface with multiple (e.g., four) threaded fasteners to engage and lock a pyramid protrusion in the case of a female adapter. A pyramid adapter may be fabricated separately from other components and include design features allowing the adapter to be attached to other prosthetic components in addition to connecting the complementary opposite component of a pyramid connection.

The present disclosure relates to prosthetic devices such as prosthetic feet that typically include a rigid pyramid adapter. A rigid pyramid adapter does not allow movement within the adapter. Some pyramid adapters include one or more axes of rotation within the adapter that allow the pyramid protrusion to rotate relative to the base of the adapter. Rotation about the axes may be controlled or limited by a hydraulic circuit, a bumper, or a mechanism that allows the heel height of the foot to be adjusted. The devices of the present disclosure are generally directed to pyramid adapters that are rigid and are intended to provide angular adjustment between the male and female adapter components of the pyramid connection, but not movement or articulation within either the male or female adapter components. Pyramid adapters that provide movement and adjustment within the adapter are typically more expensive to manufacture and may suffer from wear at surfaces associated with the axes that allow movement and any other component that restricts, controls, or prevents movement. This may result in reduced reliability. Prosthetic feet with such adapters may be referred to as hydraulic ankles, hydraulic feet, single axis feet, or adjustable heel height feet. A consequence of the high loads pyramid connections are subjected to and the desire to minimize the weight of all prosthetic components, is that a rigid pyramid adapter may exhibit a small amount of elastic deformation under the high forces imposed during a walking gait cycle, thus resulting in a small amount of angular change (e.g., less than two degrees) between any two surfaces within a pyramid connection.

The present disclosure, among other things, may provide a prosthetic foot with a mechanical mechanism to alter the effective height of the pyramid adapter relative to a ground surface that supports the prosthetic device to which the adapter is mounted, or to a certain feature of the prosthetic device. The prosthetic device may include an adjustment feature to alter the connection point of the pyramid adapter, thereby altering the location where the adapter contacts the prosthetic spring member. By adjusting the relative height of the pyramid adapter, the spring member and the stressed induced in the spring member of the prosthetic device are changed, thereby changing one or more performance characteristics of the prosthetic device. Additionally or alternatively, the change in relative height of the pyramid adapter may change a fit of prosthetic device for the user, a stability characteristic of the prosthetic device, or one or more alignment characteristics of the prosthetic device. In one example, by changing the relative height of the pyramid adapter and/or changing a connection location for the pyramid adapter relative to the remaining structure of the prosthetic device, the inherent stiffness of the prosthetic device is decreased or increased. This simple adjustment mechanism allows the prosthesis to optimize the prosthetic device for one or more of the size and weight of the user and the activity level of the user. In embodiments in which the adjustment mechanism is operable by the user, the user can make changes (e.g., stiffness changes) to optimize the performance of the prosthetic device for a specific activity.

In yet another embodiment, the pyramid adapter has a multi-piece construction and is configured such that a portion of the adapter can be adjusted changing the relative height of the adapter. Changing the height of the adapter effectively changes the one or more characteristics of the prosthetic foot.

These and other objects, features and advantages of the present invention become more apparent from a consideration of the following detailed description of disclosed example embodiments of the invention and the accompanying drawings.

FIG. 1 is a side view of an example prosthetic device in the form of a prosthetic foot 10. The prosthetic foot 10 has a spring assembly or support member 12, an adaptor 14, and an adjustment assembly 16. The adjustment assembly 16 is operable to provide a height adjustment of the adaptor relative to, for example, the spring assembly 12 and/or a ground surface upon which the prosthetic foot 10 is supported, particularly when the prosthetic foot 10 is in a rest position (e.g., without a load applied).

The spring assembly 12 includes a vertical portion 20 and a horizontal portion 22. The horizontal portion 22 is arranged and configured to contact the ground surface. The adaptor 14 is mounted to the vertical portion 20 via the adjustment assembly 16. The adaptor 14 includes a connector portion 30 in the form of a pyramid connector. The connector portion 30 is configured to secure the prosthetic foot 10 to another prosthetic device such as a pylon, prosthetic socket, prosthetic knee, or the like. The adaptor 14 also includes a base 32 to which the connector 30 is mounted. The adjustment assembly 16 is secured to the base 32.

The adjustment assembly 16 includes a fastener 40, a bracket 42, an extension 50 and set screws 52. The extension 50 is mounted to and extends from the base 32. The bracket 42 includes a slot 54, which is shown in further detail in FIGS. 3, 4A and 4B. The extension 50 is positioned within the slot 54 and provides a slide-able engagement between the extension 50 and the bracket 42. The bracket 42 is mounted to the spring assembly 12 with the fastener 40. The set screws 52 are operable to releasably secure the extension 50 within a desired position within the slot 54 (i.e., relative to the bracket 42).

Figures 2, 2A, 2B, 3:
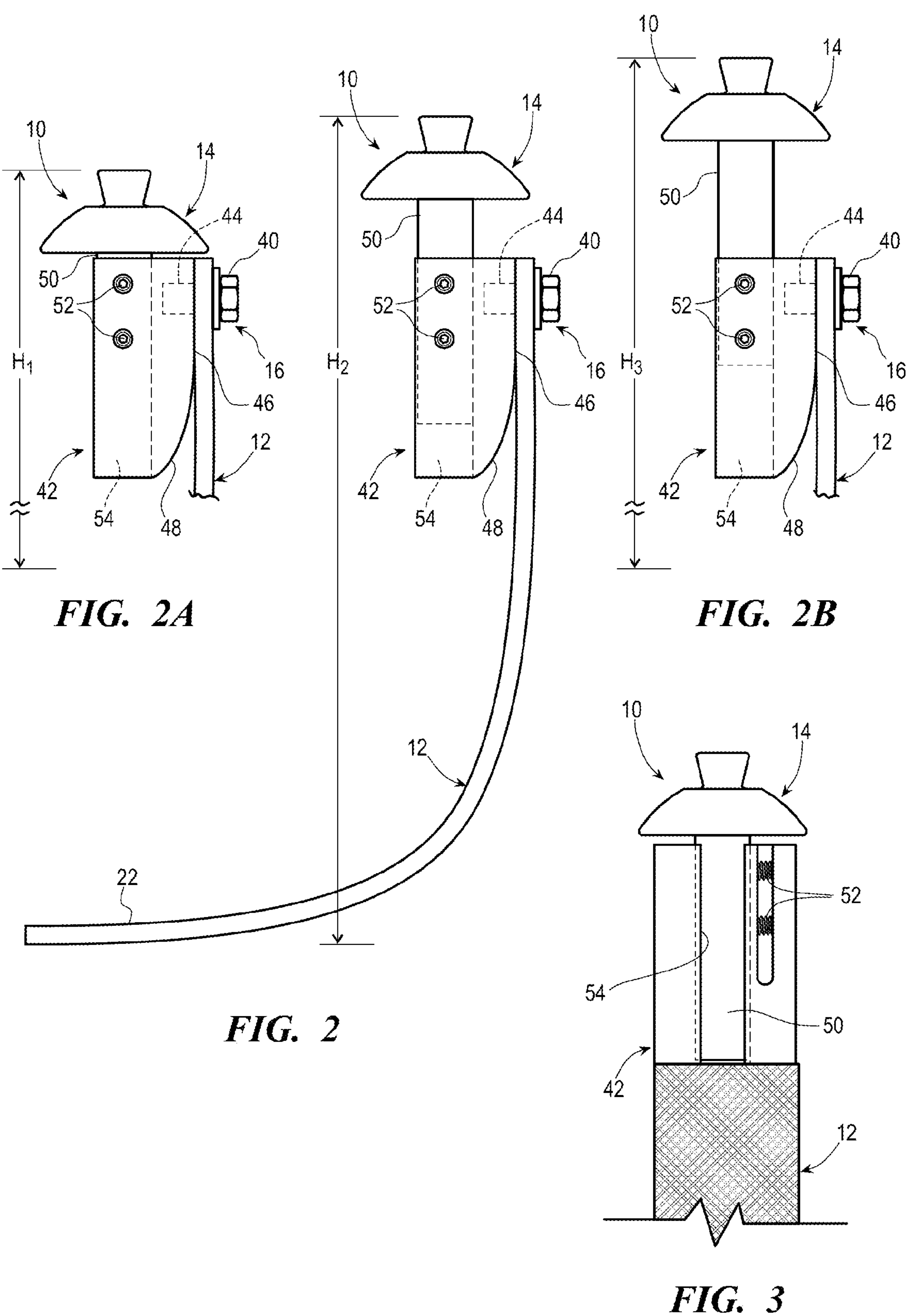
FIG. 2 is a side view of the prosthetic foot show in in FIG. 1 in an adjusted position.
FIGS. 2A and 2B show the prosthetic foot of FIGS. 1 and 2 in different adjusted positions.
FIG. 3 is a front view of a top portion of the prosthetic foot shown in FIG. 1.

Referring to FIGS. 2, 2A and 2B, the prosthetic foot 10 is shown with the adaptor 14 in different height-adjusted positions. FIG. 2A shows the adaptor 14 at a reduced height-adjusted position $H_1$. FIG. 2 shows the adaptor 14 in an intermediate height-adjusted position $H_2$. FIG. 2B shows the adaptor 14 in a maximum height-adjusted position $H_3$. In each of FIGS. 2, 2A and 2B, the extension 50 is shown in different positions relative to the slot 54 while the bracket 42 remains in a fixed position relative to the spring assembly 12 via connection by the fastener or fasteners 40. In the illustrated embodiment, the fastener 40 is illustrated as a single fastener. In alternative embodiments, the fastener 40 may include a plurality of fasteners located at equal height and aligned horizontally.

Figure 4A:
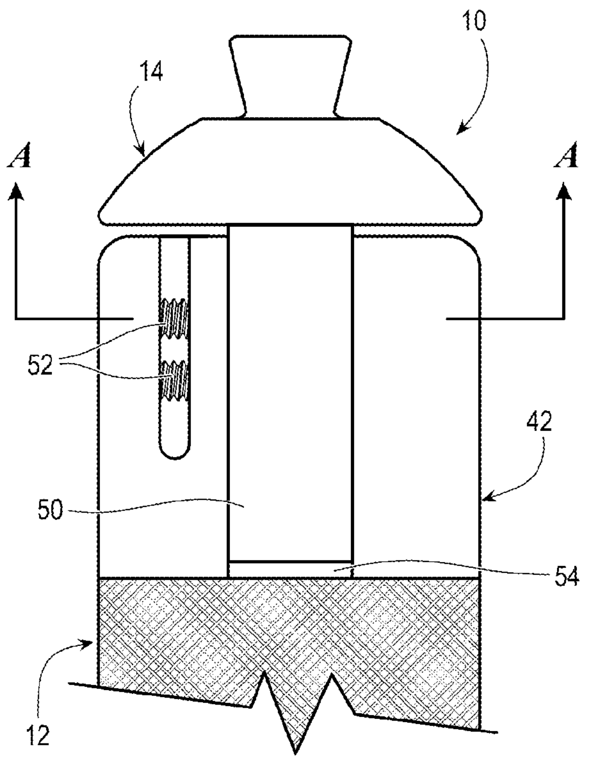
FIG. 4A is preview of a portion of another prosthetic device in accordance with the present disclosure.
Figure 4B:
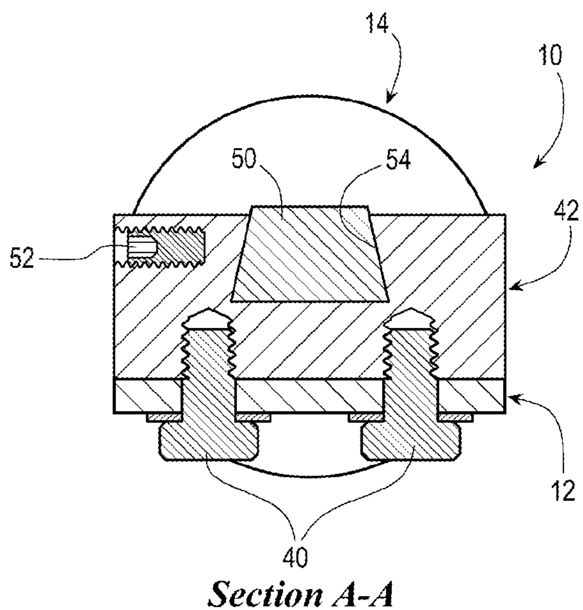
FIG. 4B is a cross-sectional view of the prosthetic foot shown in FIG. 4A taken along cross-section indicators A-A.

FIG. 3 is a front view of an upper or proximal portion of the prosthetic foot 10. FIG. 3 shows the slot 54 with the extension 50 positioned therein. The extension 50 may be retained within the slot 54, at least in the anterior/posterior and medial/lateral directions because of the interface, shape and size between the slot 54 and the extension 50. FIGS. 4A and 4B are additional views showing example shapes and sizes for these features. For example, FIG. 4B is a cross-sectional view of FIG. 4A taken along cross-section indicators A-A. The slot 54 and extension 50 have a dove-tailed type shape and mating interface. Other cross-sectional shapes and sizes are possible for the interface between the slot 54 and extension 50.

Generally, the embodiment of FIGS. 1-4B may be referred to as a dove-tail sliding mechanism that provides height adjustment capability for the prosthetic foot 10. The pyramid connector 30 may be connected to the top of the dove tail, which is secured in position via the set screw connection provided by the adjustment assembly 16.

The embodiment of FIGS. 1-4B also may include a contoured portion 48 of a surface 46 of the bracket 42 that interfaces with the surface of the spring assembly 12. During use of the prosthetic foot 10, the spring assembly 12 tends to flex, thereby bringing additional contact between the contoured portion 48 and a surface of the spring assembly 12. This gradual increase in contact between the surface 46 (i.e., including the contoured portion 48) and the spring assembly 12 may provide for a relatively smooth rollover during the gait cycle when the prosthetic foot is in use. The user may place her weight on the prosthetic foot 10 and the contoured surface of the pyramid connection device rolls onto the surface the spring assembly 12. This flexing of the spring assembly 12, which is controlled in part by the shape of the contoured portion 48, may provide the relatively smooth rollover function.

Figure 5A:
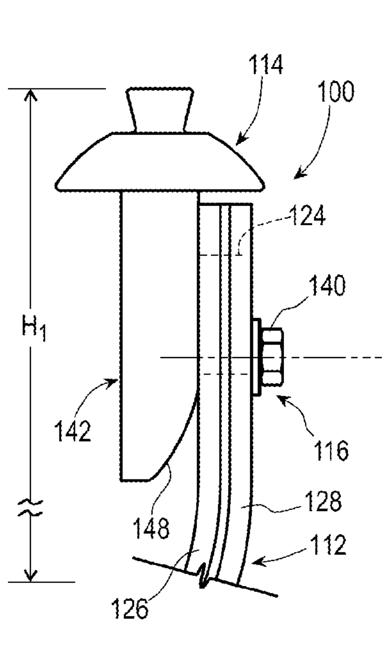
FIGS. 5A-5D show a side view of a portion of another prosthetic foot at different height-adjusted positions in accordance with the present disclosure.
Figure 5B:
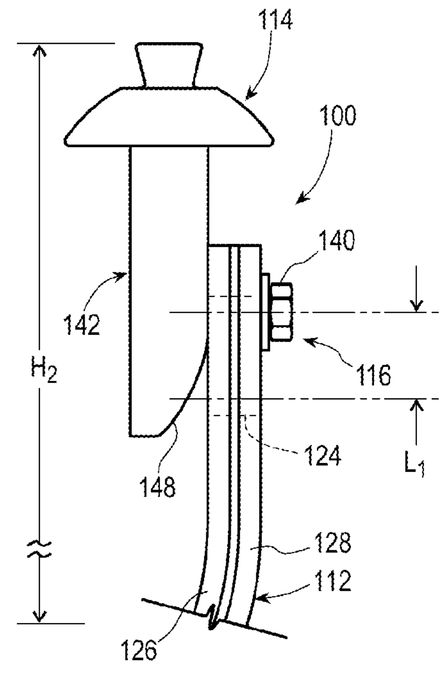

FIGS. 5A and 5B show an upper or proximal portion of another example prosthetic device in the form of prosthetic foot 100. The prosthetic foot 100 includes a spring assembly 112, an adaptor 114, and an adjustment assembly 116. The spring assembly 112 includes first and second spring members 126, 128 and a slot 124 formed in the spring members 126, 128. The adjustment assembly 116 includes a fastener 140 and bracket 142. The adaptor 114 is directly connected to the bracket 142. The bracket 142 includes a contoured surface 148 that provides smooth rollover functionality.

The fastener 140 extends through the slot 124 to provide a positive connection between the bracket 142 and the spring assembly 112. The fastener 140 may be moved vertically within the slot 124 to provide a vertical or height adjustment for the adaptor 114 relative to the spring assembly 112. FIG. 5A shows the adaptor at height $H_1$. FIG. 5B shows the adaptor 114 at an adjusted or increased height $H_2$.

Figure 5C:
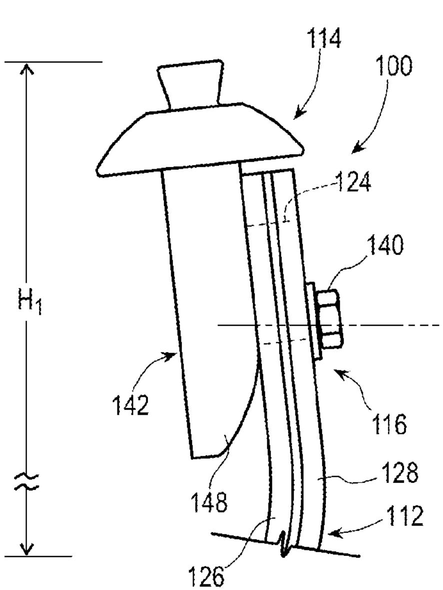
Figure 5D:
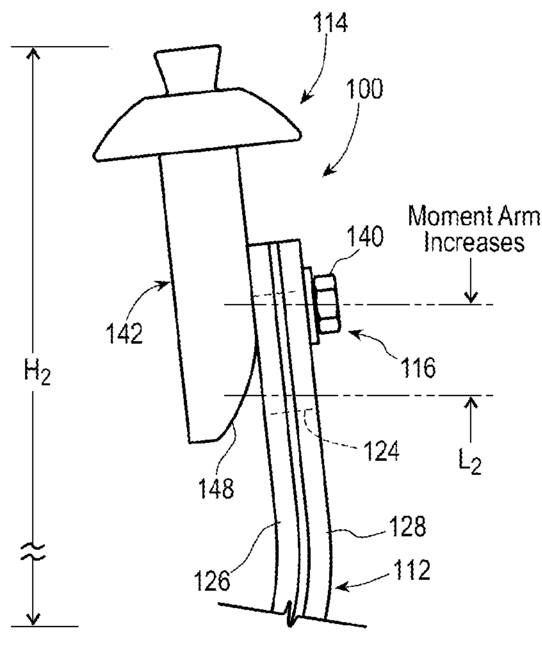

FIGS. 5C and 5D show the prosthetic foot 100 in use wherein the spring assembly 112 is flexed. This flexing of the spring assembly 112 provides increased contact between the contoured portion 148 of the bracket 142, thereby providing improved smoothness in rollover during use of the prosthetic foot 100. Further, adjusting the adaptor 114 from height $H_1$ to height $H_2$ increases the moment arm, thereby further increasing the amount of contact between the contoured portion 148 and the spring assembly 112. As the height of the adaptor 114 is increased, the torque and stiffness characteristics of the prosthetic foot 100 changes. As a result of these inherent characteristics, subtle changes to the contour of the surface 148 can be made, which may benefit the user. Providing height adjustment of the adaptor 114 may provide the ability to customize the characteristics of the prosthetic foot without having to provide an entirely new prosthetic foot that has a longer spring assembly (i.e., extends further in the proximal direction in order to achieve those characteristics).

Figures 6, 6A, 7:
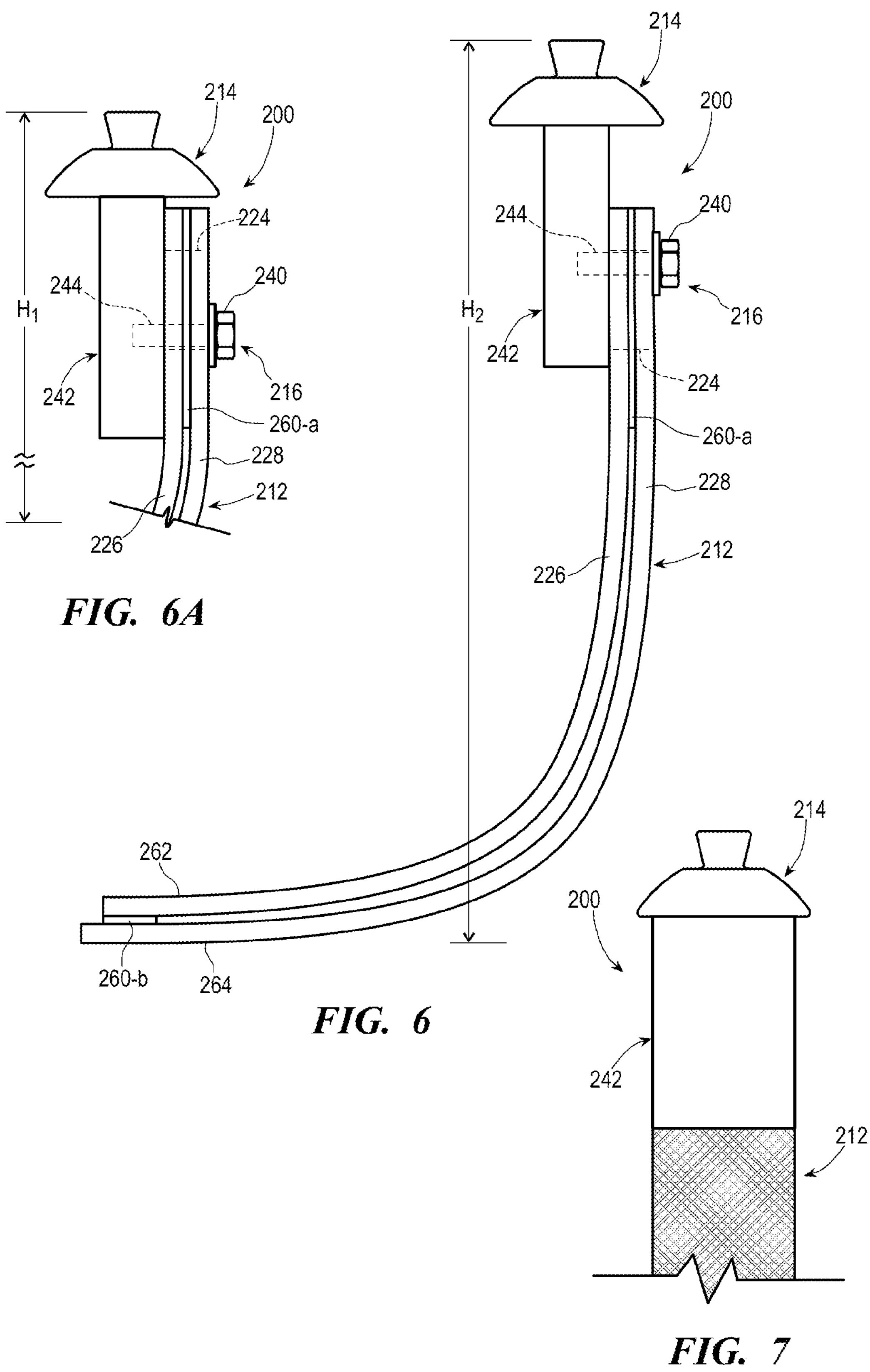
FIGS. 6 and 6A show a side view of another prosthetic foot in accordance with the present disclosure in different height-adjusted positions.
FIG. 7 is a front view of the prosthetic foot as shown in FIGS. 6-6A.

FIGS. 6 and 6A show another example prosthetic device in the form of a prosthetic foot 200. The prosthetic foot 200 includes a spring assembly 212, an adapter 214, and an adjustment assembly 216. The spring assembly includes top and bottom springs 226, 228 with a slot 224 formed therein at a proximal end thereof. The adjustment assembly 216 is mounted to a top or forward facing surface 262 of the top spring 226. The adjustment assembly 216 includes a fastener 240 and bracket 242 with an aperture 244 formed therein for a threadable engagement with the fastener 240. The fastener 240 is slidable within the slot 224 to provide an adjustment in height between the recessed or minimal height $H_1$ shown in FIG. 6A and the extended or maximum height $H_2$ shown in FIG. 6. FIG. 7 is a front view of the prosthetic foot 200.

Generally, the prosthetic foot 200 provides an adjustable adapter that is slidably clamped to the spring assembly 212. The adapter 214 connects to the front of the spring assembly 212. The spring assembly 212 is slotted such that the position of the adapter 214 can be adjusted higher or lower to accommodate the requirements of the user and the height of her prosthesis.

Figures 8, 8A, 9:
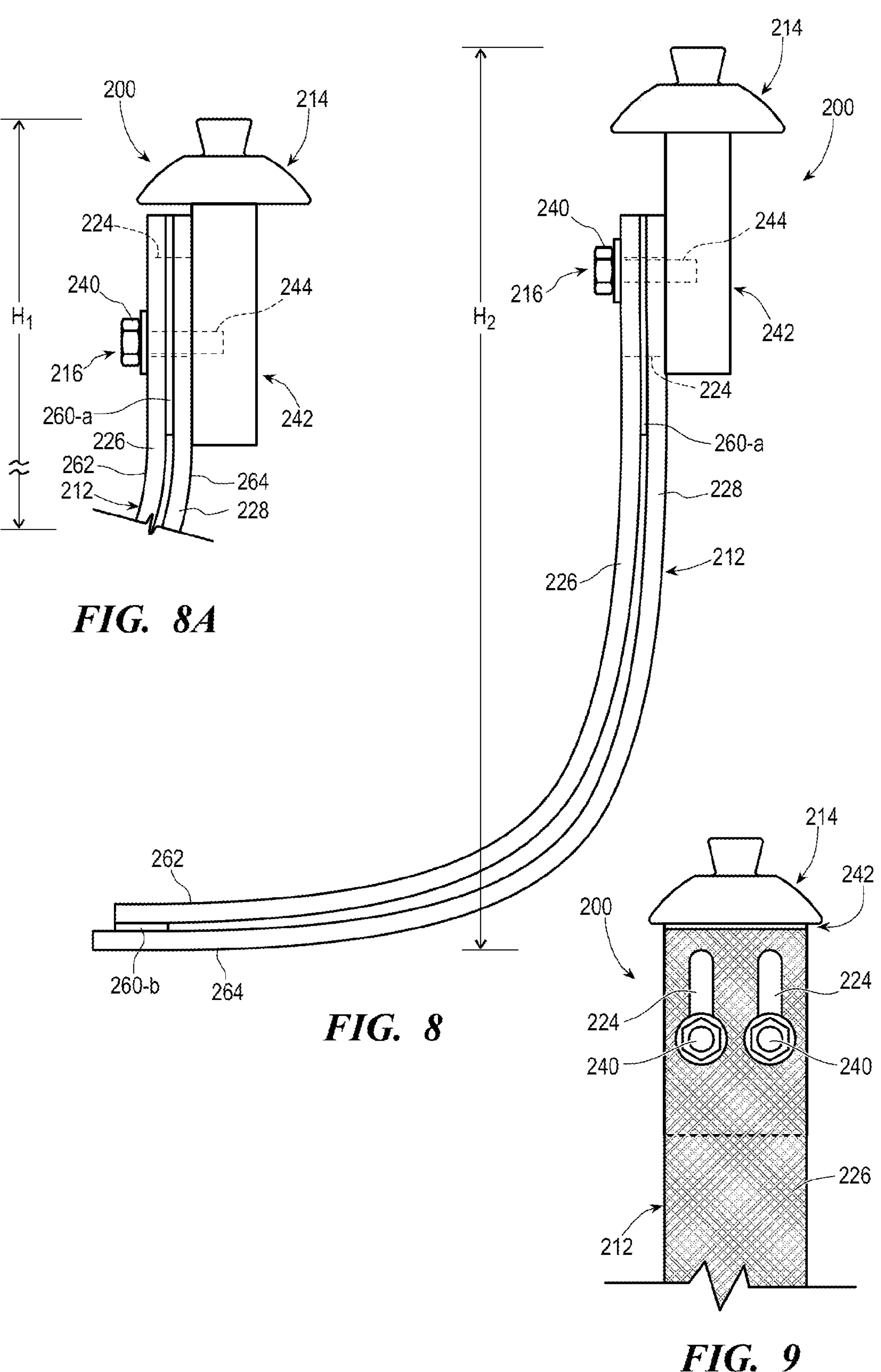
FIGS. 8 and 8A are side views of another prosthetic foot in accordance with the present disclosure and different height-adjusted positions.
FIG. 9 is a front view of the prosthetic foot shown in FIGS. 8-8A.

FIGS. 8 and 8A show another arrangement for the prosthetic foot 200 in which the adjustment assembly 216 with adapter 214 are mounted to a rear surface of the spring assembly 212, and specifically to a rear surface 264 of the bottom spring 228. The arrangement shown in FIGS. 8 and 8A may provide a similar height adjustment between heights $H_1$ and $H_2$, but with the adapter positioned further posterior or in a rearward direction relative to the spring assembly 212. FIG. 9 shows a front view of the prosthetic foot 200, including the slots 224 within which the fasteners 240 are slidable to provide the desired height adjustment for the adapter 214.

Figures 10, 10A, 11:
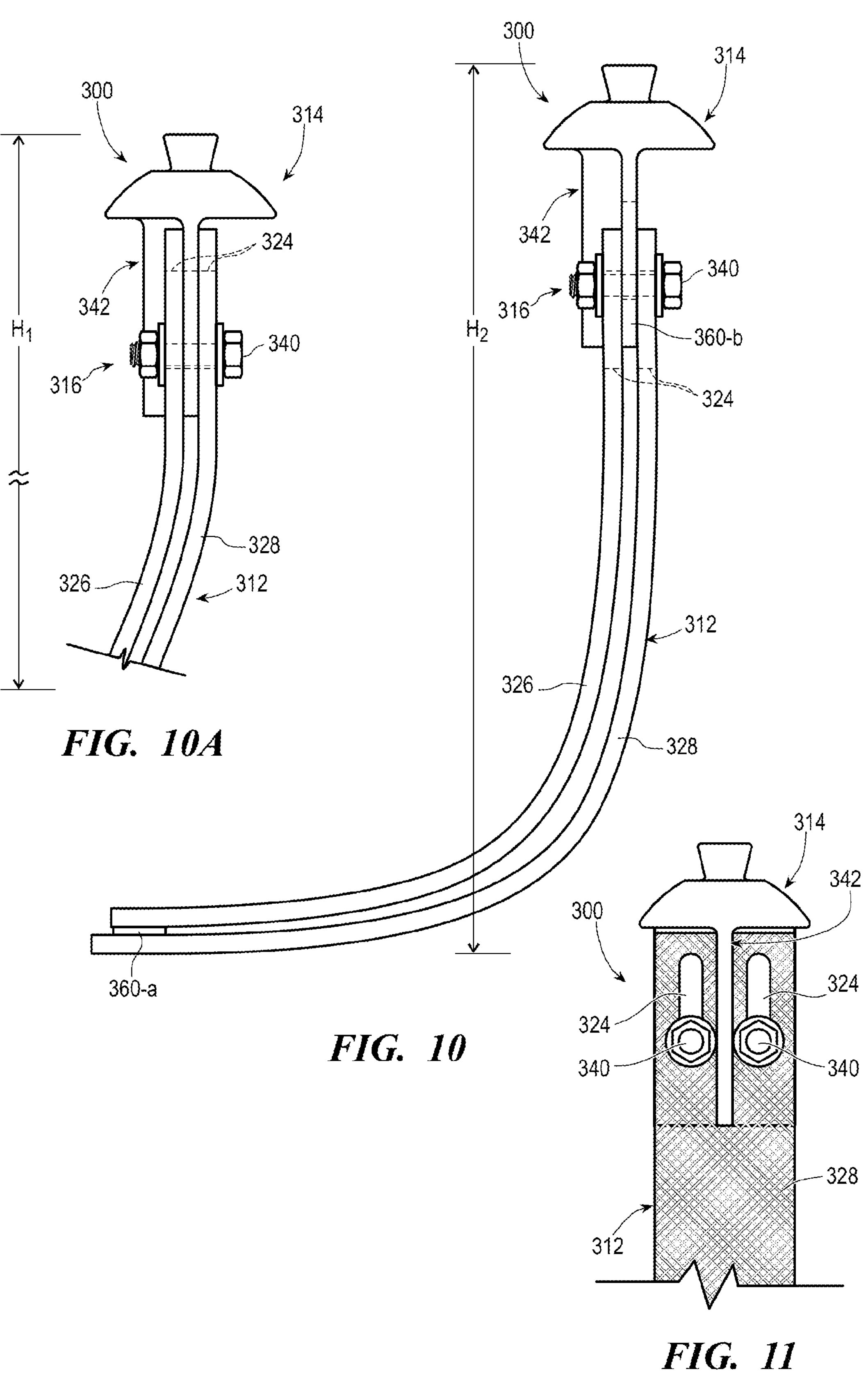
FIGS. 10 and 10A show a side view of another prosthetic foot in accordance with the present disclosure in different height-adjusted positions.
FIG. 11 is a rear view of the prosthetic foot shown in FIGS. 10-10A.

FIGS. 10 and 10A are side views of another example prosthetic device in the form of a prosthetic foot 300. The prosthetic foot 300 includes a spring assembly 312, an adapter 314, and an adjustment assembly 316. The spring assembly includes top and bottom springs 326, 328 with slots 324 formed therein as shown in at least FIG. 11. A portion of the bracket 342 is positioned between the top and bottom springs 326, 328. Another portion of the bracket 342 may extend along a side surface of the spring assembly 312.

Generally, the prosthetic foot 300 may provide the adapter 314 with a slidable connection to the interior of the spring assembly 312. In this embodiment, the top and bottom springs 326, 328 are independent springs that are not attached to each other, at least at the proximal end of the spring assembly 312. The adapter 314 may be adjusted by sliding to a higher or lower position by moving the fastener 340 within the slot 324 of the springs 326, 328. The bracket 342 may include a rib or other structure that slides into the gap between the springs 326, 328.

Figure 12A:
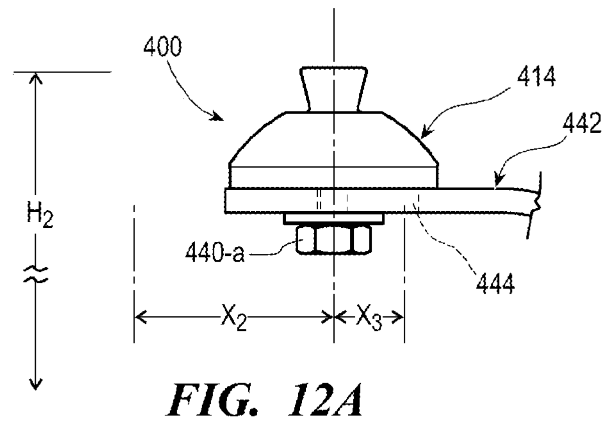
FIGS. 12 and 12A are side views of another prosthetic foot in accordance with the present disclosure in different adjusted positions for the adaptor in a horizontal direction.
Figure 12:
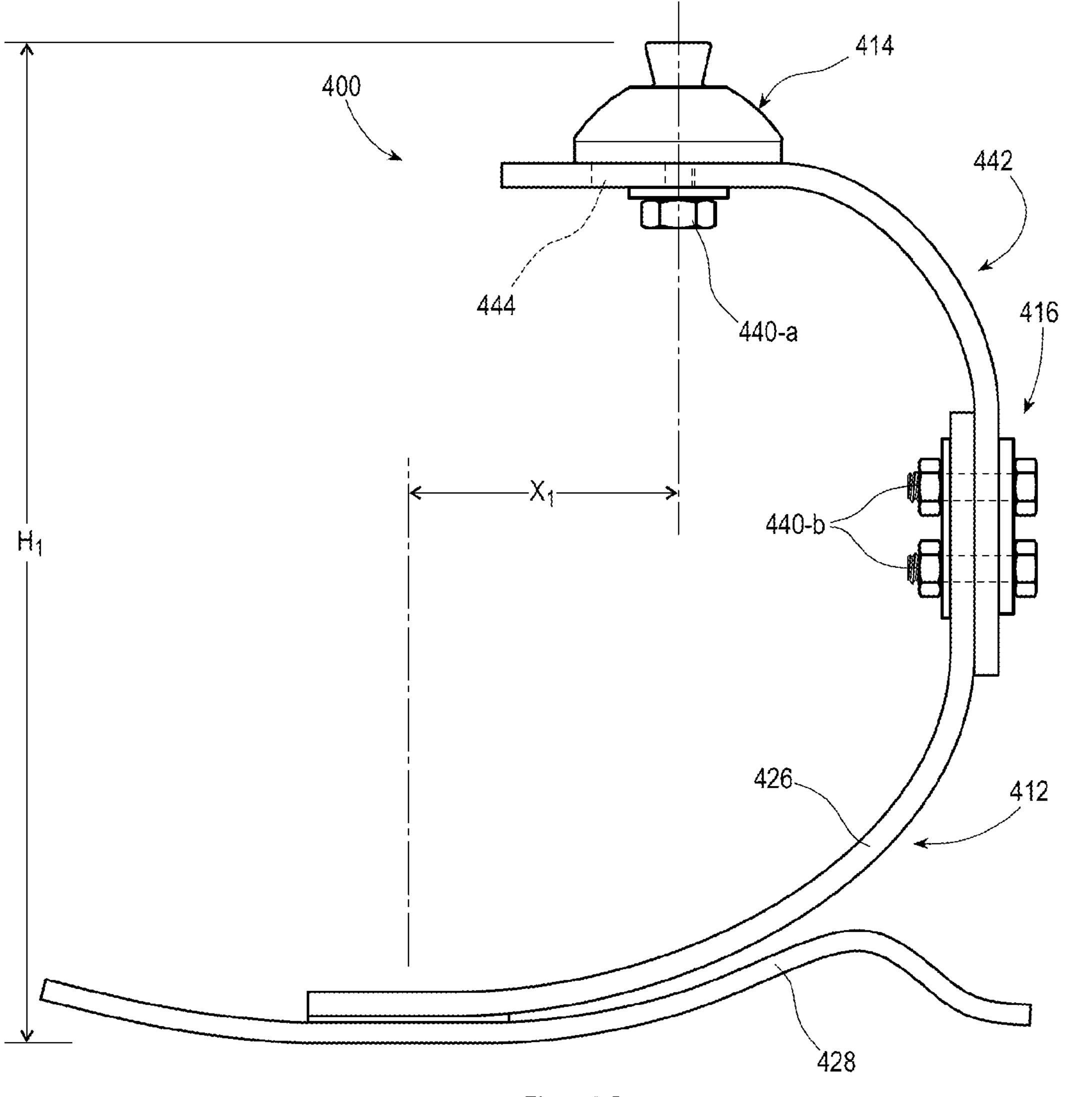

FIGS. 12 and 12A show another example prosthetic device in the form of a prosthetic foot 400. The prosthetic foot 400 includes a spring assembly 412, an adapter 414, and an adjustment assembly 416. The adjustment assembly 416 includes a bracket 442 having a slot 444 formed therein at or near the proximal end thereof. The bracket 442 is secured to the adapter 414 with a fastener 440-*a*. The bracket 442 is mounted to the spring assembly 412 with one or more additional fasteners 440-*b*. The spring assembly 412 may include top and bottom springs 426, 428. The bracket 442 may be mounted to a proximal or upper end of the top spring 426.

The prosthetic foot 400 may provide for movement or adjustability of the adapter 414 relative to the spring assembly 412 by sliding the fastener 440-*a* within the slot 444. FIG. 12 shows the adapter 414 in a first or posterior most position $X_1$. FIG. 12A shows the adapter 414 in a forward or anterior most position $X_2$. The difference between the positions $X_1$ and $X_2$ may be a total adjusted position of $X_3$. The connection between the bracket 442 and the spring assembly 412 may be a fixed connection without any adjustability in any direction. Alternatively, the connection between the bracket 442 and spring assembly 412 may be adjustable.

FIGS. 13 and 13A show another example prosthetic device in the form of a prosthetic foot 500 that provides adjustability between an adapter 514 and an adjustment assembly 516, and between the adjustment assembly 516 and a spring assembly 512. The spring assembly 512 includes first and second springs 526, 528. The adjustment assembly 516 includes a first fastener 540-*a* that is movable within a slot 554 to provide horizontal (also referred to as anterior/posterior) adjustment of the adapter 514 relative to the spring assembly 512. The adjustment assembly 516 also includes fasteners 540-*b* that provide a connection between the adjustment assembly 516 and the spring assembly 512. The first spring 526 may include a slot 524 within which the fasteners 540-*b* are slidable to provide a height adjustment of the adapter 514 relative to the spring assembly 512. Alternatively, the bracket 542 may include a slot through which the fasteners 540-*b* are slidable to provide a similar height adjustment function.

FIG. 14A shows a cross-sectional view of the prosthetic foot 500 taken along cross-section indicators A-A, and illustrates the slot 554 with the fastener 540-*a* slidable therein. FIG. 14B shows a cross-sectional view of the prosthetic foot 500 taken along cross-section indicators B-B showing the slot 524 with the fasteners 540-*b* slidable therein to provide the desired height adjustment.

In the embodiments of FIGS. 12-13, the adjustment assembly may be secured to a posterior or anterior surface of the first spring. Further, the adapter 514 may be positioned at any desired location along a length of the bracket, including along a curved portion of the bracket, wherein adjustment of the adapter relative to the bracket may provide a change in both a posterior/anterior direction as well as a distal/proximal direction.

Furthermore, the brackets 442, 542 may be referred to as intermediate spring element or a proximal spring element, and has spring characteristics.

Figures 15, 15A:
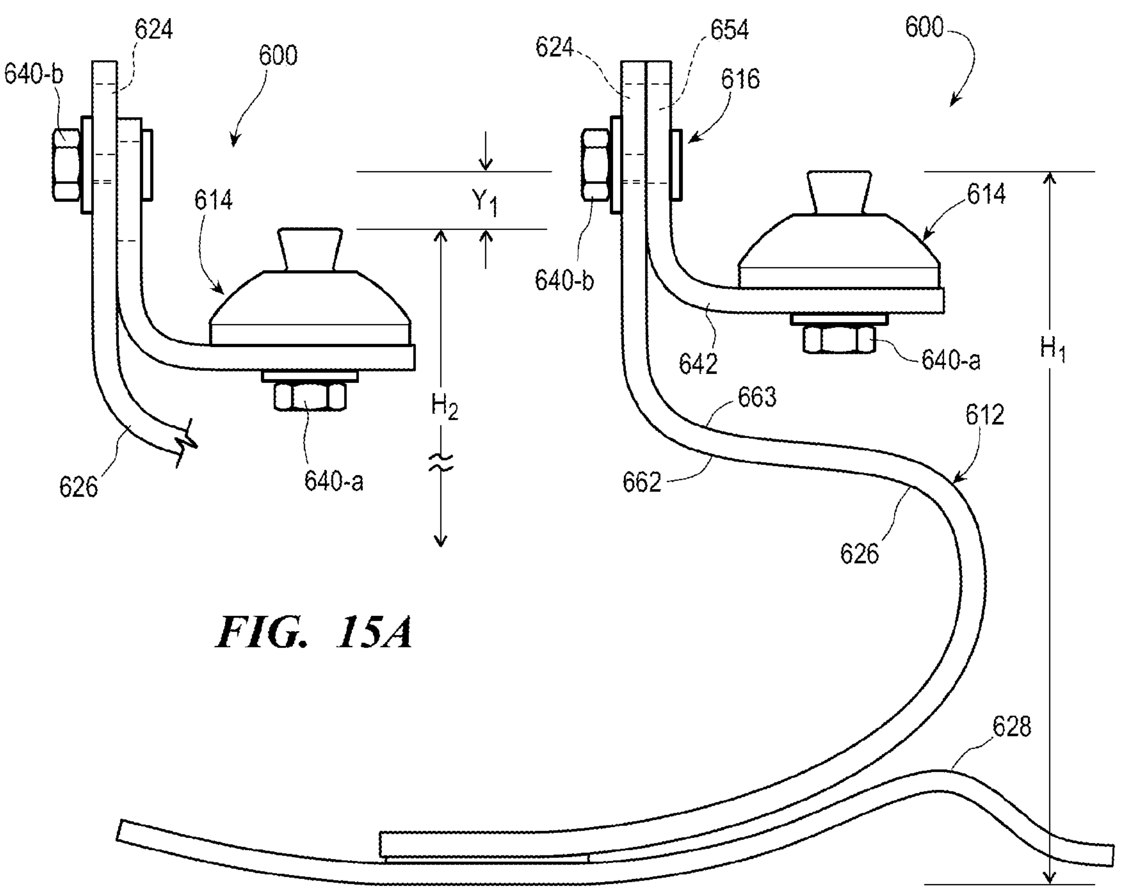
FIGS. 15 and 15A are side views of another example prosthetic foot in accordance with the present disclosure in different height-adjusted positions.

FIGS. 15 and 15A show another prosthetic device in the form of a prosthetic foot 600 having a spring assembly 612, an adapter 614, and an adjustment assembly 616. The spring assembly 612 includes first and second spring members 626, 628. The adjustment assembly 616 includes a bracket 642, a fastener 640-*a* that secures the adapter 614 to the bracket 642, and a fastener 640-*b* that secures the bracket 642 to the first spring 626. The bracket 642 may be mounted to a posterior surface 663 of the first spring 626. In other arrangements, the bracket 642 may be reversed so as to mount to a front surface 662 of the first spring 626.

The first spring 626 may include a slot 624, and the fastener 640-*b* may be slidable within the slot 624 to provide a height adjustment of the adapter 614 relative to the spring assembly 612. The sliding adjustment of the fastener 640-*b* within the slot 624 may provide a height adjustment from a maximum $H_1$ shown in FIG. 15, to a minimum $H_2$ shown in FIG. 15A. In other arrangements, the bracket 642 may also include a slot (not shown) within which the fastener 640-*a* is slidable to provide adjustment of the adapter 614 in a horizontal and/or anterior/posterior direction.

The first spring 626 is an elongate spring extending from forefoot or toe location and extending in a posterior direction to an upwardly curving ankle portion, further extending upward and curving in an anterior direction and achieving a tangent angle within 45 degrees of horizontal at an inflection point in the curvature, further curving and extending to a vertical or near vertical connecting portion.

Generally, the bracket 642 may be referred to as an L-shaped spring or bracket to which the adapter 614 is mounted. The adapter 614 may be slidably connected to the bracket 642 in the anterior/posterior direction. The height of the adapter 614 may be adjustable via one or more side-by-side fasteners 640-*b* and slots 624. The pylon shape of the spring 626 may have a variety of different shapes and sizes to provide desired functionality. The increased length of the first spring 626 makes it possible to provide an increased thickness for the spring 626, which may result in stronger structure while still providing desired deflection as compared to a shorter, thinner and weaker spring. The shape of spring 626 may also provide a higher degree of vertical flexibility due to the horizontal orientation of the intermediate portion of the spring 626 along its length.

Figures 16, 16A:
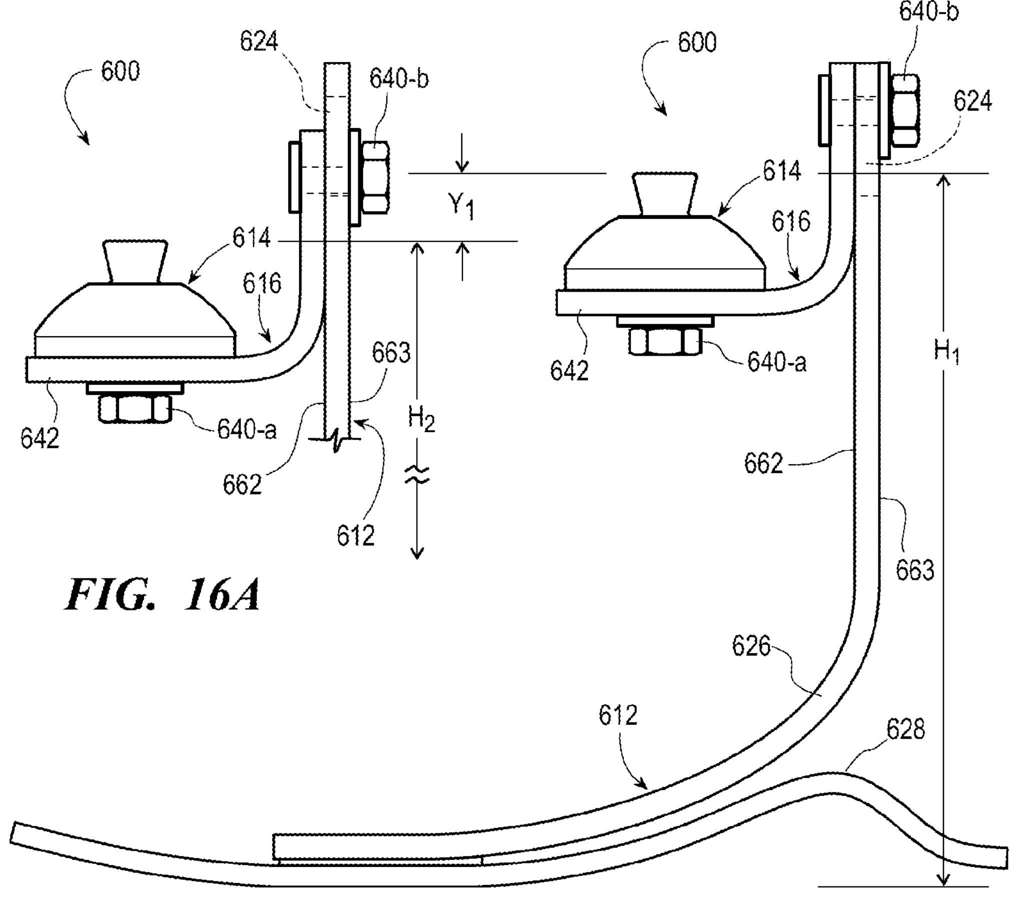
FIGS. 16 and 16A are side views of another prosthetic foot in accordance with the present disclosure in different height-adjusted positions.

FIGS. 16 and 16A show the prosthetic foot with the adjustment assembly 616 reversed so as to be positioned along the anterior surface 662 of the first spring 626. The first spring 626 may have a relatively simple curvature as compared to what is shown in FIGS. 15 and 15A. Alternatively, the spring 626 may have the more complex shape shown in FIGS. 15-15A. A slot 654 and the bracket 642 may alternatively provide the vertical adjustment.

The design of the bracket 642 shown in FIGS. 15-16A wherein the adapter is dropped below the proximal end of the spring assembly may provide a variety of advantages including, for example, that the first spring 626 may be longer and/or taller, extending further in the proximal direction, which has at least those advantages described above related to the greater length of the first spring member 626.

Figures 17, 17A, 18, 19:
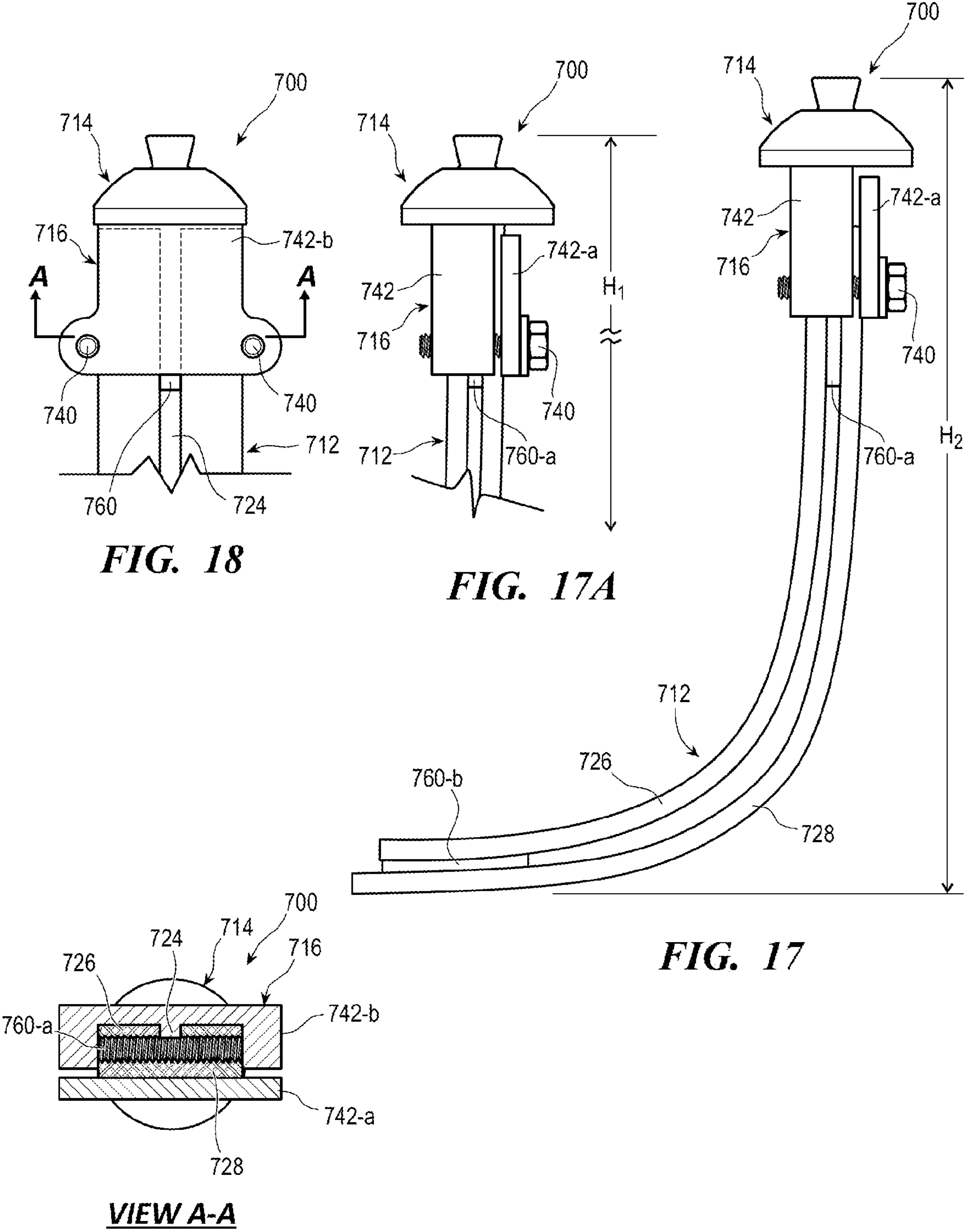
FIGS. 17 and 17A are side views of another example prosthetic device in accordance with the present disclosure and different height-adjusted positions.
FIG. 18 is a front view of the prosthetic foot shown in FIGS. 17-17A.
FIG. 19 is a cross-sectional view of the prosthetic foot shown in FIG. 18 taken along cross-section indicators A-A.

FIGS. 17 and 17A show another example prosthetic device in the form of a prosthetic foot 700. The prosthetic foot 700 includes a spring assembly 712, an adapter 714, and an adjustment assembly 716. The spring assembly 712 includes first and second spring members 726, 728 that are arranged in parallel with each other with spacers 760-*a*, 760-*b* positioned therebetween at proximal and distal ends thereof. The adjustment assembly 716 includes first and second brackets 742-*a*, 742-*b*. A fastener 740 extends through both of the brackets 742-*a*-*b* to sandwich the spring assembly 712 therebetween. The adjustment assembly 716 provides for height adjustment of the adapter 714 from a minimum $H_1$ shown in FIG. 17A to a maximum $H_2$ shown in FIG. 17.

FIG. 19 is a cross-sectional view of the prosthetic foot 700 shown in FIG. 18 taken along cross-section indicators A-A. The spring assembly 712 includes a slot 724 formed therein as shown in FIGS. 18 and 19. The fasteners 740 are positioned outside of the boundaries of the springs 726, 728, and the bracket 742-*b* includes a follower portion that rides along the slot 724 of the first spring 726. Either of the brackets 742-*a*, 742-*b* ride within slots formed in either one of the springs 726, 728. Alternatively, one or more of the fasteners 740 may extend through one or both of the spring members 726, 728 and/or spacer 760-*a*, or slots formed therein. Slot 724 may include a center vertical flange 723 which forms the slot 724. The slot 724 may allow for alignment of the spring members 726. The spring members 726 and 728 may have a slot at the proximal end, or alternatively the spring members 726 and 728 may each be split into 2 separate springs located side-by-side, and the spacers 760-*a* and 760-*b* may also be split into two side-by-side components. In the split embodiment, the center vertical alignment flange 723 in bracket 742-*b* may be the same depth as the sides of the slot 724 to provide for vertical alignment of the side-by-side spring members and the spacer 760-*a*.

The prosthetic foot 700 may provide for an adapter 714 that is slidably connected to the spring assembly 712. The adjustment assembly 716 is secured external to the spring assembly 712. This embodiment could be further configured with a guide pin (not shown) that may be guided by the slot formed in one or more of the spring members 726, 728. The spring assembly 712 may or may not include the spacer 760-*a*.

Figures 20, 20A, 21:
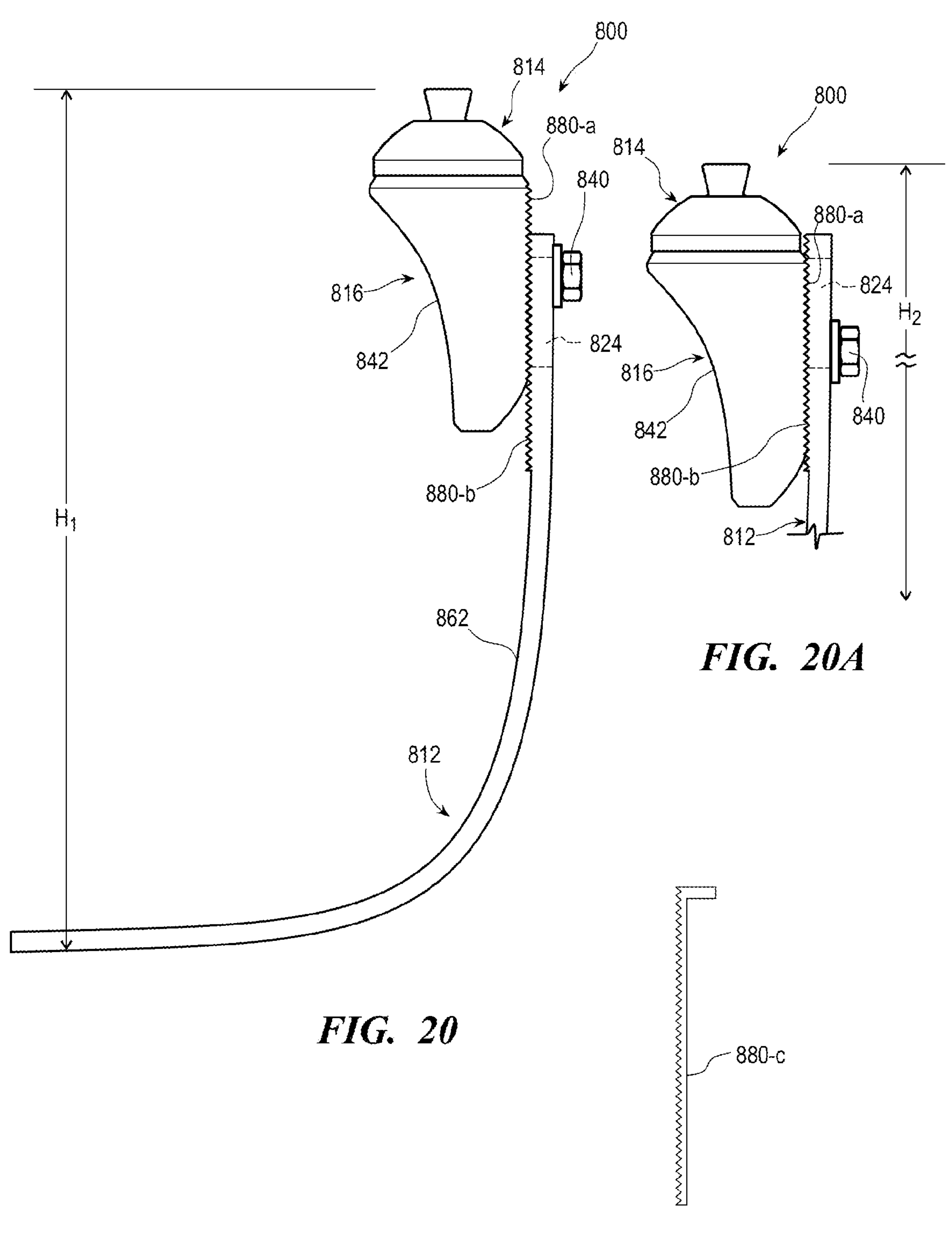
FIGS. 20 and 20A are side views of another example of another example prosthetic device in accordance with the present disclosure in different height-adjusted positions.
FIG. 21 is a side view of an example position-oriented set of tines for use in the prosthetic device of FIGS. 20-20A.

FIGS. 20 and 20A show another prosthetic device in the form of a prosthetic foot 800. The prosthetic foot 800 includes a spring assembly 812, an adapter 814, and an adjustment assembly 816. The adjustment assembly 816 includes a bracket 842 that is secured to the spring assembly 812 with a fastener 840. The spring assembly 812 may include a set of tines or teeth 880-*b* along a top or anterior-facing surface 862 that mates with a set of tines 880-*a* that are positioned along a posterior surface of the bracket 842. The mating tines 880-*a*-*b* provide for incremental height adjustment that may be more controlled or specific.

The spring assembly 812 may include a slot 824 formed therein. The fastener 840 may slide vertically within the slot 824 to provide the height adjustment of the adapter 814 relative to the spring assembly 812. FIG. 20 shows one height $H_1$ for the adapter 814. FIG. 20A shows a reduced height $H_2$ for the adapter 814 relative to the spring assembly 812.

FIG. 21 shows a tine member 880-*c* that is provided as a separate component that may be mounted to one or both of the spring assembly 812 and bracket 842. The tine member 880-*c* may have tines of different shapes and sizes that provide different incremental changes in the height.

The prosthetic foot 800 may provide for increased resistance to vertical forces due to the mating tines 880-*a*-*b*. Furthermore, the tines 880-*a*-*b* may provide for indexed or discrete vertical positions when adjusting the adapter 814 relative to the spring assembly 812. The tined surfaces 880-*a*-*b* may be fabricated by, for example, bonding a bent, toothed component onto the vertical or proximal portion of the spring assembly 812. In at least one example, the tines may be formed using a malleable metal such as aluminum, stainless steel or a thermoplastic material which is injection-molded or extruded and may be fiber reinforced such as EMS Grivory GV-4H®.

The separate tined component 880-*c* that includes tined features may be secured to the spring assembly 812 and/or bracket 842 using, for example, a bonding agent, fasteners, welding, or the like.

Figures 22, 23:
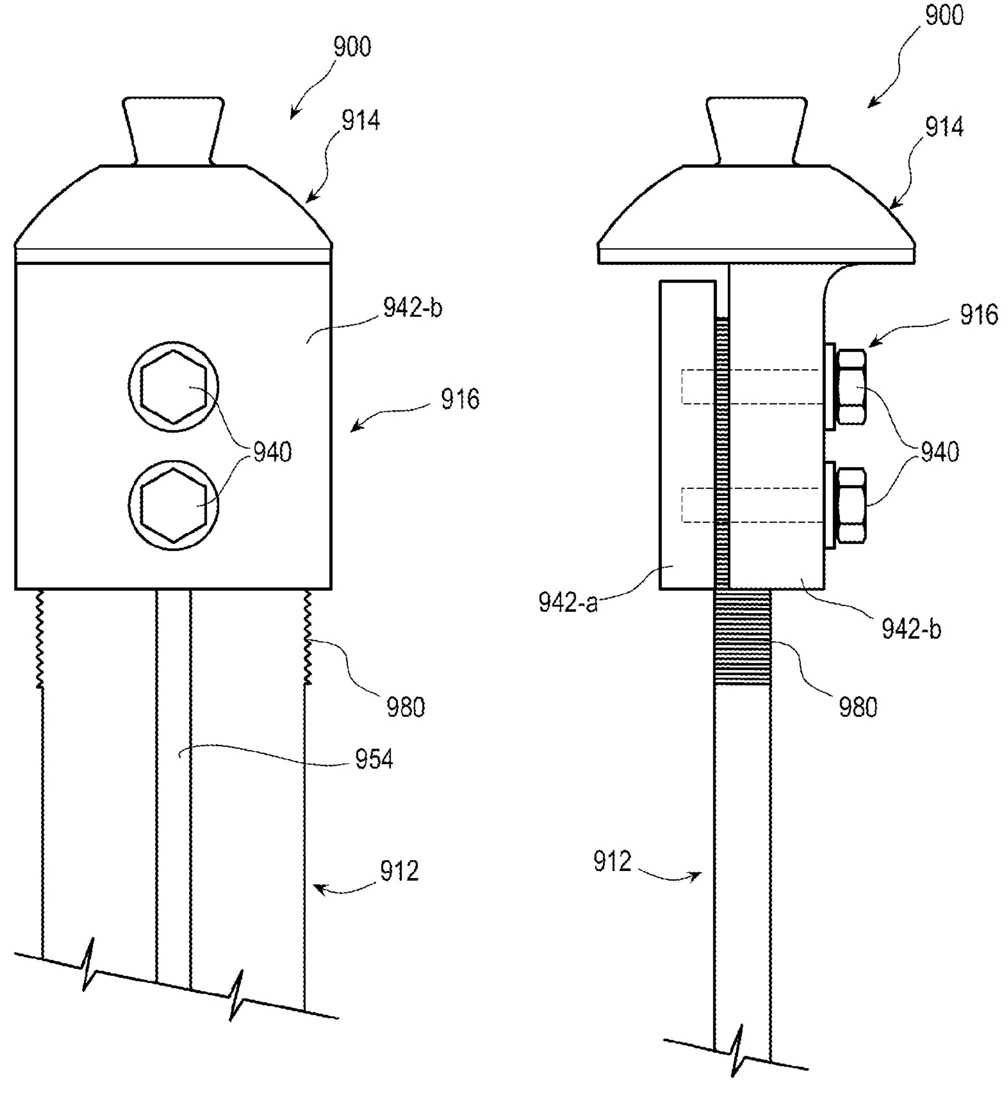
FIG. 22 is a side view of a portion of another example prosthetic device in accordance with the present disclosure having height adjustment features.
FIG. 23 is a rear view of the prosthetic device shown in FIG. 22.

FIGS. 22 and 23 show a prosthetic device in the form of a prosthetic foot 900. The prosthetic foot 900 includes a spring assembly 912, an adapter 914, and an adjustment assembly 916. The adjustment assembly 916 includes first and second brackets 942-*a*, 942-*b*. The brackets 942-*a*-*b* are secured together with fasteners 940 that extend through the spring assembly 912.

The spring assembly 912 may include a plurality of tines or serrated features 980 positioned along side edges thereof, wherein the side edges are arranged facing in the medial and lateral directions. The bracket 942-*b* may wrap around the side surfaces of the spring and include mating tine or other serrated features that engage with the tines 980. These mating tines on the bracket 942-*b* and the spring 912 may provide for indexed or discrete vertical positions for the adapter 914 relative to the spring assembly 912.

The spring assembly 912 may also include a slot 954 within which the fasteners 940 are slidably adjustable to provide the vertical adjustment of the adapter 914 relative to the spring assembly 912. As with other of the embodiments disclosed herein, the adjustment assembly 916 may include a single fastener 940 or two or more fasteners 940. The spring assembly 912 may include a single slot or may include a plurality of side-by-side slots within which the fasteners are slidably movable to provide the height adjustment for the adapter 914 relative to the spring assembly 912.

Figures 24, 25:
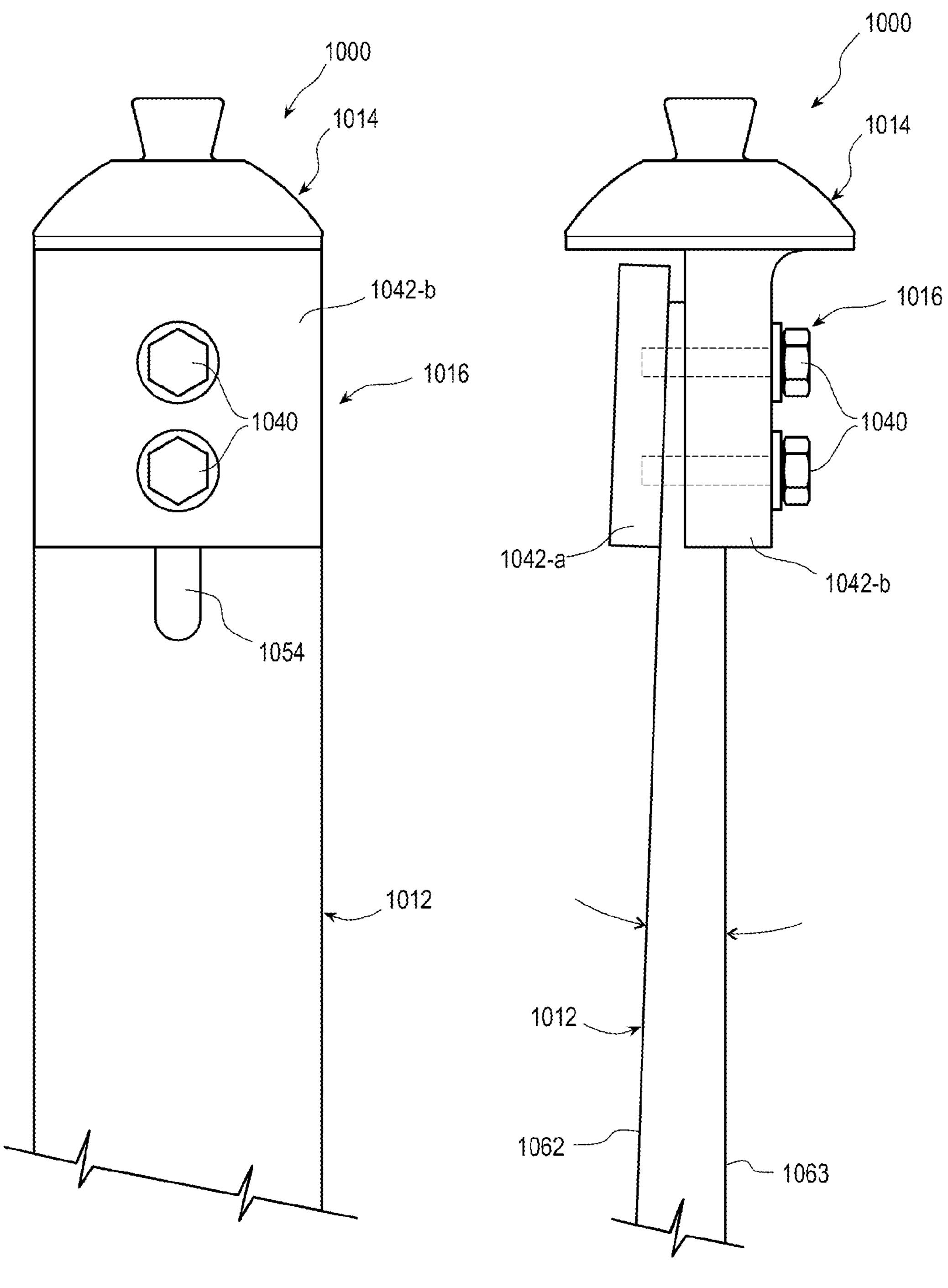
FIG. 24 is a side view of a portion of another prosthetic device having height adjustment features in accordance with the present disclosure.
FIG. 25 is a rear view of the prosthetic foot shown in FIG. 24.
Figure 26:
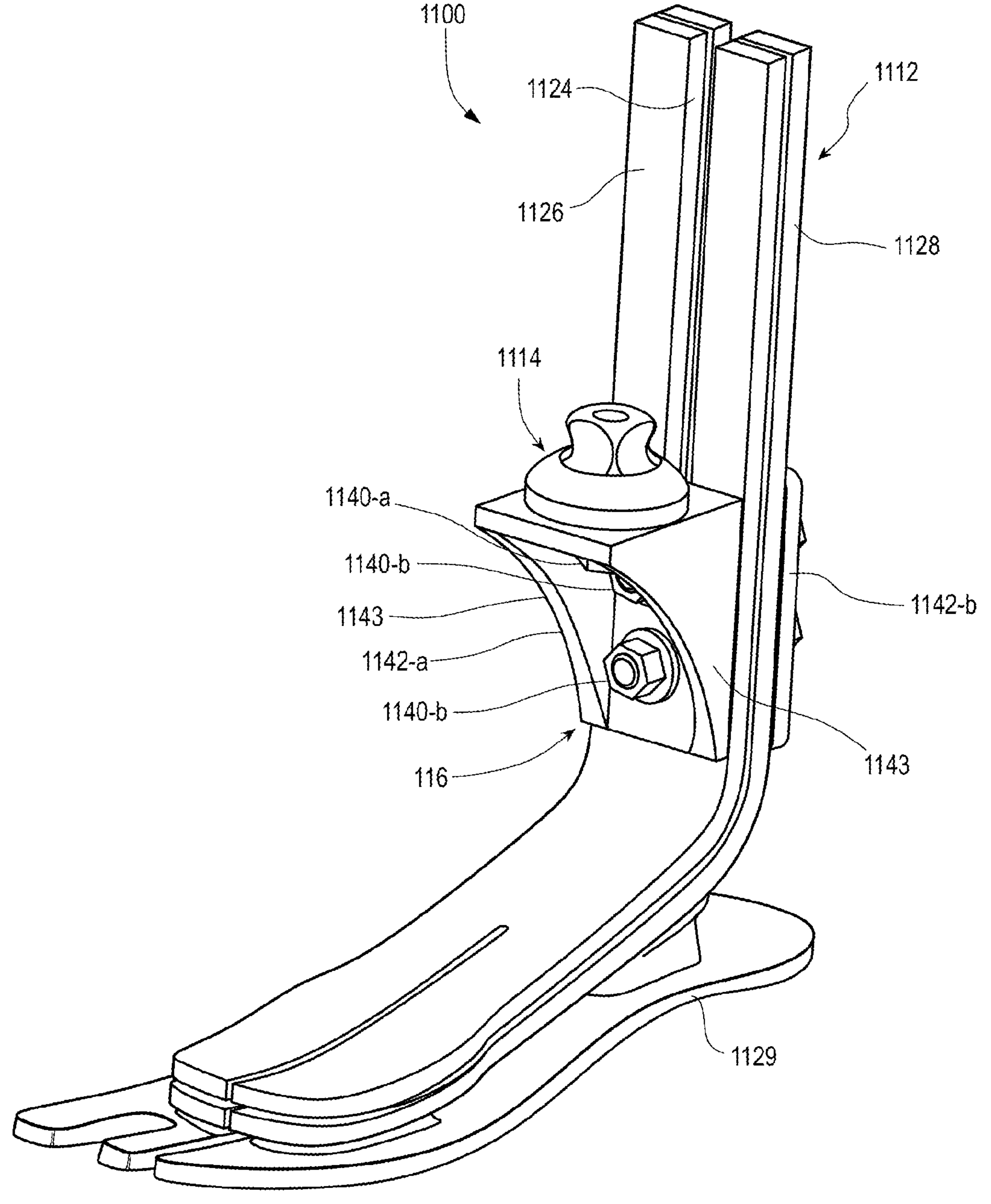
FIG. 26 is a perspective view of another example prosthetic device having height adjustment features in accordance with the present disclosure.

FIGS. 24 and 25 show side and rear views of a prosthetic device in the form of a prosthetic foot 1000. The prosthetic foot 1000 includes a spring assembly 1012, an adapter 1014, and an adjustment assembly 1016. The adjustment assembly 1016 includes fasteners 1040 and first and second brackets 1042-*a* and 1042-*b*. The bracket 1042-*b* may wrap around side edges of the spring assembly 1012. The spring assembly 1012 may include a slot 1054 (see FIG. 25) within which the fasteners 1040 are slidable to provide the desired height adjustment of the adapter 1014 relative to the spring assembly 1012.

The spring assembly 1012 may include anterior and posterior surfaces 1062, 1063 that are converging towards the proximal end of the spring assembly 1012. The spring assembly 1012 may be referred to as a tapered spring wherein a thickness of the spring is increasing or decreasing along its length. Alternatively, a width of the spring may be increasing or decreasing along its length. The taper may help control vertical forces applied from the adapter 1014 to the spring 1012. The tapered shape of the spring 1012 may create a wedge effect that helps ensure that the adjustment assembly 1016 does not slip out of the adjusted vertical position. Providing separate fasteners 1040 spaced apart in the vertical direction can help provide the desired compression force between the bracket members 1042-*a*-*b* to provide this wedge effect that helps eliminate vertical slipping relative to the spring 1012.

FIGS. 26-28A show another example prosthetic device in the form of a prosthetic foot 1100. The prosthetic foot 1100 includes a spring assembly 1112, an adapter 1114, and an adjustment assembly 1116. The spring assembly 1112 includes first and second top spring members 1126, 1128 and a bottom spring member 1129. A slot 1124 may be formed in the spring members 1126, 1128 to provide for a vertical sliding adjustment of the adjustment assembly 1116 relative to the spring assembly 1112. A dual upper pylon spring assembly 1112 utilizing springs 1126 and 1128 as shown in this embodiment may provide enhanced foot function. Utilizing a single upper pylon 1128 may result in improved height adjustment simplicity.

The adjustment assembly 1116 includes a bracket 1142-*a* position along an anterior side of the spring assembly 1112, and a bracket 1142-*b* position along a posterior side of the spring assembly 1112. A first fastener 1140-*a* secures the adapter 1114 to the first bracket 1142-*a*. One or more second fasteners 1140-*b* secures the brackets 1142-*a*-*b* to each other. Fasteners 1140-*b* are positioned within the slot 1152 to provide a positive connection of the adjustment assembly 1116 to the spring assembly 1112.

Figure 27:
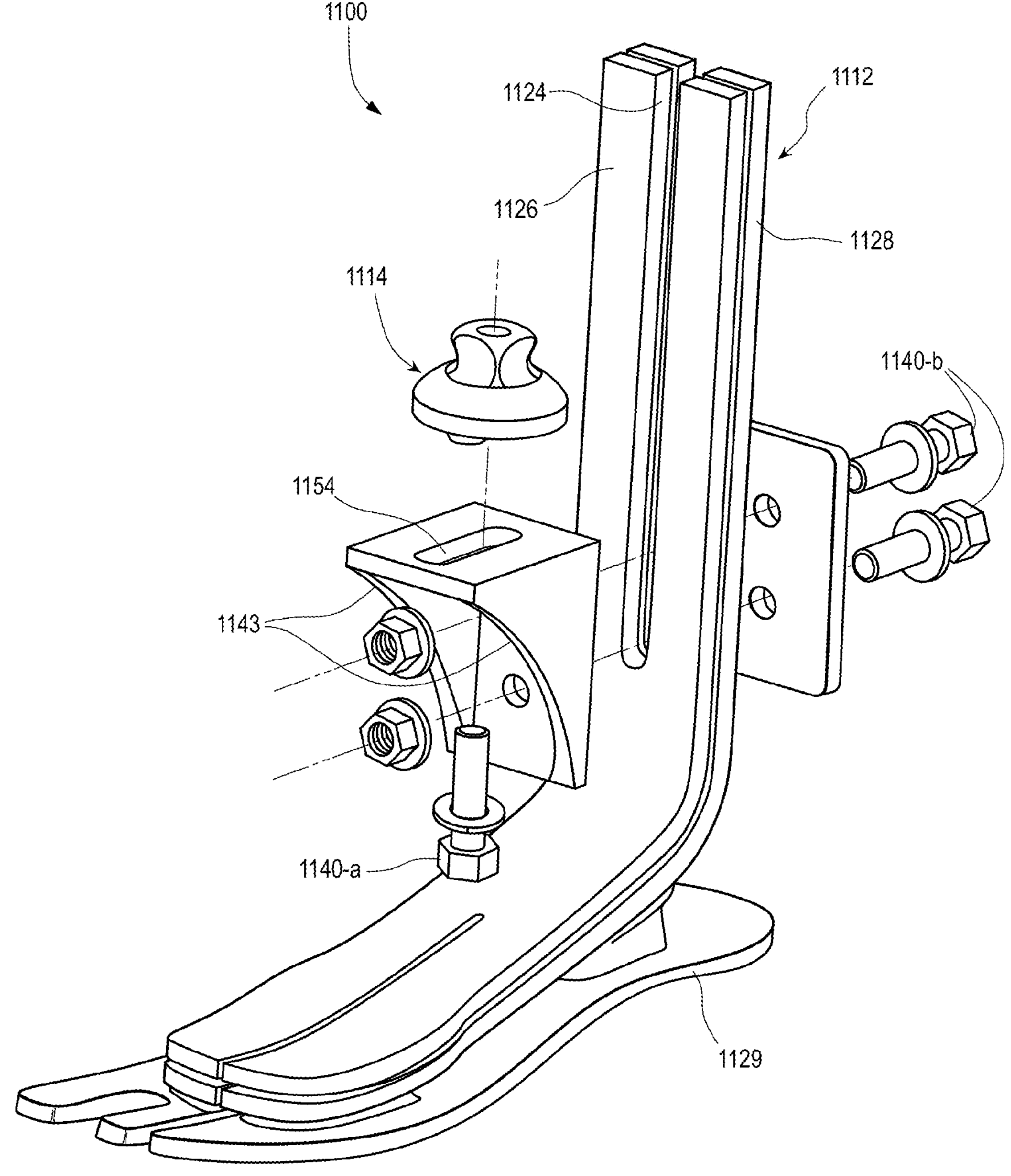
FIG. 27 is a partial-exploded view of the prosthetic device shown in FIG. 26.
Figures 28, 28A:
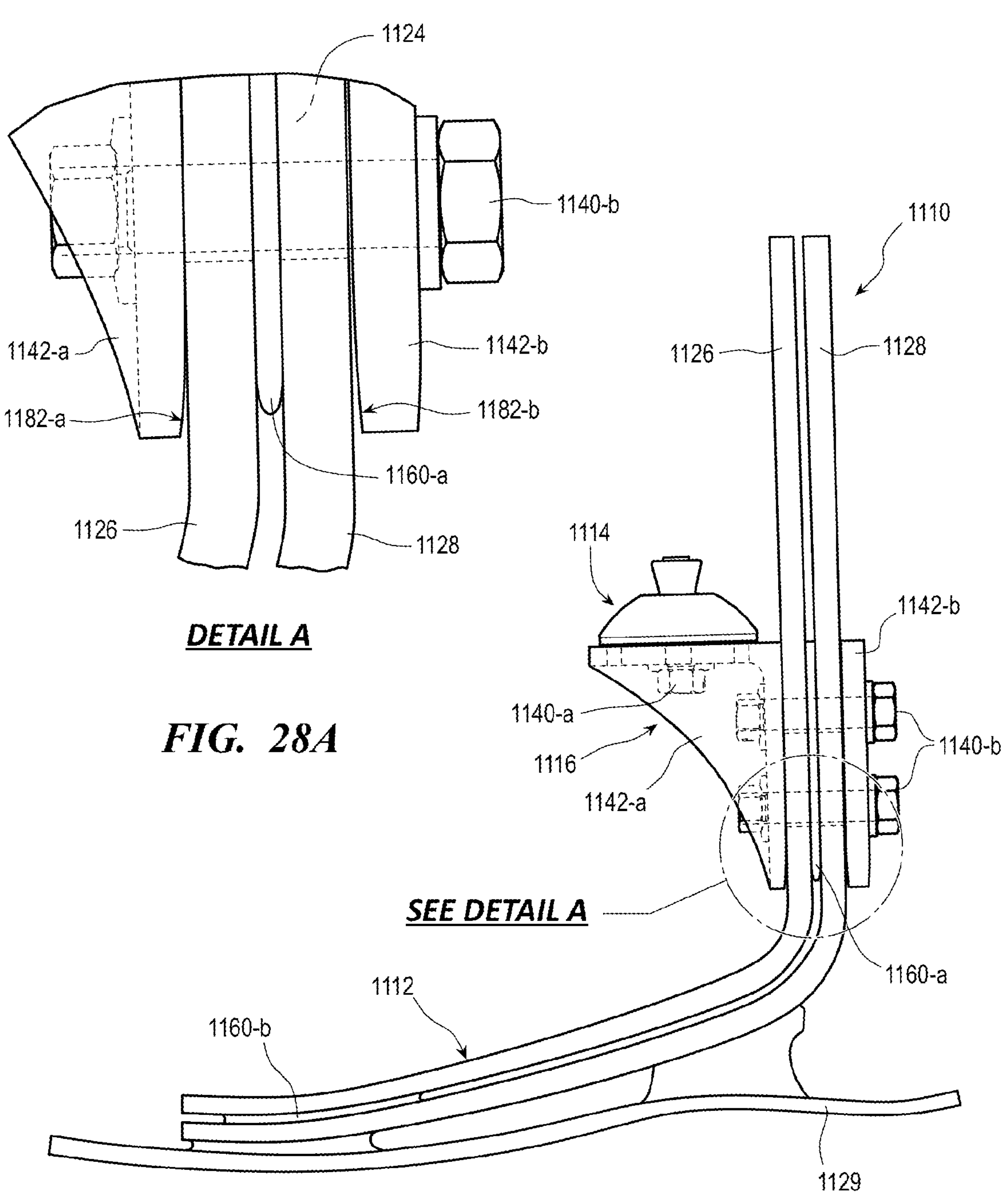
FIG. 28 is a side view of the prosthetic device shown in FIG. 26.
FIG. 28A is a close-up view of a portion of the prosthetic device shown in FIG. 28.
Figure 29:
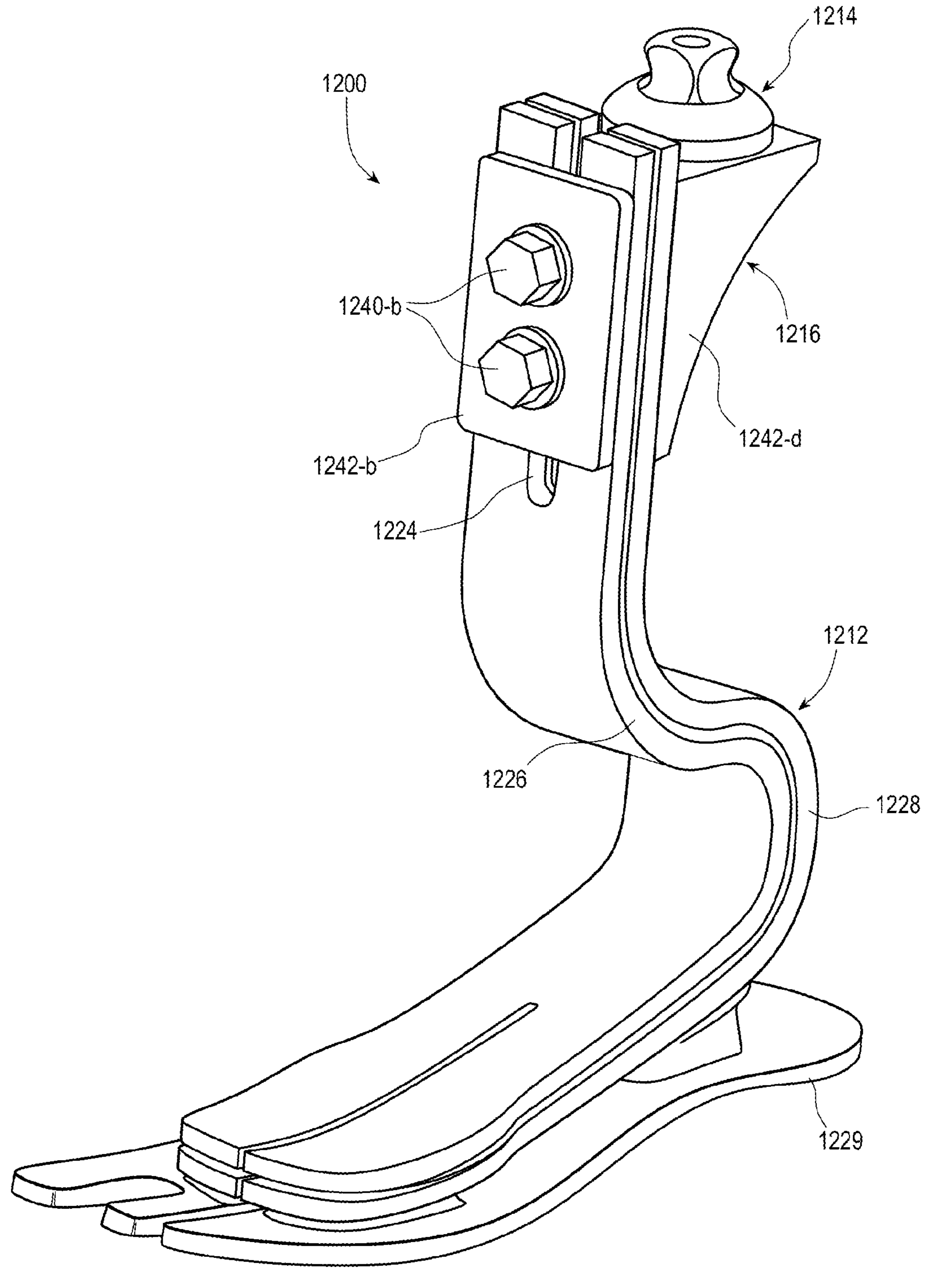
FIG. 29 is a perspective view of another example prosthetic device having height adjustment features in accordance with the present disclosure.

FIG. 27 shows a slot 1152 formed in the bracket 1142-*a* to provide for horizontal adjustment of the adapter 1114 relative to the adjustment assembly 1116 and spring assembly 1112. FIG. 28 shows spacers 1160-*a* and 1160-*b* positioned between the top springs 1126, 1128.

The prosthetic foot 1100 may be referred to as a dual pylon arrangement, wherein the pylon portion of the top springs 1126, 1128 is that portion that extends vertically. The dual pylon arrangement of prosthetic foot 1100 includes center slots in the pylon portions of springs 1126, 1128, and the adjustment assembly 1116 includes an L-shaped bracket-style pylon adapter and related adjustment assembly. The L-shaped bracket 1142-*a* may include vertical reinforcing ribs 1143. The second bracket member 1142-*b* may help distribute the load against the first and second springs 1126, 1128. The brackets 1142-*a*-*b* may each include contoured edges along the distal end thereof on surfaces that face the springs 1126, 1128. These contoured surfaces 1182-*a*, 1182-*b* are shown in the close-up view of FIG. 28A. These contoured surfaces help minimize contact pressure, reduce stresses in the spring members 1126, 1128, and provide increased flexibility overall within the prosthetic foot 1100. The contours 1182-*a*-*b* may be a radius, may include multiple radii, or may be elliptical in shape.

Figure 30:
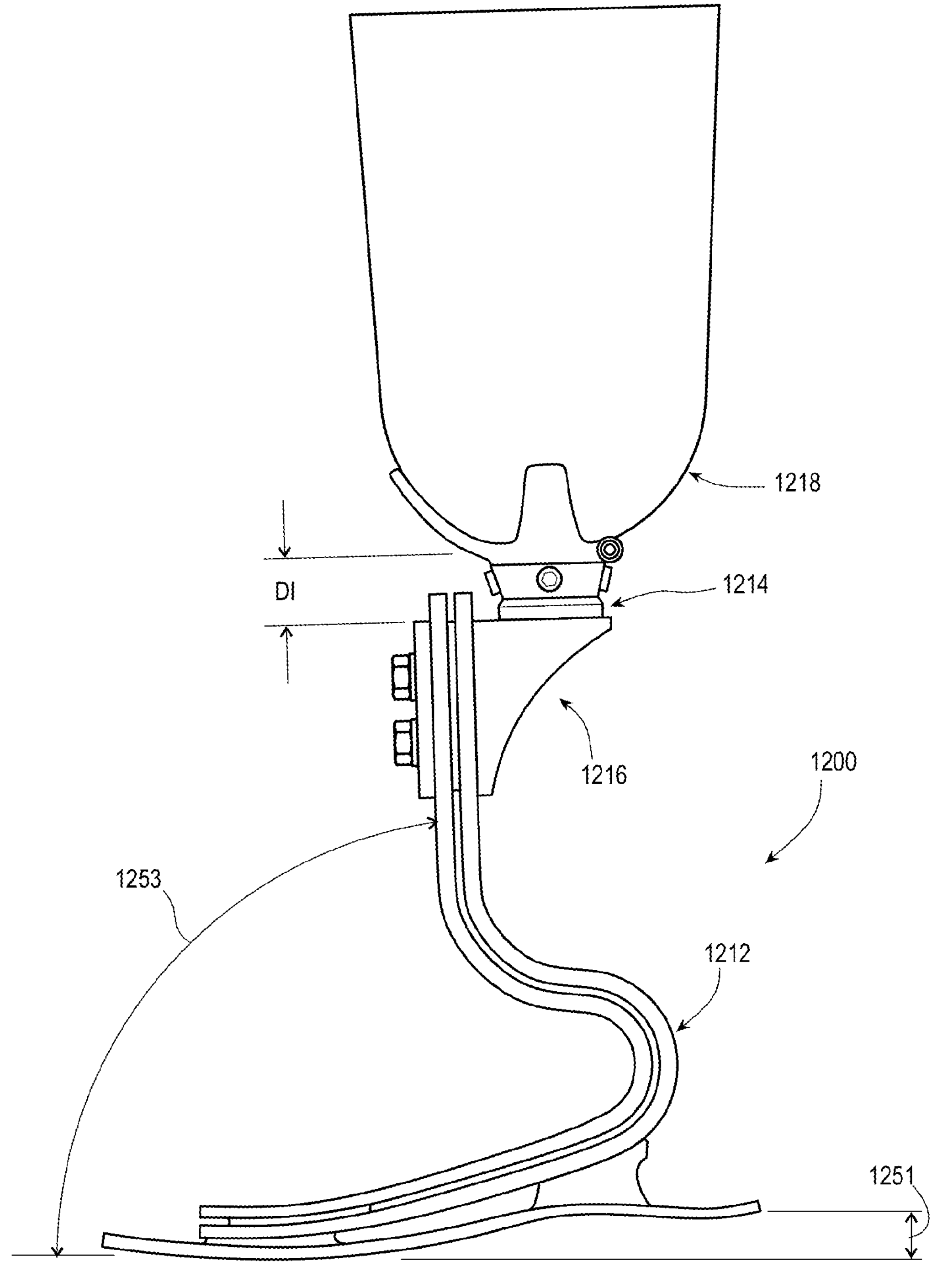
FIG. 30 is a side view of the prosthetic device shown in FIG. 29 with a prosthetic socket mounted thereto.
Figures 31, 31A:
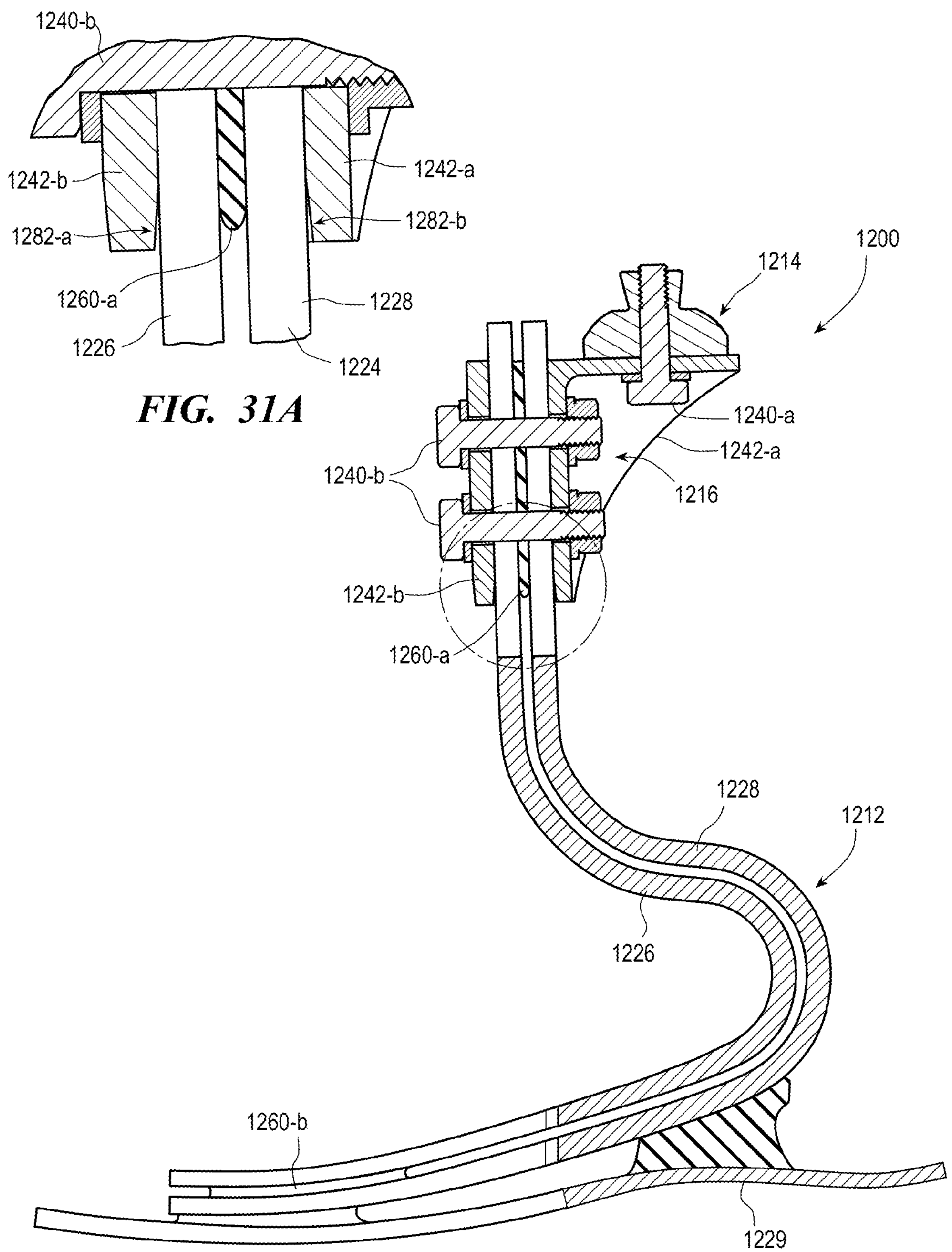
FIG. 31 is a cross-sectional view of the prosthetic device shown in FIG. 29.
FIG. 31A is a close-up view of a portion of the prosthetic device shown in FIG. 31.
Figure 32:
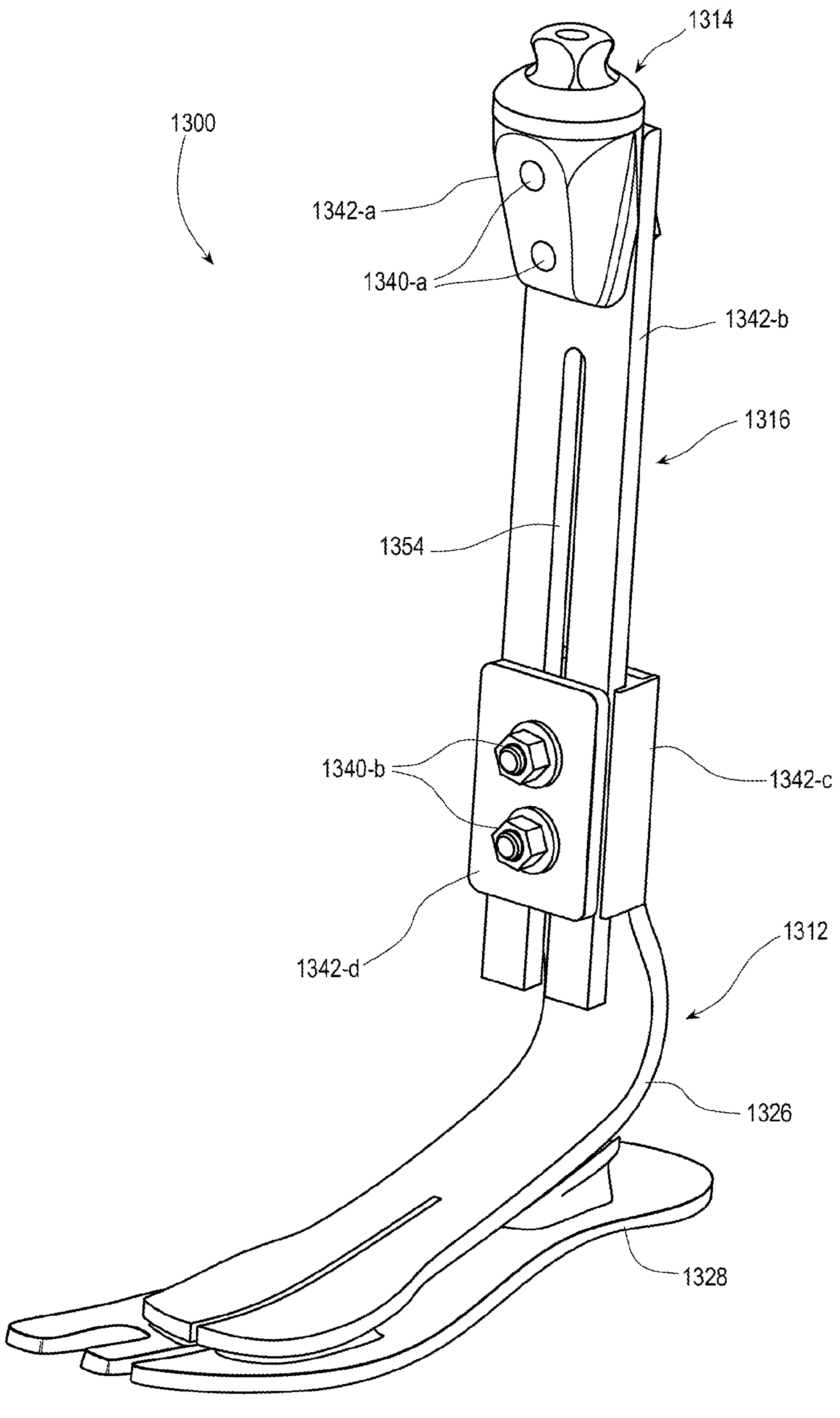
FIG. 32 is a perspective view of another example prosthetic device having height adjustment features in accordance with the present disclosure.

FIGS. 29-31A show another example prosthetic device in the form of a prosthetic foot 1200. The prosthetic foot 1200 includes a spring assembly 1212, an adapter 1214, and an adjustment assembly 1216. The spring assembly 1212 includes first and second top springs 1226, 1228 and a bottom spring 1229. The cross-sectional view of FIG. 31 shows spacers 1260-*a* and 1260-*b*. A slot 1224 is formed in the springs 1226, 1228. As in other examples, an upper spring assembly which includes two or more upper springs my provide enhanced foot function. However, for the purposes of height adjustment a single upper spring provides the same benefits and may result in improved height adjustment simplicity.

The adjustment assembly 1216 includes first and second brackets 1242-*a*, 1242-*b* positioned on posterior and anterior surfaces of the spring assembly 1212, respectively. A first fastener 1240-*a* secures the adapter 1214 to the bracket 1242-*a* as shown in FIG. 31. One or more second fasteners 1240-*b* secure the first and second brackets 1242-*a*-*b* to each other, and extend through the slot 1224 to provide vertical adjustment of the adapter 1214 relative to the spring assembly 1212. FIG. 30 shows a prosthetic socket 1218 secured to the adapter 1214. Other types of prosthetic devices and other features may be mounted to the adapter 1214 such as, for example, a prosthetic pylon, a prosthetic knee, a prosthetic pump, or the like.

The brackets 1242-*a*-*b* may include contoured portions 1282-*a*-*b* along distal ends thereof on surfaces that face the springs 1226, 1228 as shown in FIG. 31A. The contoured surfaces 1282-*a*-*b* may help minimize contact pressure, reduce stresses in the springs 1226, 1228, and/or increase overall flexibility for the prosthetic foot 1200. The contours 1282 may include a radius, multiple radii, or an elliptical shape. Utilizing a simple radius between X and Y has demonstrated a significant advantageous effect on foot function in a vertical pylon foot by decreasing the ankle moment in the late stages of mid-stance when the effective toe length increases quickly but the amputee has little leverage over the foot due to a mostly vertical pylon orientation. Utilizing multiple radii or an elliptical shape may provide further opportunities to fine tune the ankle moment as a function of pylon angle during the gait cycle.

Generally, the prosthetic foot 1200 includes at least one L-shaped bracket 1242 mounted to the pylon portion of the spring assembly 1212 with a center, vertical slot at the proximal end of the spring members 1226, 1228. As shown in FIG. 30, some additional height for the springs 1226, 1228 is possible, and this extra length can remain for safety without interfering with the device 1218 that is mounted to the adapter 1214. Providing this additional length in the proximal direction may make it possible to avoid making the spring assembly 1212 unusable for the amputee if the pylon portion of the springs 1226, 1228 is cut too short, or to avoid having to make a height adjustment by replacing or installing additional components which increase the cost and weight of the prosthetic leg assembly. The approximate additional pylon length allowed before interference with the socket occurs is shown as D1.

FIG. 30 also shows that the posterior bracket 1242-*a* extending in the posterior direction permits the pylon portion of the springs 1126, 1128 to be located anterior to the device 1218 (and the adapter 1214). This arrangement for the pylon portions of the springs 1226, 1228 may provide additional function and permit the springs 1226, 1228 to be longer in the proximal direction, which may be advantageous to the user for several reasons. Furthermore, positioning the adapter 1214 rearward of the springs 1226, 1228 may help avoid the adapter catching on chairs and other obstacles. Further, the arrangement of prosthetic foot 1200 may provide better flexibility for the pylon portion of the springs 1226, 1228 while maintaining the adapter out of the way of obstacles.

FIG. 30 shows the intended orientation of the prosthetic foot 1200 when connected to a prosthetic socket 1218 and when an amputee is standing on flat ground. The distal surface of the bottom spring 1229 in the heel area is located a heel height 1251 above the distal surface in the forefoot area to accommodate the increased thickness of both a shoe and a footshell in the heel area. The pylon of the foot has a planar proximal region for mounting adjustment assembly 1216 and this planar surface has a pylon angle 1253 of about 85-90 degrees from a horizontal ground surface.

FIGS. 32-34A show another example prosthetic device in the form of a prosthetic foot 1300. The prosthetic device 1300 includes a spring assembly 1312, an adapter 1314, and an adjustment assembly 1316. The spring assembly 1312 includes an ankle spring 1326 and a bottom spring 1328, both formed of fiber reinforce plastic (FRP). The adjustment assembly 1316 includes first fasteners 1340-*a* that secure a first bracket 1342-*a* and the adapter 1314 mounted thereto to a top spring 1342-*b* also formed of FRP. The top spring 1342-*b* includes a slot 1354 formed therein. A third bracket 1342-*c* and fourth bracket 1342-*d* secure the second bracket 1342-*b* to the ankle spring 1326 using second fasteners 1340-*b*. The fasteners 1340-*b* are slidable within the slot 1354 to provide adjustment of the top spring 1342-*b* relative to the spring assembly 1312. Since the adapter 1314 is secured to the top spring 1342-*b* in a fixed position, the vertical adjustment of the top spring 1342-*b* relative to the spring assembly 1312 also provides a vertical adjustment of the adapter 1314 relative to the spring assembly 1312.

In at least some arrangements, the third and fourth brackets 1342-*c*-*d* maintain a fixed position relative to the ankle spring 1326. In other arrangements, the ankle spring 1326 also includes a vertical slot formed therein that provides additional height adjustment of the brackets 1342-*c*-*d* relative to the spring assembly 1312.

Figure 33:
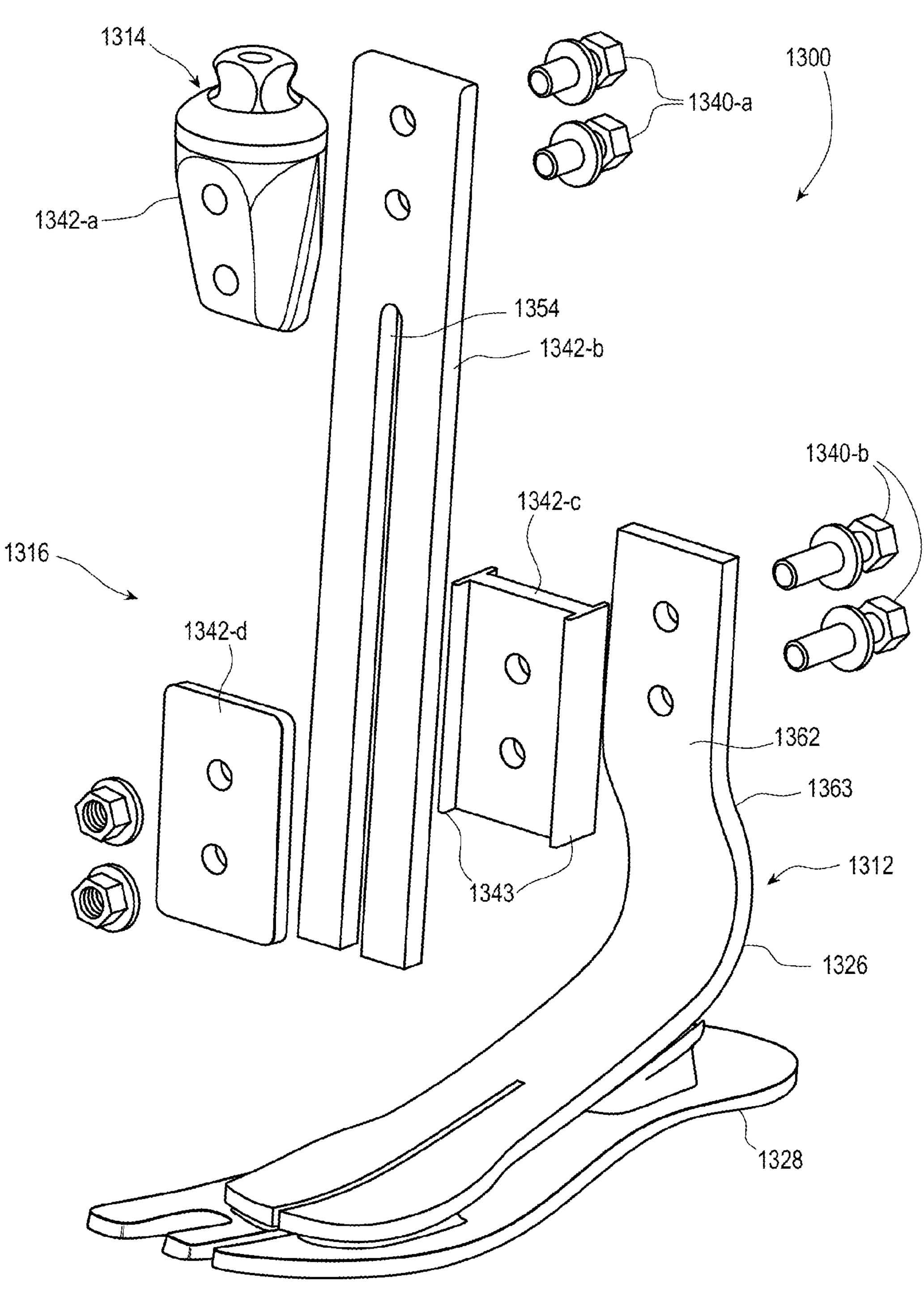
FIG. 33 is a partial-exploded view of the prosthetic device shown in FIG. 32.

The third bracket 1342-*c* may be interposed between the top spring 1342-*b* and a front or anterior surface 1362 of the ankle spring 1326 as shown in FIG. 33. Alternatively, the third bracket 1342-*c* may be positioned on a rear or posterior surface 1363 of the ankle spring 1326. The third bracket 1342-*c* may include guide members 1343 that help maintain alignment of the second bracket 1342-*b* relative to the ankle spring 1326.

In other embodiments, the top spring 1342-*b* may include a slot within which the fasteners 1340-*a* are slidable to provide vertical adjustment of the first bracket 1342-*a* relative to the top spring 1342-*b*. The first bracket 1342-*a* may be integrally formed with the adapter 1314 so as to provide a single-piece construction for the adapter 1314 and first bracket 1342-*a*. In at least some arrangements, the first bracket 1342-*a* includes a vertically oriented slot feature within which the fasteners 1340-*a* are slidable to provide vertical adjustment of the first bracket 1342-*a* relative to the second bracket 1342-*b*. In still further arrangements, the third and fourth brackets 1342-*c*-*d* may each include vertically oriented slots that provide for sliding adjustment of the fasteners 1340-*b* therein to provide vertical adjustment of the brackets 1342-*c*-*d* relative to the spring assembly 1312 and/or the top spring 1342-*b*. In at least some arrangements, the top spring 1342-*b* includes two fastener apertures in place of the slot 1354. Any combination of slots and apertures provided in the various features of the spring assembly 1312 and adjustment assembly 1316 may be used to provide desired height adjustability for the prosthetic foot 1300.

Figures 34, 34A:
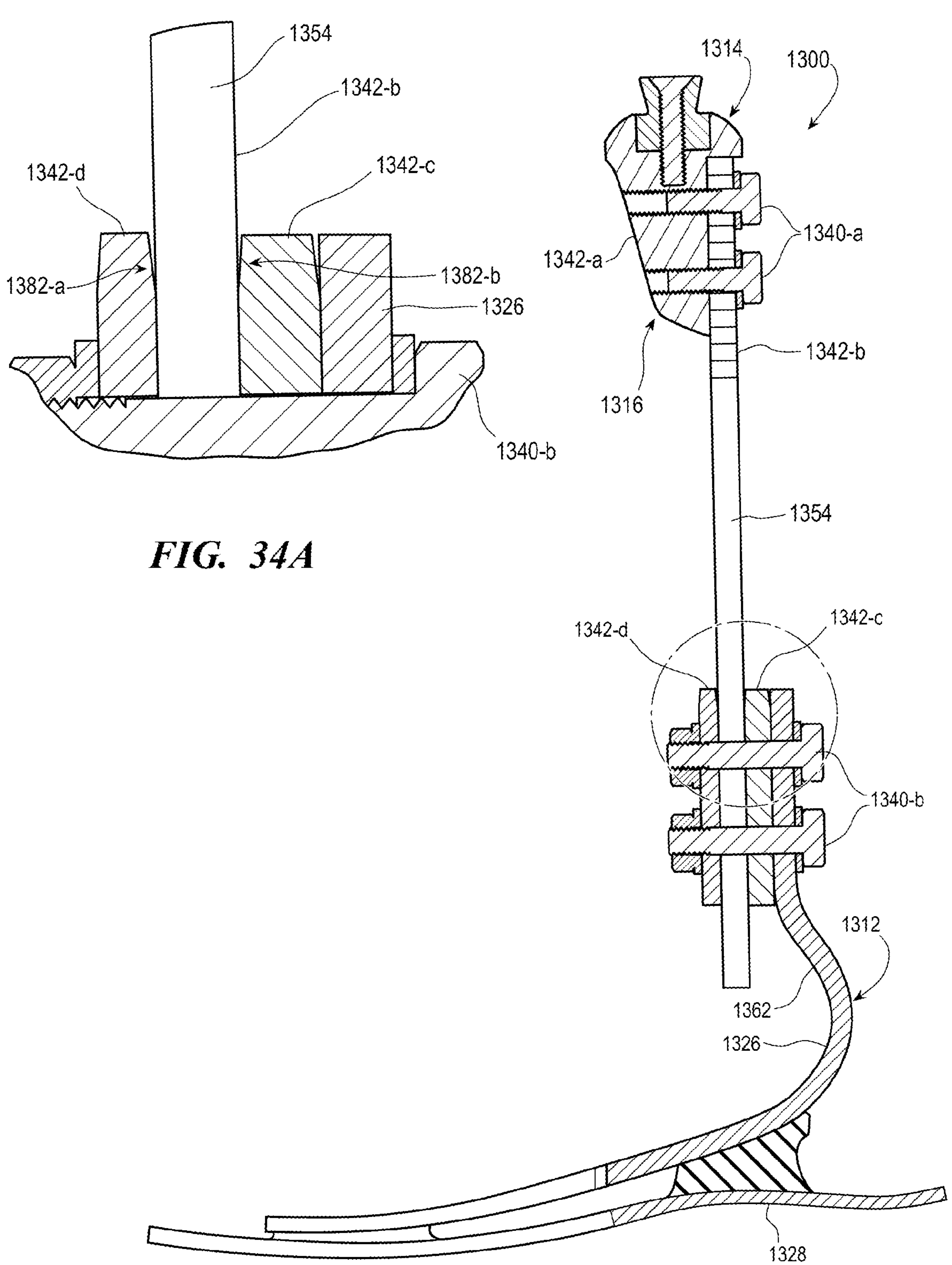
FIG. 34 is a cross-sectional view of the prosthetic device shown in FIG. 32.
FIG. 34A is a close-up view of a portion of the prosthetic device shown in FIG. 34.

The proximal ends of the third and fourth brackets 1342-*c*-*d* along the surface facing the second bracket 1342-*b* may include contours 1382-*a* and 1382-*b* as shown in a close-up view of FIG. 34A. The contours 1382 may help minimize contact pressure, reduce stresses in the spring 1326, and increase overall flexibility for the prosthetic foot 1300 without compromising strength.

The prosthetic foot 1300 may include multiple pylon features, including a pylon portion of the ankle spring 1326 (the portion extending vertically) and the pylon structure of the top spring 1342-*b*. Each of the pylon portions of the prosthetic foot 1300 may be referred to as a spring member or have spring characteristics.

The curvature of the ankle spring 1326 in the area of the ankle may provide for less critical cutoff length for the proximal end of the top spring 1326 and/or the overall length of the second bracket 1342-*b*. The top spring 1342-*b* (also referred to as an intermediate or proximal pylon) may be replaceable and interchangeable with other spring members having different spring characteristics such as strength, flexibility, and the like.

Figure 35:
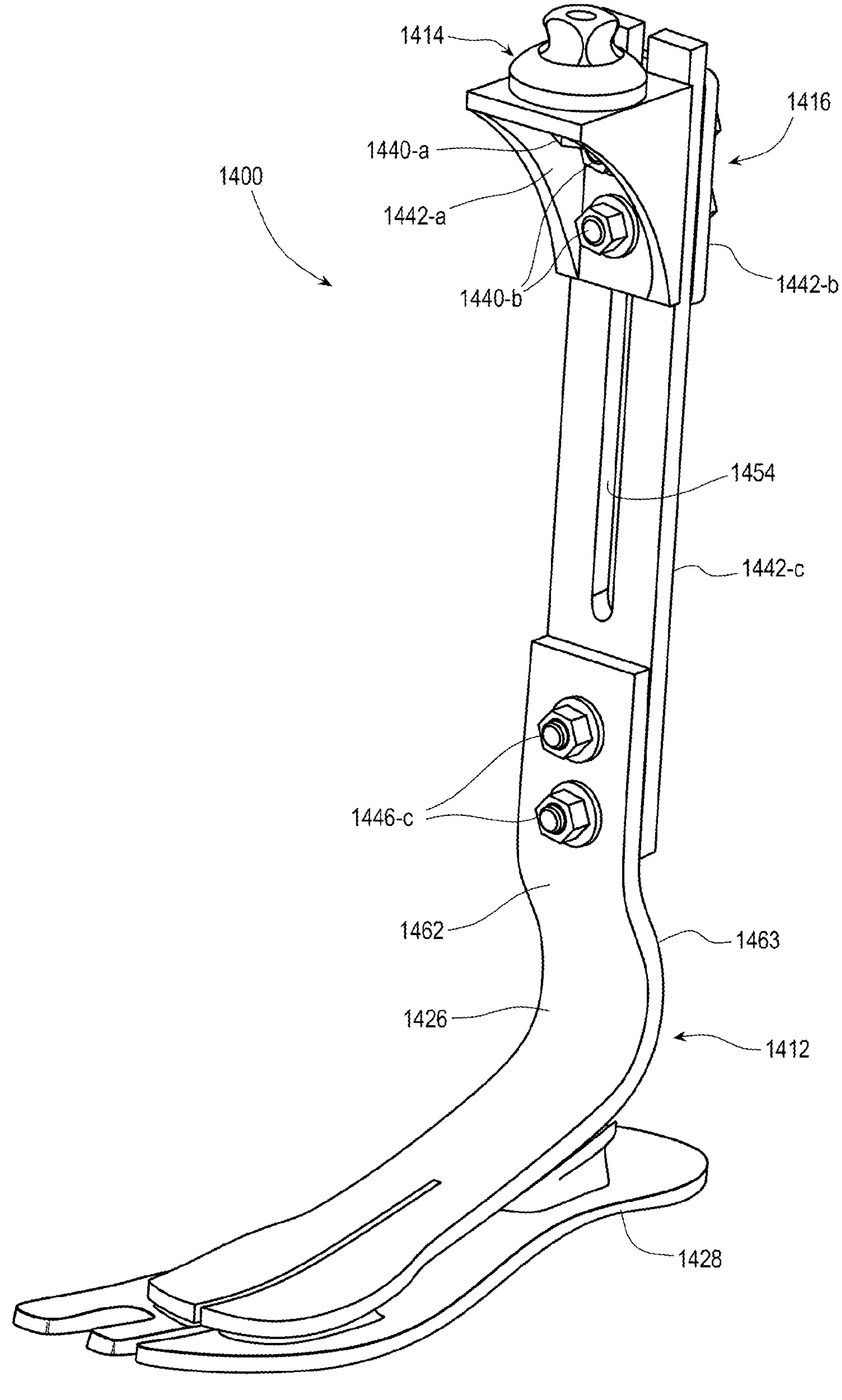
FIG. 35 is a perspective view of another example prosthetic device having height adjustment features in accordance with the present disclosure.
Figure 36:
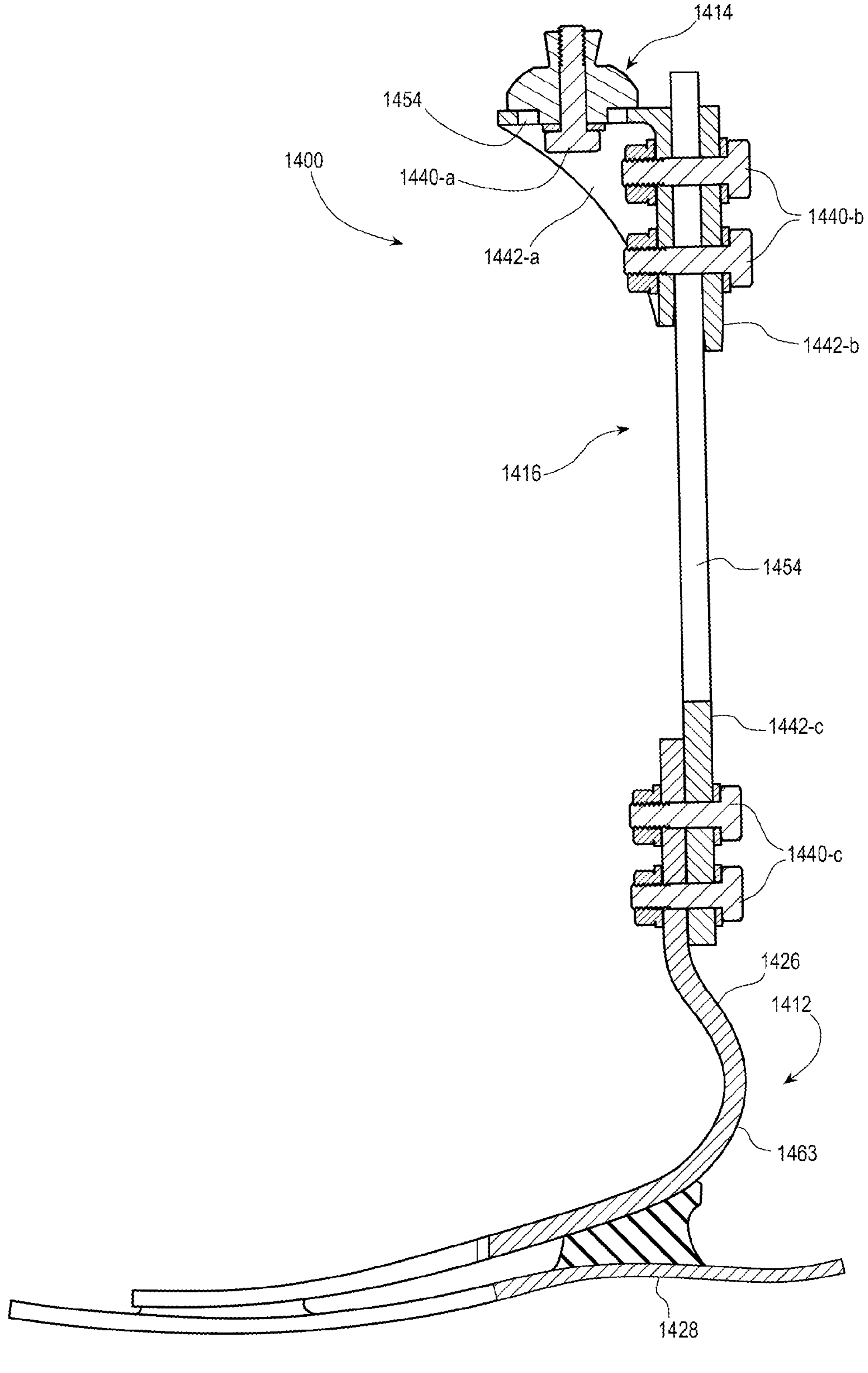
FIG. 36 is a cross-sectional view of the prosthetic device shown in FIG. 35.

FIGS. 35 and 36 show another prosthetic device in the form of a prosthetic foot 1400. The prosthetic foot 1400 includes a spring assembly 1412, an adapter 1414, and an adjustment assembly 1416. The spring assembly 1412 includes ankle and bottom spring members 1426, 1428. The ankle spring 1426 includes an anterior surface 1462 and a posterior surface 1463. The adjustment assembly 1416 is mounted to the posterior surface 1463, but may, in other embodiments, be mounted to the anterior surface 1462. The adjustment assembly of FIG. 32 may also be mounted to either the anterior or posterior surface of the top spring.

The adjustment assembly 1416 includes first and second brackets 1442-*a* and 1442-*b*. The adapter 1414 is mounted to the first bracket 1442-*a* with a first fastener 1440-*a*. One or more second fasteners 1440-*b* secure the first bracket 1442-*a* to a second bracket 1442-*b* and top spring 1442-*c*. The top spring 1442-*c* may be interposed between the brackets 1442-*a*-*b*. The top spring 1442-*c* may include a slot 1415 within which the fasteners 1440-*b* are slidable vertically to provide a height adjustment of the adapter 1414 relative to the spring assembly 1412. The top spring 1442-*c* may be secured to the spring assembly 1412 with one or more third fasteners 1440-*c*.

FIG. 36 shows a slot 1454 formed in the first bracket 1442-*a* that provides for horizontal adjustment of the adapter 1414 relative to the first bracket 1442-*a*. In at least some arrangements, the slot 1454 may be arranged in a medial/lateral direction to provide medial/lateral adjustment of the adapter 1414 relative to the first bracket 1442-*a*.

Many other variations of slots may be provided for the different brackets of the adjustment assembly 1416. For example, the first and second brackets 1442-*a*-*b* may include vertical slots instead of or in addition to the vertical slot 1454 to provide desired vertical adjustment. The ankle spring 1426 may include vertical slots and/or the top spring 1442-*c* may include vertical slots within which the fasteners 1440-*c* are slidable to provide desired vertical adjustment.

The top spring 1442-*c* may be referred to as a pylon of the prosthetic foot 1400 similar to the top spring 1442-*b* of prosthetic foot 1300 described above. The use of multiple pylon springs or spring components for the prosthetic foot 1400 may have similar advantages as described above with reference to prosthetic foot 1300.

The top spring 1342-*c* may be directly mounted to and interface with the top spring 1426. In embodiments in which the bracket 1442-*c* comprises a composite material, the prosthetic foot 1400 may be referred to as a direct carbon-on-carbon joint formed between the adjustment assembly 1416 and the spring assembly 1412. The adjustment assembly 1416 may provide a connection to the spring assembly 1412 without the use of backing plates, intermediate brackets, or the like, such as those described above with reference to prosthetic foot 1300.

Further, the L-shaped first bracket 1442-*a* may be positioned on either the anterior side or posterior side of the third bracket 1442-*c*. Furthermore, the L-shaped bracket 1442-*a* may arrange the adapter 1414 at a variety of different anterior/posterior positions relative to the spring assembly 1412 and provide other advantages as described herein because of that anterior/posterior adjustability.

Figure 37:
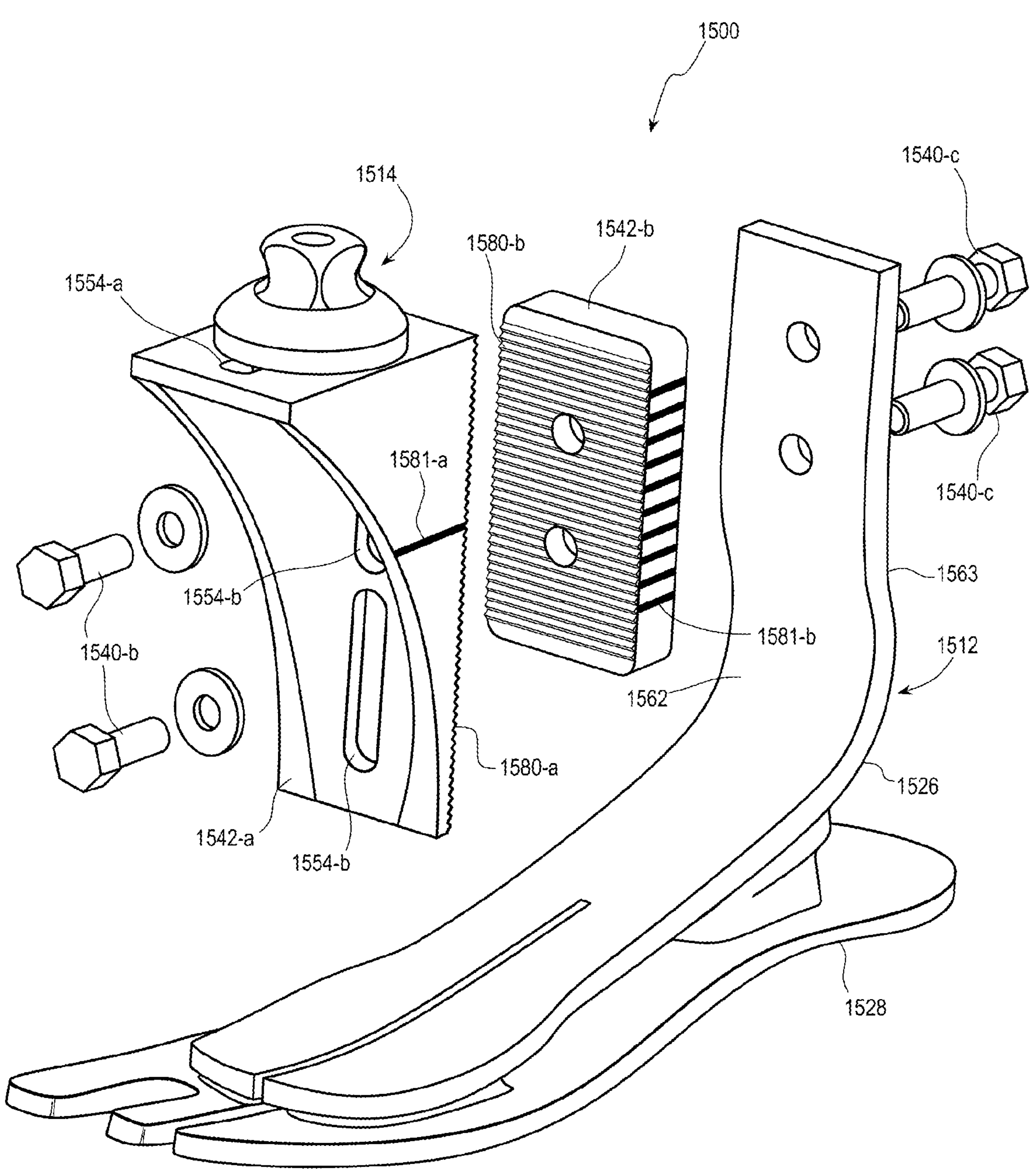
FIG. 37 is a partially-exploded perspective view of another example prosthetic device having height adjustment features in accordance with the present disclosure.
Figure 38:
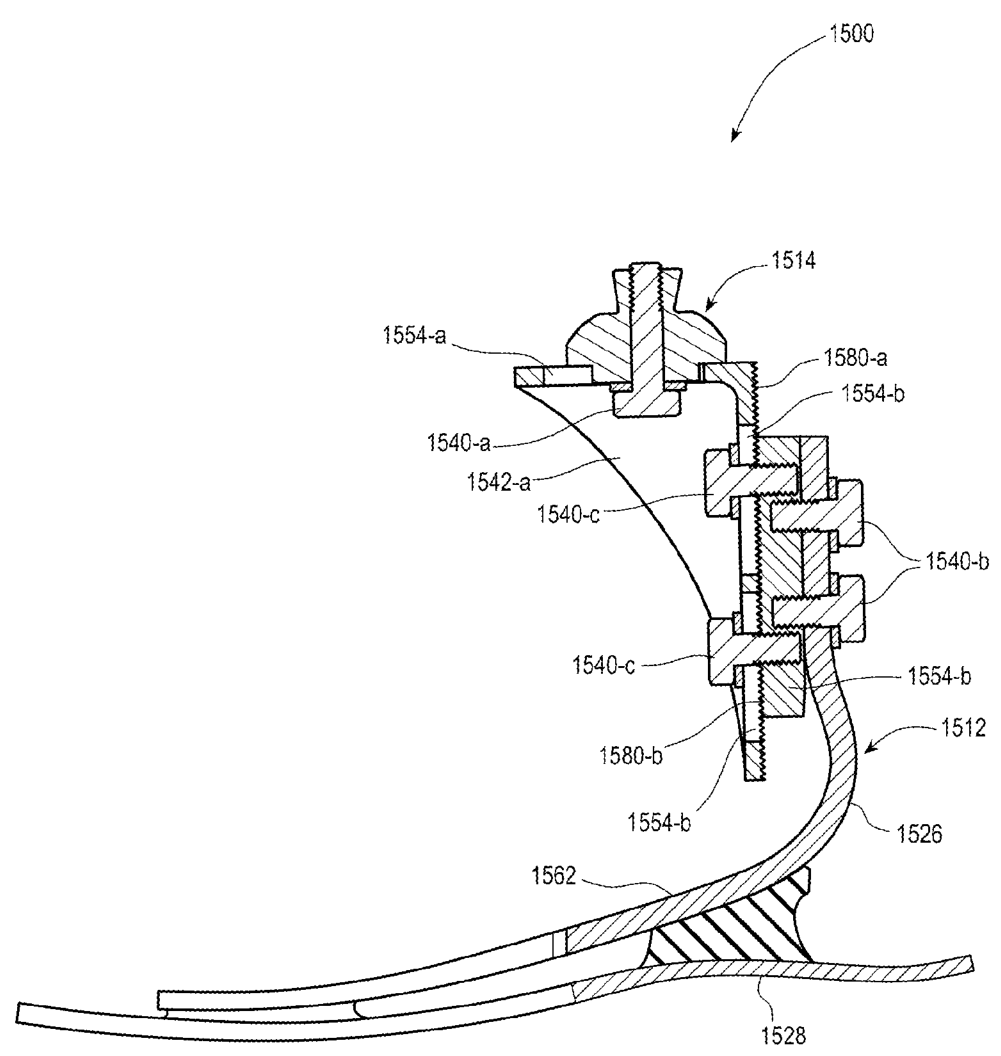
FIG. 38 is a cross-sectional view of the prosthetic device shown in FIG. 37.
Figure 39:
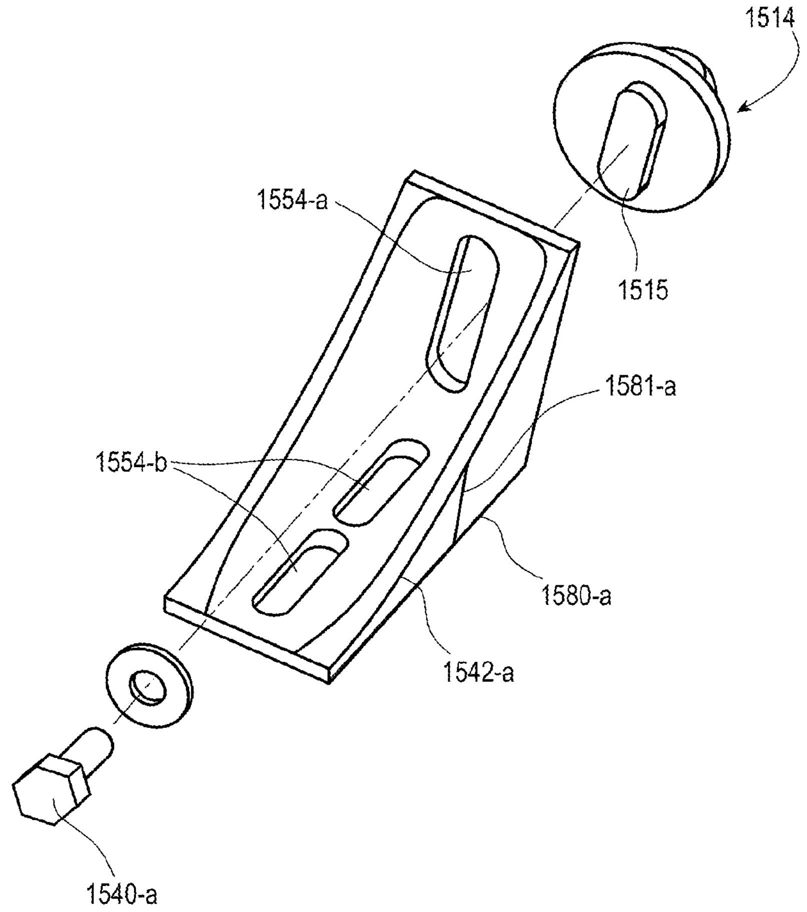
FIG. 39 is a bottom perspective view of a height adjustment feature of the prosthetic device shown in FIGS. 37 and 38.

FIGS. 37-39 show another example prosthetic device in the form of a prosthetic foot 1500. The prosthetic foot 1500 includes a spring assembly 1512, an adapter 1514, and an adjustment assembly 1516. The spring assembly 1512 includes top and bottom springs 1526, 1528. The top spring 1526 includes anterior and posterior surfaces 1562, 1564.

The adjustment assembly 1516 includes a first bracket 1542-*a* that may be referred to as an L-shaped bracket having supporting cross-ribs or other structural features. The bracket 1542-*a* may include a first slot 1554-*a* that provides anterior/posterior adjustability of the adapter 1514 via connection using a fastener 1540-*a* (see FIG. 38). The bracket 1542-*a* includes one or more additional vertically oriented slots 1554-*b* through which second fasteners 1540-*b* extend and are slidable within to provide vertical adjustment of the adapter 1514 relative to the spring assembly 1512. The bracket 1542-*a* may further include serrations or tines 1580-*a* along a posterior, rearward-facing surface thereof. The tines 1580-*a* may engage with mating tines or serrations 1580-*b* formed in a second bracket or spacer 1542-*b*. The bracket 1542-*b* may be secured to the spring 1526 with third fasteners 1540-*c*. In at least some arrangements, the spring 1526 and/or the bracket 1542-*b* include vertically arranged slots that provide vertical adjustment of the fasteners 1540-*c* thereof to provide a height adjustment of the adapter 1514 relative to the spring assembly 1512.

The embodiment of FIGS. 37 and 38 show the first and second brackets 1542-*a*-*b* mounted to the anterior surface 1562 of the top spring 1526. In other arrangements, the first and second brackets 1542-*a*-*b* may be mounted to the posterior surface 1563 of the top spring 1526.

The mating tines 1580-*a*-*b* may provide for incremental height adjustability for the adapter 1514 relative to the spring assembly 1526. The size and shape of the tines 1580-*a*-*b* may be adjusted to provide different increments, relative alignment of features, and the like. In some embodiments, the second bracket 1514-*b* may be interchanged with other structures that provide different types of adjustability, mating with tines of the first bracket 1542-*a*, or the like. In some embodiments, the second bracket 1542-*b* may be removed altogether. In still further embodiments, the second set of tines 1580-*b* may be formed or provided on one or both of the anterior and posterior surfaces 1562, 1563 of the top spring 1526 to provide incremental change in height at an interface with either the first bracket 1542-*a* directly or with the second bracket 1542-*b*.

The prosthetic foot 1500 may be referred to as including a toothed adapter or adjustment assembly to provide specific height adjustment for the prosthetic foot 1500. The L-shaped bracket 1542-*a* and the bracket or spacer 1542-*b* may have teeth on mating surfaces which establish the vertical height for the adjustment assembly. The first and second brackets 1542-*a*-*b* may include additional lines 1581-*a* and 1581-*b* so that the height locations can be indexed. Although a pair of vertically aligned slots 1554-*b* are provided in the first bracket 1542-*a*, a single slot could be used, or a pair of slots positioned side by side could be used.

FIG. 39 shows the various slots 1554-*a*-*b*, tines 1580-*a* and indexing marker 1581-*a* and the first bracket 1542-*a*. FIG. 39 further shows an alignment protrusion 1515 formed along the adapter 1514 that acts as a follower within the slot 1554-*a*. The protrusion 1515 may be elongate in shape to help eliminate rotation of the adapter 1514 relative to the bracket 1542-*a*.

Figure 40:
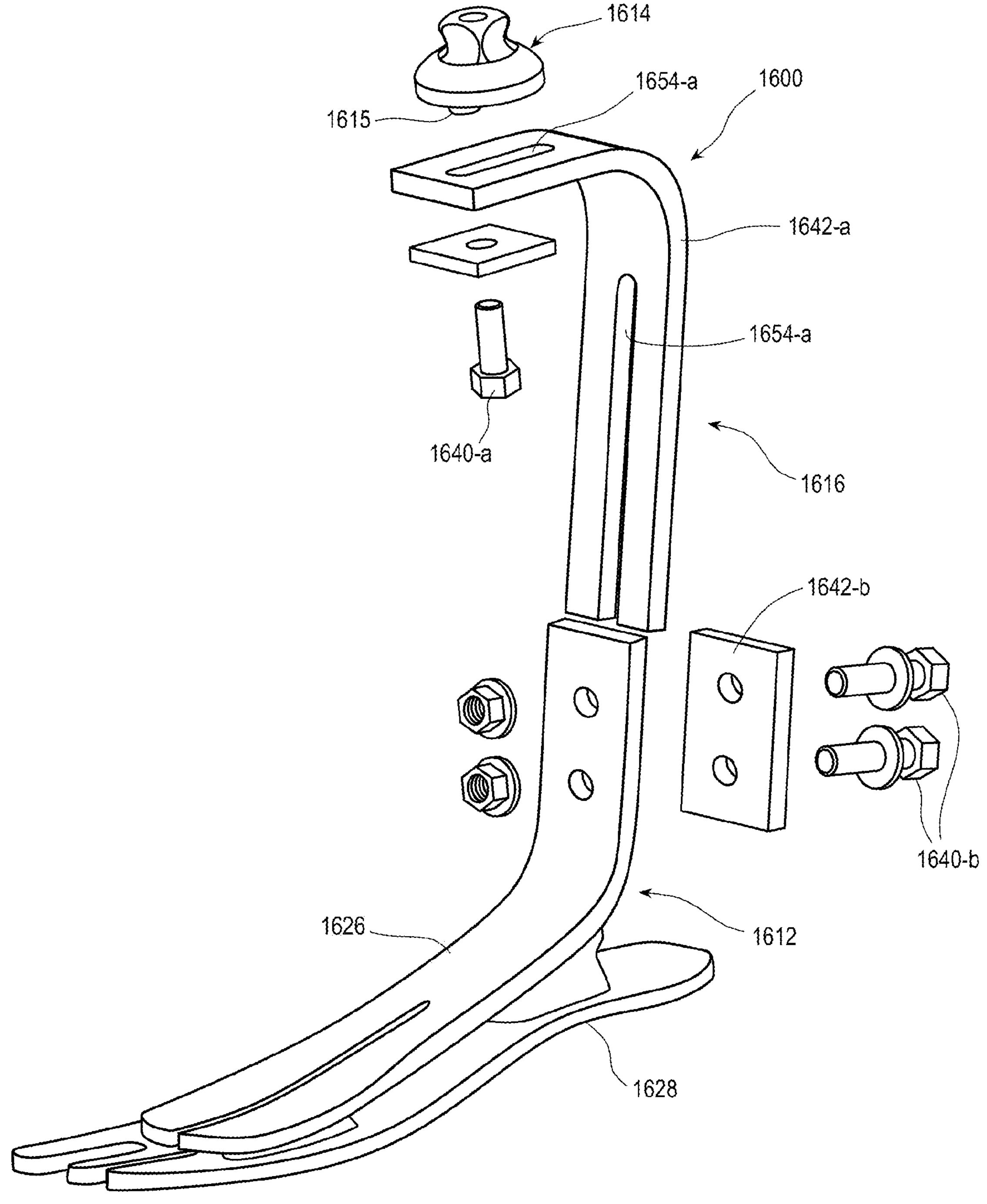
FIG. 40 is a partial-exploded perspective view of another example prosthetic device having height adjustment features in accordance with the present disclosure.

FIG. 40 shows a prosthetic device in the form of a prosthetic foot 1600. The prosthetic foot 1600 includes a spring assembly 1612, an adapter 1614, and an adjustment assembly 1616. The spring assembly 1612 includes top and bottom springs 1626, 1628. The adjustment assembly 1616 includes a first bracket 1642-*a* and a second bracket 1642-*b*. A first fastener 1640-*a* secures the adapter 1614 to the first bracket 1642-*a*. The first bracket 1642-*a* includes a slot 1654-*a* within which the fastener 1640-*a* is slidable to provide anterior/posterior adjustment of the adapter 1614. The adapter 1614 may include an alignment protrusion 1615 that follows within the slot 1654-*a* to provide a more positive connection and/or eliminate rotation of the adapter 1614 relative to the first bracket 1642-*a*.

The first bracket 1642-*a* may include a second slot 1654-*b* along a pylon or vertically oriented portion thereof. A second set of fasteners 1640-*b* may slide within the slot 1654-*b* to provide vertical adjustment of the first bracket 1642-*a* and the adapter 1614 relative to the spring assembly 1612. The first bracket 1642-*a* may be referred to as a second pylon in addition to the first pylon provided by the top spring 1626. The first bracket 1642-*a* may be considered a spring member and referred to as an intermediate spring member or proximal spring member. The second bracket 1642-*b* may capture the first bracket 1642-*a* between the top spring 1626 and the second bracket 1642-*b* to provide an improved engagement and interface between the first bracket 1642-*a* and the spring assembly 1612, which may improve force transfer and other advantages.

The prosthetic foot 1600 may be described as having a distal foot plate (the bottom spring member 1628), an intermediate spring member (the top spring 1626), and an upper spring assembly (including the first bracket 1642-*a*). After determining the correct length of the upper spring assembly to establish the correct height for the amputee or user of the prosthetic foot 1600, the upper spring (first bracket 1642-*a*) may be cut to length.

Figure 41:
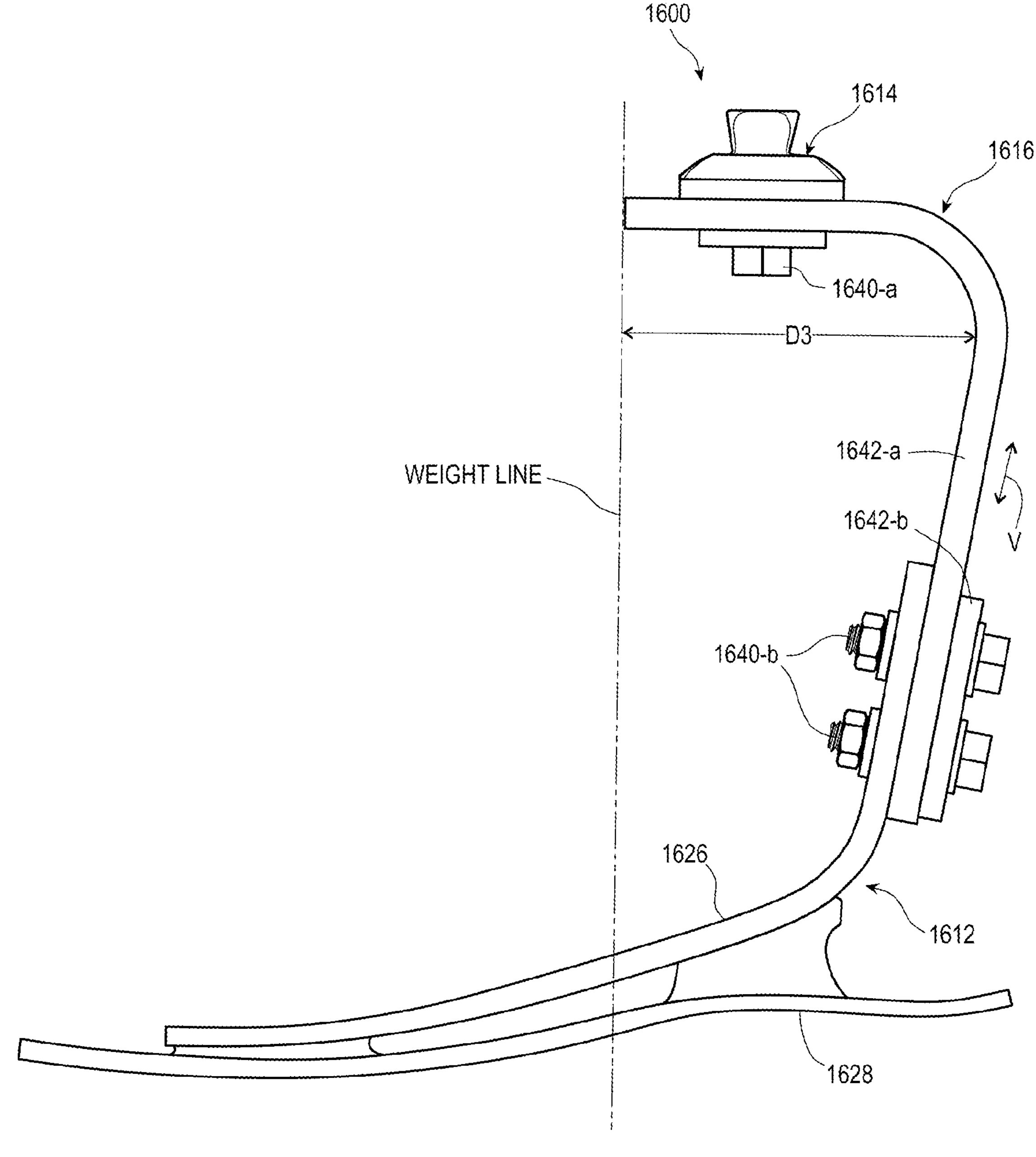
FIG. 41 is a side view of the prosthetic device shown in FIG. 40.

FIG. 41 shows a weight line associated with the prosthetic foot 1600. The weight line is the location of the center of gravity of an amputee when standing with the prosthetic foot 1600 mounted to the residual limb. The distance from the weight line to the vertically oriented portion of the foot structure is referred to as distance $D_3$. The distance $D_3$ determines the moment applied to the vertical portion of the foot (i.e., the vertical segment of the first bracket 1642-*a* and the vertical portion of the top spring 1626). The greater the distance $D_3$, the higher the bending moments apply, which results in larger spring displacement during walking and running. The features of prosthetic foot 1600 may result in an adjustable height, increased energy return, and greater comfort for the user during walking and running. Furthermore, the prosthetic foot 1600 provides for adjustability in the anterior/posterior direction for the adapter 1614, and height adjustability for the adapter 1614 even after cutting the first bracket 1642-*a* to length during an initial fitting of the prosthetic foot 1600 for an amputee.

Figure 42:
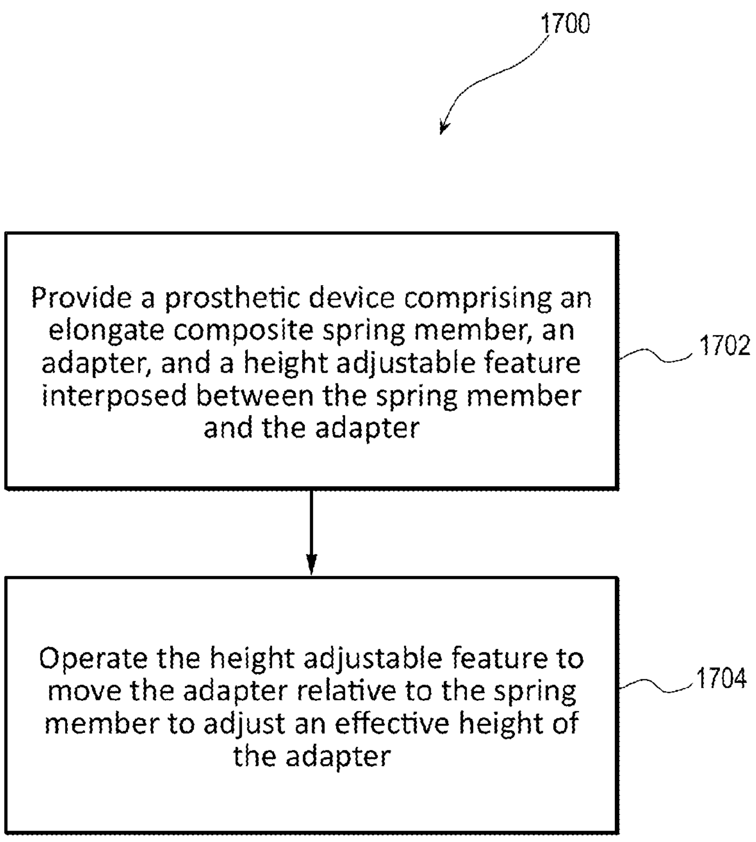
FIG. 42 is a flow diagram showing steps of an example method in accordance with the present disclosure.

FIG. 42 is a flow diagram illustrating an example method 1700 of adjusting an effective height of a prosthetic device. The method 1700 may represent one or more steps applicable to operation of any one of the prosthetic devices and/or adapters or adjustment assemblies disclosed herein with reference to FIGS. 1-41. For example, the steps of method 1700 may reflect operation of prosthetic foot 10 and adjustment assembly 16 described above with reference to FIGS. 1-4D. While several method steps associated with method 1700 are shown in FIG. 42, other variations of related methods of adjusting an effective height of a prosthetic device such as a prosthetic foot, and/or use of such an adjustable height prosthetic device in the course of the present disclosure may include more or fewer steps than those shown in FIG. 42.

The method 1700, at block 1702, includes providing a prosthetic device comprising of an elongate composite spring member, an adapter, a height adjustable feature interposed between the spring member and the adapter. At 1704, the method 1700 includes operating the height adjustable feature to move the adapter relative to the spring member to adjust an effective height of the adapter. The spring member may include a vertically arranged portion, and the height adjustable feature may be moveable vertically relative to the vertically arranged portion. At least one of the vertically arranged portion and the height adjustable feature may include at least one slot, and the prosthetic device further includes at least one fastener extending through the at least one slot to releasably hold a position of the adapter relative to the spring member.

Figure 43:
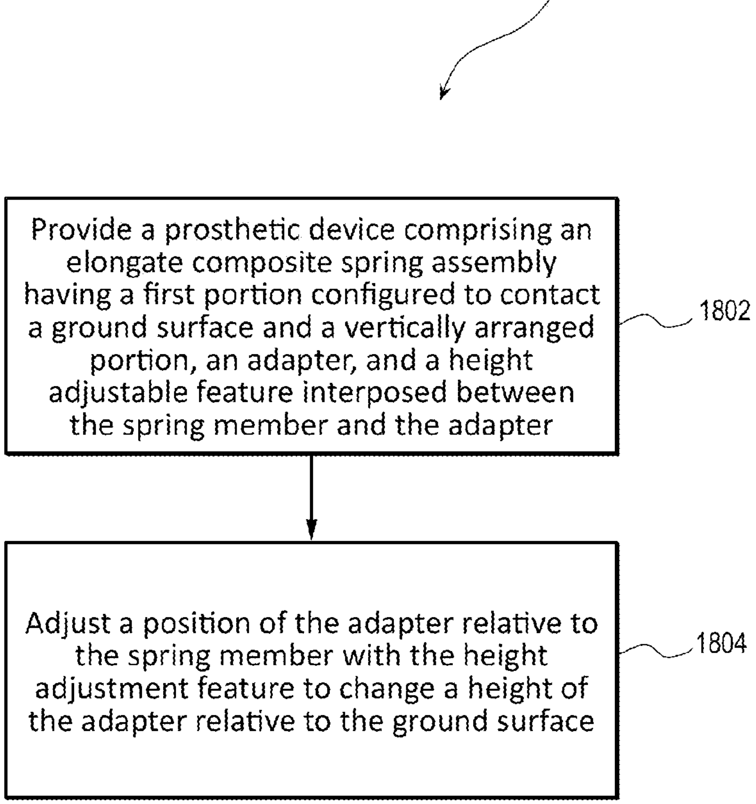
FIG. 43 is a flow diagram showing steps of another example method in accordance with the present disclosure.

FIG. 43 is a flow diagram illustrating an example method 1800 of adjusting an effective height of a prosthetic foot. The method 1800 may represent one or more steps applicable to operation of any one of the prosthetic devices and/or adjustment assemblies or other features described above with reference to FIGS. 1-41. For example, the steps of method 1800 may reflect operation of prosthetic foot 10 and adjustment assembly 16 described above with reference to FIGS. 1-4B. While several method steps associated with method 1800 are shown in FIG. 43, other variations of related methods of adjusting an effective height of a prosthetic foot and/or use of the adjustable height prosthetic foot in accordance with the present disclosure may include more or fewer steps than those shown in FIG. 43.

The method 1800, at block 1802, includes providing a prosthetic foot comprising an elongate composite spring assembly having a first portion configured to contact a ground surface in a vertically arranged portion, an adapter, and a height adjustable feature interposed between vertically arranged portion and the adapter. At 1804, the method 1800 includes adjusting a position of the adapter relative to the spring member with the height adjustment feature to change the height of the adapter relative to the ground surface. The height adjustable feature may include an indexed member that provides predefined height adjustments. At least one of the spring assembly, the adapter, and the height adjustable feature may include at least one slot, and the prosthetic device may further include at least one fastener extending through the at least one slot to releasably hold a position of the adapter relative to the spring assembly.

FIGS. 44A-44C show another example prosthetic device in the form of a prosthetic foot 1900. Specifically, FIG. 44A is an exploded perspective view of the prosthetic foot 1900, FIG. 44B is a front view of the prosthetic foot 1900, and FIG. 44C is a cross-sectional side view of a portion of the prosthetic foot 1900. The prosthetic foot 1900 includes a spring assembly 1912, an adapter 1914, and an adjustment assembly 1916. The spring assembly 1912 includes top and bottom springs 1926, 1928. The top spring 1926 includes anterior and posterior surfaces 1962, 1964.

The adjustment assembly 1916 includes a first bracket 1942-*a* that may be referred to as an L-shaped bracket having supporting cross-ribs or other structural features and a second bracket 1942-*b*. The bracket 1942-*a* may include a first slot 1954-*a* that provides anterior/posterior adjustability of the adapter 1914 via connection using a fastener 1940-*a*. The bracket 1942-*a* includes an additional vertically oriented slot 1954-*b* through which a second fastener 1940-*b* extends and is slidable within to provide vertical adjustment of the adapter 1914 relative to the spring assembly 1912. The second fastener 1940-*b* extends through both of the brackets 1942-*a*-*b* to sandwich the spring assembly 1912 therebetween. The bracket 1942-*a* may further include serrations or tines 1980-*a* along a posterior, rearward-facing surface thereof. The tines 1980-*a* may engage with mating tines or serrations 1980-*b* formed in a toothed plate 1942-*c*. In the illustrated embodiment, the toothed plate 1942-*c* is be secured to the spring 1926 by bonding the toothed plate 1942-*c* to the spring 1926. In alternative embodiments, the toothed plate 1942-*c* may be attached to the spring 1926 by any attachment mechanism that enables the prosthetic foot 1900 to operate as described herein. In at least some arrangements, the bracket 1942-*b* includes the vertically oriented slot 1954-*b* that provides vertical adjustment of the second fastener 1940-*b* thereof to provide a height adjustment of the adapter 1914 relative to the spring assembly 1912. The embodiment of FIGS. 44A-44C shows the first bracket 1942-*a* and the toothed plate 1942-*c* mounted to the anterior surface 1962 of the top spring 1926. In other arrangements, the first bracket 1942-*a* and the toothed plate 1942-*c* may be mounted to the posterior surface 1963 of the top spring 1926.

The mating tines 1980-*a*-*b* may provide for incremental height adjustability for the adapter 1914 relative to the spring assembly 1926. The size and shape of the tines 1980-*a*-*b* may be adjusted to provide different increments, relative alignment of features, and the like. In some embodiments, the toothed plate 1942-*c* may be interchanged with other structures that provide different types of adjustability, mating with tines of the first bracket 1942-*a*, or the like. In some embodiments, the toothed plate 1942-*c* may be removed altogether. In still further embodiments, the second set of tines 1980-*b* may be formed or provided on one or both of the anterior and posterior surfaces 1962, 1964 of the top spring 1926 to provide incremental change in height at an interface with either the first bracket 1942-*a* directly or with the toothed plate 1942-*c*.

The prosthetic foot 1900 may be referred to as including a toothed adapter or adjustment assembly to provide specific height adjustment for the prosthetic foot 1900. The L-shaped bracket 1942-*a* and the toothed plate 1942-*c* may have teeth on mating surfaces which establish the vertical height for the adjustment assembly. The first bracket and the toothed plate 1942-*a*-*b* may include additional lines 1981-*a* and 1981-*b* so that the height locations can be indexed. The toothed plate 1942-*c* may be formed of a thermoplastic material, preferably a fiber reinforced thermoplastic that is injection molded into the extrusion compound or may be formed of aluminum or stainless steel. The toothed plate 1942-*c* allows for discrete and indexed height adjustment, reacts to medial-lateral moment, and supports vertical load, reducing the load on the fasteners 1940-*a*-*b*.

FIGS. 45A-45C show another example prosthetic device in the form of a prosthetic foot 2000. Specifically, FIG. 45A is an exploded perspective view of the prosthetic foot 2000, FIG. 45B is a front view of the prosthetic foot 2000, and FIG. 45C is a cross-sectional side view of a portion of the prosthetic foot 2000. The prosthetic foot 2000 includes a spring assembly 2012, an adapter 2014, and an adjustment assembly 2016. The spring assembly 2012 includes top and bottom springs 2026, 2028. The top spring 2026 includes anterior and posterior surfaces 2062, 2064.

The adjustment assembly 2016 includes a first bracket 2042-*a* that may be referred to as an L-shaped bracket having supporting cross-ribs or other structural features and a second bracket 2042-*b*. The bracket 2042-*a* may include a first slot 2054-*a* that provides anterior/posterior adjustability of the adapter 2014 via connection using a fastener 2040-*a*. The bracket 2042-*a* includes an additional vertically oriented slot 2054-*b* through which a second fastener 2040-*b* extends and is slidable within to provide vertical adjustment of the adapter 2014 relative to the spring assembly 2012. The second fastener 2040-*b* extends through both of the brackets 2042-*a*-*b* to sandwich the spring assembly 2012 therebetween. The vertically oriented slot 2054-*b* is formed in the first bracket 2042-*a* to provide for a vertical sliding adjustment of the adjustment assembly 2016 relative to the spring assembly 2012. The bracket 2042-*a* also includes a slot follower 2051 that is attached to the top spring 2026 by a third fastener 2040-*c* and is slidable within the vertically oriented slot 2054-*b*. The slot follower 2051 slides within the vertically oriented slot 2054-*b* in both the anterior and posterior directions, enabling the top spring 2026 to flex, and in the vertical direction, enabling simple height adjustment. The slot follower 2051 enables the single second fastener 2040-*b* to react the large A-P moments and the slot follower 2051 reacts the medial-lateral moments. The bracket 2042-*b* includes the vertically oriented slot 2054-*b* that provide vertical adjustment of the fasteners 2040-*b*-*c* thereof to provide a height adjustment of the adapter 2014 relative to the spring assembly 2012. The embodiment of FIGS. 45A-45C show the first bracket 2042-*a* mounted to the anterior surface 2062 of the top spring 2026. In other arrangements, the first bracket 2042-*a* may be mounted to the posterior surface 2063 of the top spring 2026.

FIGS. 46A-46C show another example prosthetic device in the form of a prosthetic foot 2100. Specifically, FIG. 46A is a perspective view of the prosthetic foot 2100, FIG. 46B is a perspective view of a first bracket 2142-*a* of the prosthetic foot 2100, and FIG. 46C is a cross-sectional side view of a portion of the prosthetic foot 2100. The prosthetic foot 2100 includes a spring assembly 2112, an adapter 2114, and an adjustment assembly 2116. The spring assembly 2112 includes top and bottom springs 2126, 2128. The top spring 2126 includes anterior and posterior surfaces 2162, 2164.

The adjustment assembly 2116 includes a first bracket 2142-*a* that may be referred to as an L-shaped bracket having supporting cross-ribs or other structural features. The bracket 2142-*a* may include a first slot 2154-*a* that provides anterior/posterior adjustability of the adapter 2114 via connection using a fastener 2140-*a*. The bracket 2142-*a* includes an additional vertically oriented slot 2154-*b* through which a second fastener 2140-*b* extends and is slidable within to provide vertical adjustment of the adapter 2114 relative to the spring assembly 2112. The vertically oriented slot 2154-*b* is formed in the first bracket 2142-*a* to provide for a vertical sliding adjustment of the adjustment assembly 2116 relative to the spring assembly 2112.

The bracket 2142-*a* includes a vertical face 2151 oriented parallel with the coronal plane, a top surface 2153 oriented parallel with the transverse plane, and flanges 2155 oriented parallel to the sagittal plane. The vertical face 2151, the top surface 2153, and the flanges 2155 define a cavity 2157. The top spring 2126 is fastened to the first bracket 2142-*a* at a location inside the cavity 2157 with the single second fastener 2140-*b*. The top spring 2126 is sized and shaped to be positioned within the cavity 2157 such that there is little tolerance between the medial and lateral sides of the top spring 2126 and the flanged 2155. The close fit between the medial and lateral sides of the top spring 2126 and the flanged 2155 enables the flanges 2155 to react to medial-lateral moments and enables alignment between the top spring 2126 and the bracket 2142-*a*. The bracket 2142-*a* may also include shims 2159 that may be positioned within the cavity 2157 between the top spring 2126 and the vertical face 2151, the top surface 2153, and the flanges 2155 to fill the space between the top spring 2126 and the vertical face 2151, the top surface 2153, and the flanges 2155. When adjusting the height of the bracket 2142-*a*, the shim 2159 may be positioned to fill the space between the top spring 2126 and the vertical face 2151, the top surface 2153, and the flanges 2155. The shim 2159 may react to vertical loads, reducing or eliminating the shear load on the fasteners 2140-*a*-*b*. The shims 2159 may be cut from the top spring 2126 when trimming the length of the top spring 2126. Alternatively, the shims 2159 may be provided in incremental lengths as additional components or may be formed of multiple, stacked shims 2159. The embodiment of FIGS. 46A-46C shows the first bracket 2142-*a* mounted to the anterior surface 2162 of the top spring 2126. In other arrangements, the first bracket 2142-*a* may be mounted to the posterior surface 2164 of the top spring 2126.

FIGS. 47A-47C show another example prosthetic device in the form of a prosthetic foot 2200. Specifically, FIG. 47A is an exploded perspective view of the prosthetic foot 2200, FIG. 47B is a front view of the prosthetic foot 2200, and FIG. 47C is a top view of a portion of the prosthetic foot 2200. The prosthetic foot 2200 includes a spring assembly 2212, an adapter 2214, and an adjustment assembly 2216. The spring assembly 2212 includes top and bottom springs 2226, 2228. The top spring 2226 includes anterior and posterior surfaces 2262, 2264.

The adjustment assembly 2216 includes a first bracket 2242-*a* that may be referred to as an L-shaped bracket having supporting cross-ribs or other structural features and a second bracket 2242-*b*. The first bracket 2242-*a* may include a first slot 2254-*a* that provides anterior/posterior adjustability of the adapter 2214 via connection using a fastener 2240-*a*. The first bracket 2242-*a* includes a plurality of holes 2254-*b* through which a plurality of second fasteners 2240-*b* extend to attach the bracket 2242-*a* to the second bracket 2242-*b* to sandwich the spring assembly 2212 therebetween. The brackets 2242-*a*-*b* have a width 2251 that is greater than a width 2253 of the top spring 2226 and the holes 2254-*b* are positioned on the sides of the brackets 2242-*a*-*b* such that the second fasteners 2240-*b* attach the brackets 2242-*a*-*b* together without penetrating the top spring 2226. The brackets 2242-*a*-*b* and the second fasteners 2240-*b* are slidable on the anterior and posterior surfaces 2262, 2264 and the sides of the top spring 2226 to provide vertical adjustment of the adapter 2214 relative to the spring assembly 2212.

In the illustrated embodiment, two pairs of second fasteners 2240-*b* clamp the brackets 2242-*a*-*b* to the top spring 2226 with two second fasteners 2240-*b* positioned on each side of the top spring 2226 and space vertically apart. The strength of the top spring 2226 is increased compared to other embodiments because the second fasteners 2240-*b* do not penetrate the top spring 2226 and no material is removed from the top spring 2226 by drilling holes or creating slots. Vertical forces and medial-lateral moments are reacted by a high friction material 2255 positioned between brackets 2242-*a* and the top spring 2226. In the illustrated embodiment, the high friction material 2255 may include a drywall sanding screen. Alternatively, the high friction material 2255 may include an emery cloth or any other material that enables the prosthetic foot 2200 to operate as described herein. Additionally, a protective layer 2257 may be bonded to the anterior surface 2262 of the top spring 2226 to prevent the high friction material 2255 from cutting surface fibers in a fiber reinforced top spring 2226. In the illustrated embodiment, the protective layer 2257 includes a thermoplastic material with a Young's modulus between about 200,000 and about 2,000,000 psi and has a thickness between about 0.05 and about 0.10 mm. The protective layer 2257 may include a fiber reinforced thermoplastic material such as a 20% glass fiber reinforced nylon. The protective layer 2257 enables limited embedding of the high friction material 2255 into the protective layer 2257 to maximize friction or grip between the high friction material 2255 and the protective layer 2257. The protective layer 2257 may be bonded to the top spring 2226 using an adhesive including epoxy, acrylic, and urethane. Alternatively, the protective layer 2257 may be co-cured with the top spring 2226, eliminating the additional step of bonding the protective layer 2257 to the top spring 2226. The embodiment of FIGS. 47A-76C show the first bracket 2242-*a* mounted to the anterior surface 2262 of the top spring 2226. In other arrangements, the first bracket 2242-*a* may be mounted to the posterior surface 2263 of the top spring 2226.

Figures 48A, 48B, 48C:
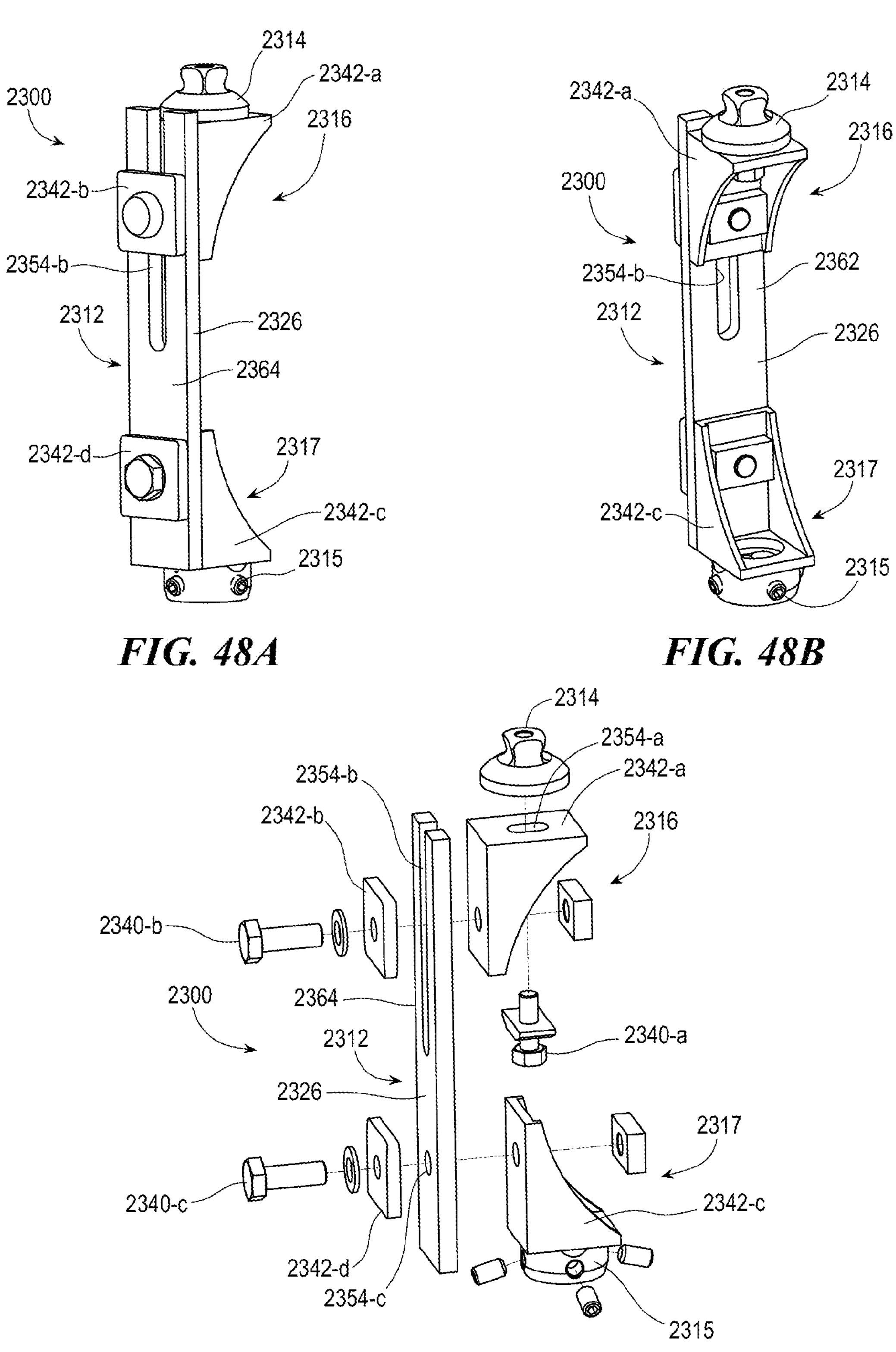
FIGS.48A-48C show an example of a prosthetic device in the form of a prosthetic pylon 2300.

FIGS. 48A-48C show an example of a prosthetic device in the form of a prosthetic pylon 2300. Specifically, FIG. 48A is a back-perspective view of the prosthetic pylon 2300, FIG. 48B is a front-perspective view of the prosthetic pylon 2300, and FIG. 48C is an exploded perspective view of the prosthetic pylon 2300. The prosthetic pylon 2300 is configured to connect a prosthetic socket to a prosthetic foot when a height of the prosthetic foot is insufficient to reach the prosthetic socket. The prosthetic pylon 2300 includes a spring assembly 2312, a first adapter 2314, a second adapter 2315, a first adjustment assembly 2316, and a second assembly 2317. The spring assembly 2312 includes a rectangular, fiber-reinforced plastic (FRP) spring 2326. When assembled into a prosthetic leg the prosthetic pylon 2300 is preferably oriented with the spring 2326 posterior to the adapters 2314 and 2315 because this orientation applies maximum moment to the spring during toe loading and maximizes energy storage. However, alternate orientations may be utilized to optimize the performance of a particular prosthetic foot or an amputees unique activities.

The first adjustment assembly 2316 includes a first bracket 2342-*a* that may be referred to as an L-shaped bracket having supporting cross-ribs or other structural features and a second bracket 2342-*b*. The first bracket 2342-*a* may include a first slot 2354-*a* that provides anterior/posterior adjustability of the first adapter 2314 via connection using a first fastener 2340-*a*. The first bracket 2342-*a* includes an additional vertically oriented slot 2354-*b* through which a second fastener 2340-*b* extends and is slidable within to provide vertical adjustment of the adapter 2314 relative to the spring assembly 2312. The second fastener 2340-*b* extends through both of the brackets 2342-*a*-*b* to sandwich the spring assembly 2312 therebetween. The vertically oriented slot 2354-*b* is formed in the first bracket 2342-*a* to provide for a vertical sliding adjustment of the first adjustment assembly 2316 relative to the spring assembly 2312. The first bracket 2342-*a* includes the vertically oriented slot 2354-*b* that provide vertical adjustment of the second fastener 2340-*b* thereof to provide a height adjustment of the adapter 2314 relative to the spring assembly 2312.

The second adjustment assembly 2017 includes a third bracket 2342-*c* that may be referred to as an L-shaped bracket having supporting cross-ribs or other structural features and a fourth bracket 2342-*d*. The second adapter 2315 is directly connected to the third bracket 2342-*c*. The third bracket 2342-*c* includes an additional vertically oriented hole 2354-*c* through which a third fastener 2340-*c* extends. The third fastener 2340-*c* extends through both of the brackets 2342-*c*-*d* to sandwich the spring assembly 2312 therebetween.

During operations, the first adapter 2314 is connected a prosthetic socket and the second adapter 2315 is connected to a prosthetic foot. The height of the prosthetic pylon 2300 is adjusted by adjusting the height of the first adjustment assembly 2316. Specifically, the second fastener 2340-*b* is loosened and the height of the first bracket 2342-*a* and the first adapter 2314 is adjusted to the desired height. The second fastener 2340-*b* is then tightened to maintain the first bracket 2342-*a* and the first adapter 2314 at the desired height.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on" as used in the specification and the claims is to be construed as meaning "based at least upon."

What is claimed is:

1. A prosthetic foot, comprising:

an elongate support member comprising fiber reinforced material and having a support surface configured to rest upon a ground surface prior to use;

an adapter mounted to the support member and configured to secure the prosthetic foot to another prosthetic device; and a height adjustable feature configured to adjust a height of the adapter relative to the support surface, wherein the height adjustable feature includes an adapter support to which the adapter is mounted, and a bolt extending through the support member and into engagement with the adapter support to releasably secure the adapter support to the support member, wherein the adapter support includes a contoured portion, the contoured portion facing a surface of the support member and configured to contact the support member during use of the prosthetic foot to alter a moment arm length between the bolt and adapter support, and wherein the contoured portion comprises a curved surface configured to contact the support member.

2. The prosthetic foot of claim 1, wherein the adapter includes:

a base portion and a pyramid connector, the pyramid connector configured to secure the prosthetic foot to another prosthetic device, and the base portion configured to secure the adapter to the support member via the height adjustable feature.

3. The prosthetic foot of claim 1, wherein the height adjustable feature includes a first portion mounted to the support member, and a second portion mounted to the adapter, and the first and second portions are slidable relative to each other to provide height adjustment of the adapter relative to the support surface.

4. The prosthetic foot of claim 3, wherein the first portion includes a groove, and the second portion includes a protrusion positioned and slidable within the groove.

5. The prosthetic foot of claim 1, wherein the height adjustable feature includes at least one set screw to releasable hold the adapter in an adjusted height relative to the support surface.

6. The prosthetic foot of claim 1, wherein the height adjustable feature includes a slot formed in the support member, and a bolt extending through and slidable within the slot to provide the height adjustment of the adapter.

7. The prosthetic foot of claim 1, wherein the adapter support having a slot formed therein, and the bolt extends through the support member and slidable within the slot to provide the height adjustment of the adapter.

8. The prosthetic foot of claim 1, wherein the support member includes a vertical portion extending in a vertical direction, and the adapter is positioned anterior of the vertical portion.

9. The prosthetic foot of claim 1, wherein the support member includes a vertical portion extending in a vertical direction, and the adapter is positioned posterior of the vertical portion.

10. The prosthetic foot of claim 1, wherein the support member includes a vertical portion extending in a vertical direction, and the vertical portion includes at least one slot formed therein, the at least one slot arranged vertically.

11. The prosthetic foot of claim 1, wherein the support member includes a vertical portion extending in a vertical direction, and the adapter support has at least one slot formed therein, the at least one slot arranged vertically, the adapter support being adjustably mounted to the vertical portion of the support member.

12. The prosthetic foot of claim 1, wherein the support member includes a vertical portion extending in a vertical direction, and the adapter support having at least one slot formed therein, the at least one slot arranged vertically, the adapter support being mounted to the vertical portion of the support member, and the adapter being adjustably mounted to adapter support.

13. A prosthetic foot, comprising:

a spring assembly having a first portion extending horizontally and arranged to contact a ground surface, and a second portion having an adapter mounting portion; and an adapter assembly comprising:

a connector configured to releasably secure the prosthetic foot to a prosthetic device;

a base portion interposed between the connector and the spring assembly;

at least one fastener to releasably secure the adapter assembly to the spring assembly; and a height adjustable feature configured to adjust a height of the adapter assemble relative to the spring assembly, wherein the height adjustable feature includes an adapter support to which the adapter assembly is mounted, and the at least one fastener extends through the spring assembly and into engagement with the adapter support to releasably secure the adapter support to the spring assembly, wherein the adapter support includes a contoured portion, the contoured portion facing a surface of the spring assembly and configured to contact the spring assembly during use of the prosthetic foot to alter a moment arm length between the at least one fastener and adapter support, and wherein the contoured portion comprises a curved surface configured to contact the spring assembly;

wherein the prosthetic foot is operable to adjust an effective height of the connector relative to the ground surface.

14. The prosthetic foot of claim 13, wherein the second portion of the spring assembly is arranged vertically.

15. The prosthetic foot of claim 13, wherein the second portion of the spring assembly is arranged horizontally.

16. The prosthetic foot of claim 13, wherein one of the second portion of the spring assembly and the base portion includes at least one slot through which the at least one fastener extends and is slidable within to provide the height adjustment.

17. A method of adjusting an effective height of a prosthetic device, comprising:

providing a prosthetic device comprising an elongate composite spring member, an adapter, and a height adjustable feature interposed between the spring member and the adapter, wherein the height adjustable feature includes an adapter support to which the adapter is mounted, and a bolt extending through the elongate composite spring member and into engagement with the adapter support to releasably secure the adapter support to the elongate composite spring member, wherein the adapter support includes a contoured portion, the contoured portion facing a surface of the elongate composite spring member and configured to contact the elongate composite spring member during use of the prosthetic device to alter a moment arm length between the bolt and adapter support, and wherein the contoured portion comprises a curved surface configured to contact the elongate composite spring member; and operating the height adjustable feature to move the adapter relative to the spring member to adjust an effective height of the adapter.

18. The method of claim 17, wherein the spring member includes a vertically arranged portion, and the height adjustable feature is movable vertically relative to the vertically arranged portion.

19. The method of claim 18, wherein at least one of the vertically arranged portion and the height adjustable feature includes at least one slot, the prosthetic device further including at least one fastener extending through the at least one slot to releasably hold a position of the adapter relative to the spring member.

20. A method of adjusting an effective height of a prosthetic foot, comprising:

providing a prosthetic foot comprising an elongate composite spring assembly having a first portion configured to contact a ground surface and a vertically arranged portion, an adapter, and a height adjustable feature interposed between the vertically arranged portion and the adapter, wherein the height adjustable feature includes an adapter support to which the adapter is mounted, and a bolt extending through the elongate composite spring assembly and into engagement with the adapter support to releasably secure the adapter support to the elongate composite spring assembly, wherein the adapter support includes a contoured portion, the contoured portion facing a surface of the elongate composite spring assembly and configured to contact the elongate composite spring assembly during use of the prosthetic foot to alter a moment arm length between the bolt and adapter support, and wherein the contoured portion comprises a curved surface configured to contact the elongate composite spring assembly; and adjusting a position of the adapter relative to the elongate composite spring assembly with the height adjustable feature to change a height of the adapter relative to the ground surface.

21. The method of claim 20, wherein the height adjustable feature includes an indexed member that provides predefined height adjustments.

22. The method of claim 21, wherein at least one of the spring assembly, the adapter, and the height adjustable feature includes at least one slot, the prosthetic foot further including at least one fastener extending through the at least one slot to releasably hold a position of the adapter relative to the spring assembly.

* * * * *